(12) United States Patent
Warren et al.

(10) Patent No.: US 7,857,756 B2
(45) Date of Patent: Dec. 28, 2010

(54) ARCHITECTURE TOOL AND METHODS OF USE

(75) Inventors: William L. Warren, Stillwater, OK (US); Robert L. Parkhill, Stillwater, OK (US); Robert L. Stewart, Stillwater, OK (US); Anatoly M. Kachurin, Stillwater, OK (US); Robert M. Taylor, Perkins, OK (US); Kenneth H. Church, Stillwater, OK (US)

(73) Assignee: Sciperio, Inc., Stillwater, OK (US)

( * ) Notice: Subject to any disclaimer, the term of this patent is extended or adjusted under 35 U.S.C. 154(b) by 0 days.

(21) Appl. No.: 10/891,512

(22) Filed: Jul. 15, 2004

(65) Prior Publication Data

US 2004/0253365 A1 Dec. 16, 2004

Related U.S. Application Data

(62) Division of application No. 10/227,146, filed on Aug. 23, 2002, now Pat. No. 6,986,739.

(60) Provisional application No. 60/314,344, filed on Aug. 23, 2001, provisional application No. 60/337,378, filed on Dec. 4, 2001, provisional application No. 60/337,383, filed on Dec. 4, 2001, provisional application No. 60/340,706, filed on Dec. 11, 2001.

(51) Int. Cl.
*A61B 1/12* (2006.01)

(52) U.S. Cl. .................... 600/159; 600/156; 600/158

(58) Field of Classification Search ................ 600/105, 600/156, 158
See application file for complete search history.

(56) References Cited

U.S. PATENT DOCUMENTS

| | | | |
|---|---|---|---|
| 4,437,581 A | 3/1984 | Coker | |
| 4,485,387 A | 11/1984 | Drumheller | |
| 4,535,919 A | 8/1985 | Jameson | |
| 4,586,854 A | 5/1986 | Newman et al. | |
| 4,598,841 A | 7/1986 | Smiles | |
| 4,601,645 A | 7/1986 | Schmitkons | |
| 4,615,649 A | 10/1986 | Sharpless | |
| 4,657,047 A | 4/1987 | Kolibas | |
| 4,711,379 A | 12/1987 | Price | |
| 4,922,852 A | 5/1990 | Price | |
| 4,989,792 A | 2/1991 | Claassen | |
| 5,037,247 A | 8/1991 | Kaiser et al. | |
| 5,067,882 A | 11/1991 | DeVries et al. | |
| 5,078,325 A | 1/1992 | Waryu et al. | |
| 5,325,762 A | 7/1994 | Walsh et al. | |
| 5,447,254 A | 9/1995 | Hoover et al. | |
| 5,495,963 A | 3/1996 | Miller et al. | |
| 5,521,576 A | 5/1996 | Collins | |
| 5,548,268 A | 8/1996 | Collins | |
| 5,558,136 A | 9/1996 | Orrico | |
| 5,575,756 A * | 11/1996 | Karasawa et al. | 600/157 |
| 5,588,432 A * | 12/1996 | Crowley | 600/439 |
| 5,620,138 A | 4/1997 | Crum | |

(Continued)

*Primary Examiner*—Matthew J Kasztejna
(74) *Attorney, Agent, or Firm*—McKee, Voorhees & Sease, P.L.C.

(57) ABSTRACT

The invention provides an apparatus and methods for depositing materials on a substrate, and for performing other selected functions, such as material destruction and removal, temperature control, imaging, detection, therapy and positional and locational control. In various embodiments, the apparatus and methods are suitable for use in a tabletop setting, in vitro or in vivo.

15 Claims, 30 Drawing Sheets

U.S. PATENT DOCUMENTS

| | | |
|---|---|---|
| 5,620,139 A | 4/1997 | Ziecker |
| 5,692,884 A | 12/1997 | Allen et al. |
| 5,700,323 A | 12/1997 | Koch et al. |
| 5,715,864 A | 2/1998 | Andel et al. |
| 5,720,894 A | 2/1998 | Neev et al. |
| 5,727,931 A | 3/1998 | Lash et al. |
| 5,747,102 A | 5/1998 | Smith et al. |
| 5,776,050 A * | 7/1998 | Chen et al. .................. 600/117 |
| 5,791,531 A | 8/1998 | Hassler, Jr. |
| 5,829,647 A | 11/1998 | Miller |
| 5,890,514 A | 4/1999 | Siddiqui |
| 5,921,759 A | 7/1999 | Khan |
| 5,971,976 A | 10/1999 | Wang et al. |
| 5,984,148 A | 11/1999 | Andel et al. |
| D420,099 S | 2/2000 | Lewis et al. |
| 6,056,155 A | 5/2000 | Byerly et al. |
| 6,060,125 A | 5/2000 | Fujii |
| 6,066,102 A * | 5/2000 | Townsend et al. ........... 600/564 |
| 6,152,386 A | 11/2000 | Bullock et al. |
| 6,155,806 A | 12/2000 | Andel |
| 6,161,722 A | 12/2000 | Sooudi et al. |
| 6,167,296 A * | 12/2000 | Shahidi ...................... 600/427 |
| 6,190,353 B1 * | 2/2001 | Makower et al. ......... 604/95.01 |
| 6,206,667 B1 | 3/2001 | Turner, Jr. et al. |
| 6,212,997 B1 | 4/2001 | McCollough et al. |
| 6,250,515 B1 | 6/2001 | Newbold et al. |
| 6,253,957 B1 | 7/2001 | Messerly et al. |
| 6,267,266 B1 | 7/2001 | Smith et al. |
| 6,282,442 B1 * | 8/2001 | DeStefano et al. ............ 604/21 |
| 6,309,370 B1 * | 10/2001 | Haim et al. ................... 604/66 |
| 6,388,345 B1 * | 5/2002 | Stimpson .................... 307/119 |
| 6,394,956 B1 * | 5/2002 | Chandrasekaran et al. .. 600/439 |
| 6,475,139 B1 * | 11/2002 | Miller ........................ 600/135 |
| 6,572,532 B1 * | 6/2003 | Pratt et al. ..................... 600/30 |
| 6,712,757 B2 * | 3/2004 | Becker et al. ............... 600/121 |
| 7,491,198 B2 * | 2/2009 | Kockro .......................... 606/1 |

* cited by examiner

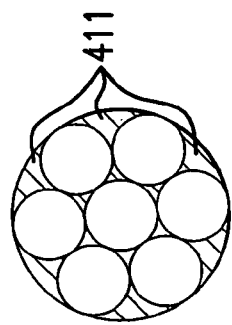
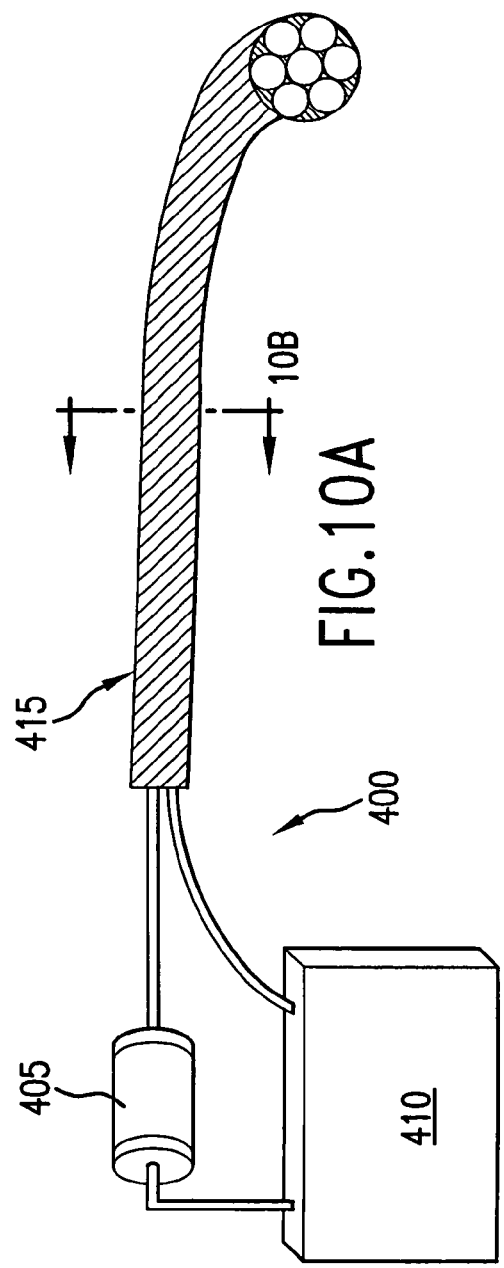
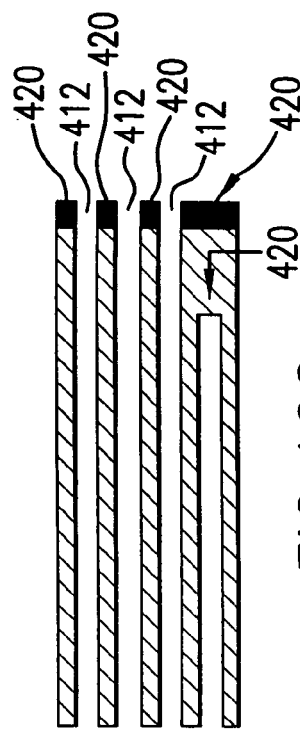
FIG.10B
FIG.10A
FIG.10C

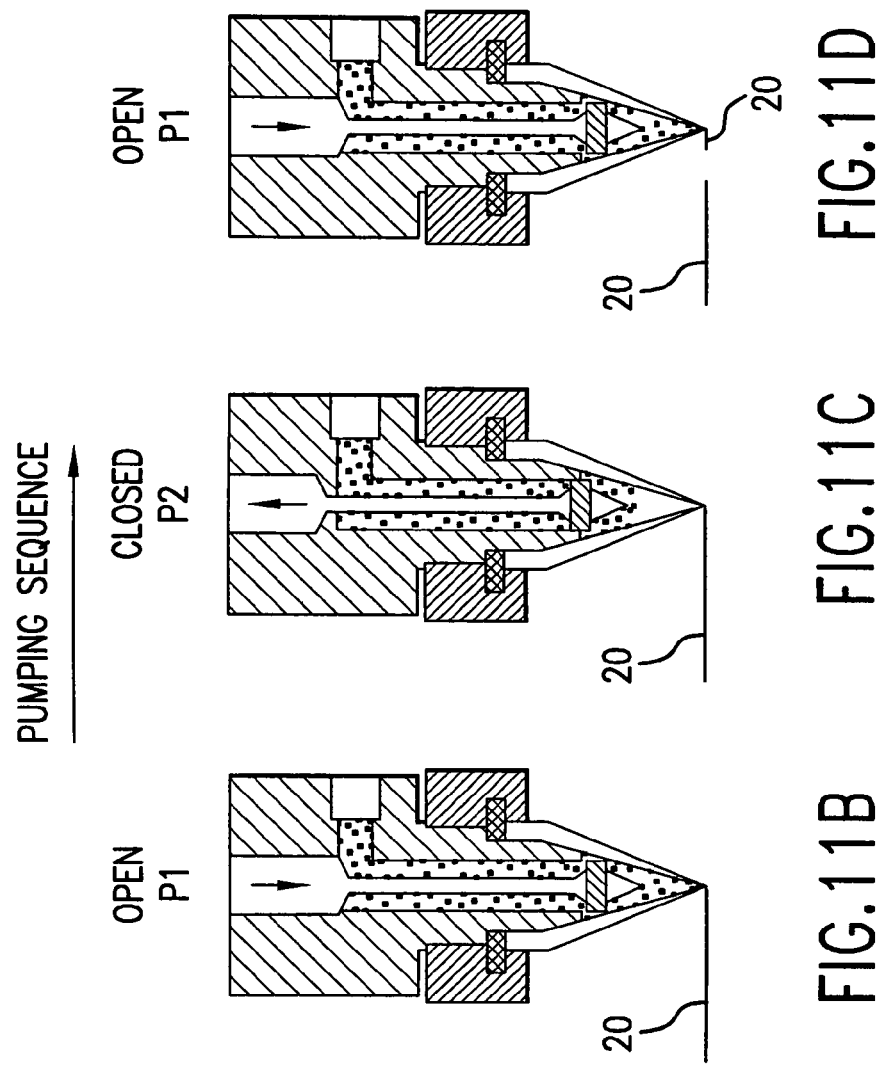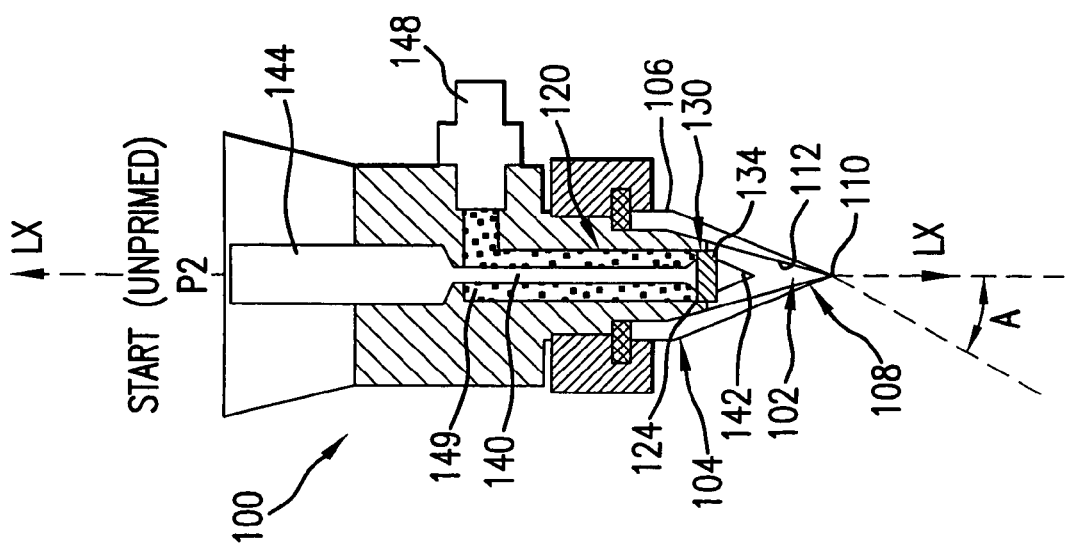

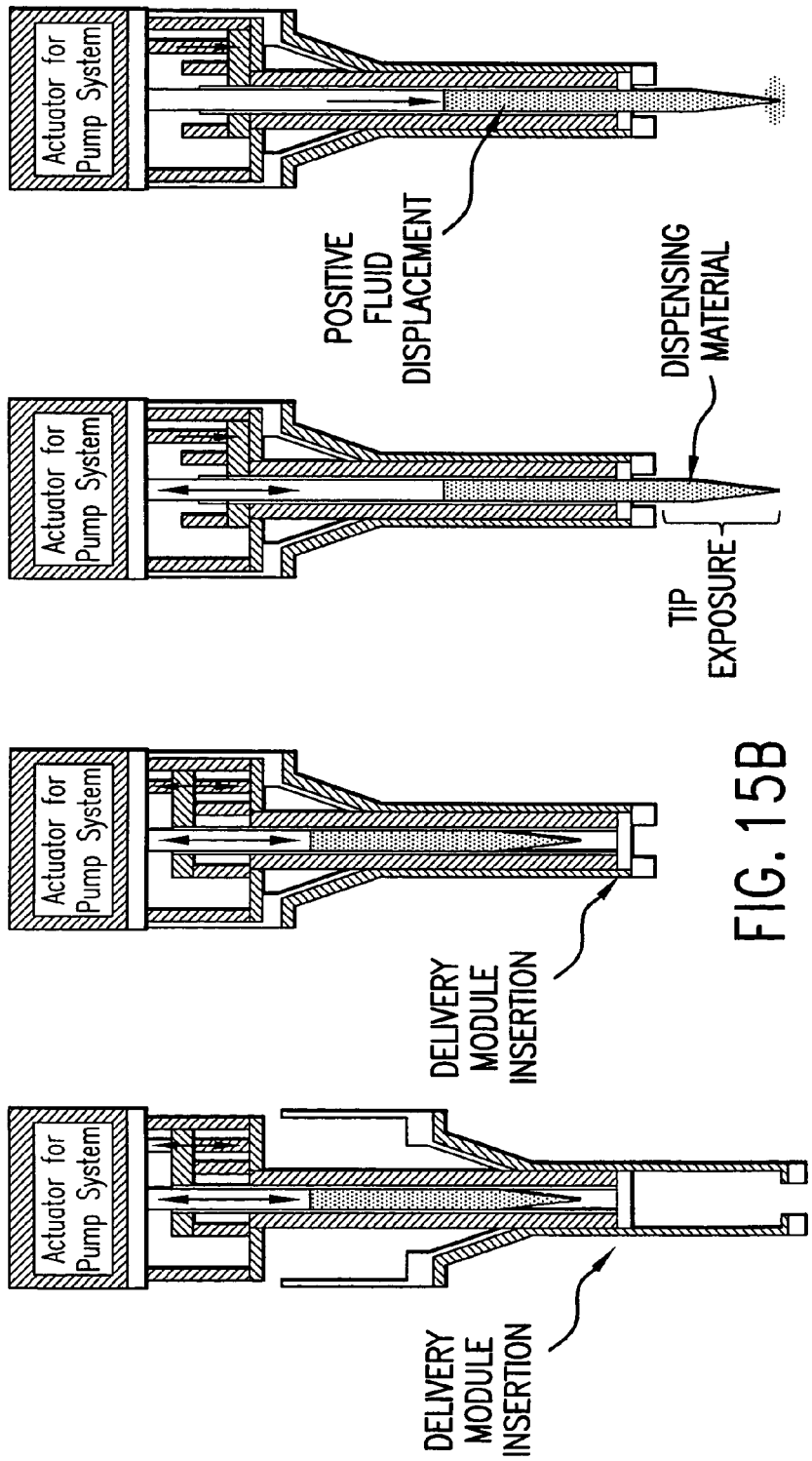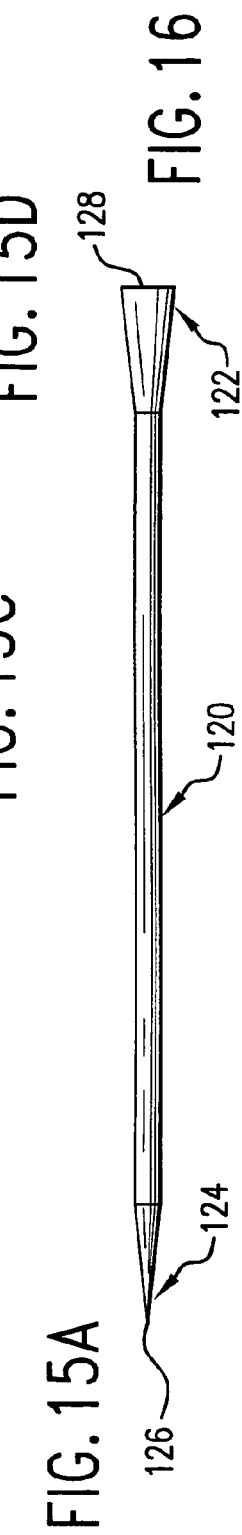

White Blood Cells

Cells Deposited

Various Input Material Streams

Four-Stream mixer Configuration

Mixing Effects of Pulsed Material Flow

Constant Flow

Mixing Effects of Pulsed Material Flow

Pulsed Flow

ARCHITECTURE TOOL AND METHODS OF USE

This application is a divisional of U.S. Ser. No. 10/227,146, filed Aug. 23, 2002, now U.S. Pat. No. 6,986,739, which claims priority to application Ser. No. 60/314,344, filed Aug. 23, 2001, which claims benefit of application Ser. No. 60/337,378, filed Dec. 4, 2001, which claims benefit of application Ser. No. 60/337,383, filed Dec. 4, 2001, which claims benefit of application Ser. No. 60/340,706, filed Dec. 11, 2001. The entirety of these application are incorporated herein by reference.

STATEMENT OF FEDERALLY SPONSORED RESEARCH

This invention was made with government support under Grant No. NBCHC010019 awarded by the Defense Advancement Research Projects Agency. The United States government may have certain rights in the invention.

FIELD OF THE INVENTION

This invention relates generally to tools and methods for depositing materials accurately on a selected substrate, or for performing a variety of other tasks, including material removal, imaging, and detection. The invention may be applied in the medical and biological fields, but is also applicable in many other environments and fields, including the manufacture of a broad range of devices.

BACKGROUND OF THE INVENTION

Because of the importance of three-dimensional (3D) structure (microenvironment) to the cell function, a goal in metabolic and tissue engineering is to control the spatial arrangement of cells to mimic the 3D ordering of cells in native tissues. To date, many efforts toward this goal have focused on two-dimensional (2D) patterns using photolithography or microcontact printing of a single cell type. The 2D cell patterns provide two types of micrometer-scale regions, one in which the cells adhere, while the other has low cell adhesion. The design intent is for the cells to adhere selectively to the patterned regions of high adhesion.

The aforementioned lithographic process is somewhat successful for one cell type; however, culturing more than one cell type requires differential adhesion between the two cell types. The lithographic process falls short of the true 3D mark required to create the proper microenvironment for cell growth.

Current approaches, to include transplantation, transfusion of cells into a preformed implantable biocompatible matrix, or 2D in vitro culturing of tissues, require both expensive and timely custom fabrication and tremendously invasive surgeries.

A recent review article by Jung et al. articulates the importance of topographical and physiochemical modification—the microenvironment—of the material surface to enable patterning of living cells. See D. R. Jung, R. Kapur, T. Adams, K. A. Giuliano, M. Mrksich, H. G. Craighead, and D. L. Taylor, *Critical Reviews in Biotechnology* 2001, 21, 111, which is expressly incorporated herein in its entirety by this reference. The article provides several examples of the precise control of the architecture of multiple cells via precise engineering of the material surface (cell patterning). It is shown that selective phenotypic and genotypic control of living tissues is provided by surface topographic and physiochemical treatments. Surface is italicized above to illustrate that while this technology is highly successful for such applications as cell-based assays for drug discovery and planar biosensor arrays, it does not satisfy the 3D requirements for metabolic and tissue engineering.

Existing tissue and organ losses are treated by transplantation of an organ from a donor, through surgical reconstruction, or by the use of a mechanical-type substitute. Most potential recipients die waiting for available transplant organs. Those fortunate enough to receive a donor organ are relegated to a lifetime of immunosuppression therapy. The option of surgical reconstruction, although usually involving the patient's own tissues, again is not appropriate for many situations and is associated with significant morbidity. The burden to the patient and the health-care delivery system due to the extensive surgery often required and the high number of repeat procedures is no longer inline with the objectives of modern treatment preferences. Mechanical devices, such as kidney dialysis machines, provide a therapeutic value but represent a mere life-sustaining function for now and in the future.

Thus, a need exists to recreate the 3D relations among cells and bioactive substances that are necessary to normal tissue morphogenesis and organ functions through a tool that introduces the new constructs with minimal trauma to the host. A need exists for a tool that combines additive and subtractive processes in one integrated embodiment. For biological and/or medical applications, this is especially true if the tool can be integrated with minimally invasive surgery (MIS) techniques. A need also exists for technologies that enable such a tool and its use, including pumping systems, material delivery and mixing systems, position control systems, material dispensing systems, material destruction and removal systems, material temperature control systems, imaging and detection systems, and therapeutic systems.

SUMMARY OF THE INVENTION

As described herein, in one embodiment, the invention includes a direct-write patterning system suitable for either fine-pattern microdispensing and/or fine-focused laser-beam writing over flat or conformal surfaces. One illustrative use of the invention is for dispensing uniform lines of viscous solutions, suspensions, sols, or pastes to create exact replicas of stored patterns. Materials that may be deposited according to the invention include, but are not limited to, dielectric pastes and/or inks, semiconducting pastes, conducting pastes, polymers, hydrogels, cells, growth factors, nutrients, and extracellular matrix materials. In another embodiment, the invention provides integrated tool technologies for the direct-write deposition and laser micromachining of a wide variety of such materials and provides the capability for concurrent detection and imaging methods during additive and subtractive processes.

The direct-write technologies may be used to construct purely inorganic materials, purely organic materials, biological materials and/or any combination thereof. Throughout this specification, the direct-write deposition technology in general terms will be referred to as "direct-write deposition technology" (DWDT).

The DWDT technology includes embodiments in which the apparatus of the invention is sized and shaped to enable use of the tool, for example, in MIS or other in vivo procedures as shown in FIG. 1. As set forth in further detail below, the tool in such embodiments may be a suitably small and maneuverable device to allow its use in endoscopic procedures, and may thus comprise an endoscopic device.

Alternatively, such small and maneuverable embodiments may be utilized for applications, including organic and inorganic applications, in a "tabletop" setting (FIGS. 2A-2F). In another aspect, alternative embodiments of the invention include a larger, less maneuverable tabletop version of the tool in which constituent materials may be dispensed through multiple, discrete dispensing heads. Tabletop embodiments may also be utilized to perform all of the same biological, tissue-engineering, and medical-process applications using the same constituent printing materials as the in vivo embodiments described herein. Thus, all embodiments disclosed herein for application in vivo may suitably be adapted for in vitro use and for tabletop settings. Similarly, embodiments disclosed herein for in vitro use or in tabletop settings may also be used or adapted for use in vivo. The described embodiments are not to be viewed as limited to either in vivo or in vitro usage.

For biological, medical, bioengineering, and tissue-engineering embodiments of the DWDT, the apparatus may be referred to herein as the "human architecture tool" (HAT). The in vitro and/or in vivo HAT technology described herein can allow the user to "print" biocompatible scaffolds, cells, growth factors, therapeutics, enzymes, extracellular matrix (ECM) proteins, and the like inside the human body using a microscale dispensing orifice (e.g., a dispenser or stylus) compatible with MIS medical practices. The HAT technology is able to remove any unwanted tissue or substrate without trauma to surrounding structures using a novel fiber-delivered ultrashort-pulse (USP) laser system in the same MIS-compatible tool.

In various embodiments, the DWDT may be used to perform biological, medical, bioengineering, bioelectronic, and tissue-engineering procedures, but it also may be used for non-medical applications, such as fabricating intricate electronic devices, including but not limited to, resistors, varistors, capacitors, varactors, interconnects, transistors, diodes, metal-semiconductor rectifiers, antennas, fuel cells, and batteries, for applications such as microelectromechanical systems (MEMS), embedded batteries, polymer light-emitting diodes, surface acoustic wave devices, sensors (e.g., temperature, pressure, gas, humidity), decorative patterning, solar cells, transmission electron micrographic (TEM) sample extraction, three-dimensional (3D) metrology, via filling, interconnect patterning, thin-film head trimming, trimming and repair, lenses, waveguides, on a variety of conformal surfaces.

In various embodiments, the HAT may be used for applications including a broad variety of regenerative medicine and tissue engineering techniques, which include but are not limited to, building customized body parts on demand, in real time.

Additional advantages of the invention will be set forth in part in the description which follows, and in part may be learned from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

FIGS. 10A-10C are views of an embodiment of a temperature controller of the invention.

FIGS. 11A-11D are sequential operational views of an embodiment of the material dispenser of the invention.

FIGS. 15A-15D are sequential operational views of an embodiment of the material dispenser of the invention.

FIG. 16 is a side view of a feed channel for use in an embodiment of the material dispenser of the invention.

DETAILED DESCRIPTION OF THE INVENTION

Figure 1:
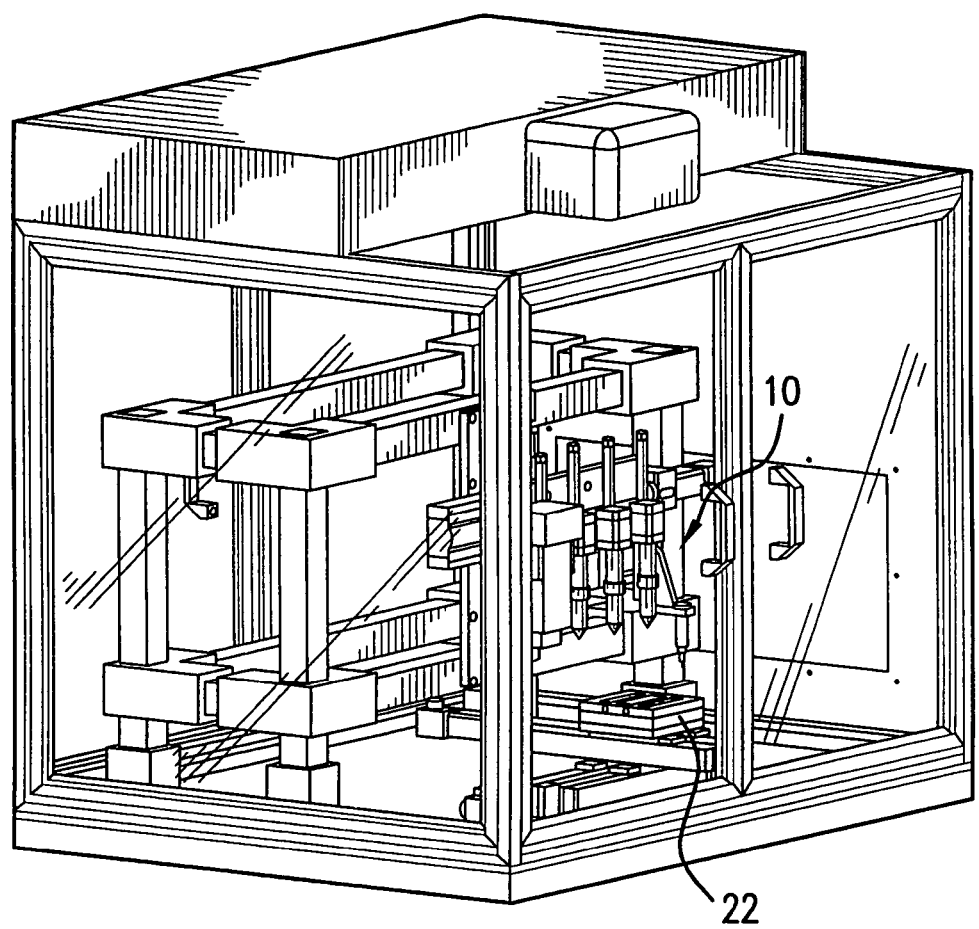
FIG. 1 is a perspective view of an embodiment of the invention for tabletop use.

The present invention is more particularly described in the following examples that are intended as illustrative only since numerous modifications and variations therein may be apparent to those skilled in the art. As used in the specification and in the claims, "a," "an," and "the" can mean one or more, depending upon the context in which it is used. Several aspects of the present invention are now described with reference to the figures, in which like numbers indicate like parts throughout the figures.

For convenience, abbreviations and symbols used throughout this specification are set forth in the following Tables 1 and 2.

TABLE 1

| ABBREVIATIONS | |
|---|---|
| 2D, 3D | N Dimensions, -Dimensional |
| AF | Autofluorescence |
| BCGF | B-Cell Growth Factor |
| CAD | Computer Aided Design |
| CAM | Computer Aided Manufacturing |
| CCD | Charge-Coupled Device |
| CFD | Computational Fluid Dynamics |
| CMU | Carnegie Mellon University |
| CRT | Cathode Ray Tube |
| CSF | Colony Stimulating Factor |
| CT | Computerized Tomography |
| CTGF | Connective Tissue Growth Factor |
| CW | Continuous Wave (Laser) |
| DNA | Deoxyribonucleic Acid |
| DPIV | Digital Particle Image Velocimetry |
| DPM | Distributed Parameter Model |
| DWDT | Direct-Write Deposition Technology |
| ECGF | Endothelial Cell Growth Factor |
| ECM | Extracellular Matrix |
| EF | Exogenous Fluorescence |
| EGF | Endothelial Growth Factor |
| ENT | Endogenous Natural Tissue |
| Epo | Erythropoietin |
| YAG | Yttrium Aluminum Garnet |
| E-SEM | Environmental SEM |
| ETC | Engineered Tissue Construct |
| f/# | Focal Number |

TABLE 1-continued

| ABBREVIATIONS | |
|---|---|
| FD | Finite-Dimensional |
| FGF | Fibroblast Growth Factor |
| FIB | Focused Ion Beam |
| FSR | Femtosecond Regime ($10^{-15}$-$10^{-13}$ s) |
| FTIR | Fourier-Transform Infrared Spectroscopy |
| FTL | Follow-the-Leader (Motion) |
| FWHM | Full Width at Half Maximum |
| GCSEL | Grating-Coupled Surface-Emitting Laser |
| HAT | Human Architecture Tool |
| HBEGF | Heparin Binding Epidermal Growth Factor |
| HGF | Hepatocyte Growth Factor |
| HGFL | Hepatocyte Growth Factor-Like |
| HMG | High-Mobility Group Protein |
| ID | Infinite-Dimensional |
| IFN | Interferon |
| IGF | Insulin-Like Growth Factor |
| IGFBP | IGF Binding Protein |
| IL | Interleukin |
| INGAP | Pancreatic Beta Cell Growth Factor |
| IR | Infrared (Radiation) |
| KGF | Keratinocyte Growth Factor |
| LASIK | Laser In Situ Keratomileusis |
| LED | Light-Emitting Diode |
| LEPT | Low-Energy Photon Therapy |
| LGF | Laplacian-Gaussian Filter |
| LIF | Laser-Induced Fluorescence |
| lomo | Locally Monotonic |
| LP | Long Pulse (Laser) |
| LTBP | Latent Transforming Growth Factor Beta Binding Protein |
| MEMS | Microelectromechanical Systems |
| MIS | Minimally Invasive Surgery |
| MRI | Magnetic Resonance Imaging |
| mRNA | Messenger RNA |
| MST | Macrophage-Stimulating |
| MTC | Model Tissue Construct |
| NA | Numerical Aperture |
| NGF | Nerve Growth Factor |
| NLO | Nonlinear Optics, -Optical |
| NSR | Nanosecond Regime ($10^{-9}$-$10^{-7}$ s) |
| OCT | Optical Coherence Tomography |
| OM | Optical Micrograph |
| OSU | Oklahoma State University |
| PBF | Photonic Bandgap Fiber (Material) |
| PC | Personal Computer |
| PCR | Polymerase Chain Reaction |
| PDGF | Platelet-Derived Growth Factor |
| PEG | Poly(ethylene glycol) |
| PGFL | Placental Growth Factor-Like |
| PPF | Poly(propylene fumarate) |
| PSR | Picosecond Regime ($10^{-12}$-$10^{-10}$ s) |
| R&D | Research & Development |
| RNA | Ribonucleic Acid |
| S/N | Signal to Noise Ratio |
| SEM | Scanning Electron Micrograph |
| SCDGF | Spinal Cord-Derived Growth Factor |
| SCGF | Stem Cell Growth Factor |
| SRS | Stimulated Raman Scattering |
| TDGF | Teratocarcinoma-Derived Growth Factor |
| TEM | Transmission Electron Micrograph |
| TGF | Transforming Growth Factor |
| TNF | Tumor Necrosis Factor |
| TSL | Titanium-Doped Sapphire Laser |
| TV | Television |
| UA | University of Arizona |
| USP | Ultrashort Pulse (Laser) |
| UV | Ultraviolet (Radiation) |
| VEGF | Vascular Endothelial Growth Factor |
| VGR | Vegetal Related Growth Factor |
| WBC | White Blood Cell |

TABLE 2

SYMBOLS

| | |
|---|---|
| a | Areal Density ($m^{-2}$) |
| A | Amplitude or Magnitude |
| d | Diameter (m) |
| $E_p$ | Energy, Pulse (J) |
| f | Frequency (Hz) |
| $f_r$ | Frequency, Resonance (Hz) |
| F | Fluence or Energy Density ($J/m^2$) |
| $F_{ablation}$ | Fluence, Ablation Threshold ($J/m^2$) |
| $F_{damage}$ | Fluence, Damage Threshold ($J/m^2$) |
| H | Irradiance or Power Density ($W/m^2$) |
| L | Nozzle Design Parameter (m) |
| n | Refractive Index |
| p | Pressure (Pa) |
| $P_{avg}$ | Power, Average (W) |
| $P_{in}$ | Power, Input (W) |
| $P_{out}$ | Power, Output (W) |
| $P_{peak}$ | Power, Peak (W) |
| $P_{th}$ | Power, Threshold (W) |
| Q | Quality Factor |
| r | Radius (m) |
| Re | Reynolds Number (–) |
| $R_p$ | Repetition Rate, Pulse (Hz) |
| t | Time or Period (s) |
| u | Velocity, Fluid (m/s) |
| U | Flow Rate, Fluid (L/s) |
| w | Spot Size (m) |
| x, y, z | Cartesian Coordinates (m) |
| Z | Impedance (Ω) |
| Δ | Difference Operator |
| λ | Wavelength (m) |
| $\lambda_f$ | Wavelength, Fluorescence (m) |
| μ | Viscosity, Dynamic (Pa s) |
| ρ | Density ($kg/m^3$) |
| $\tau_f$ | Duration, Fluorescence Decay (s) |
| $\tau_p$ | Duration, Pulse (s) |
| $\tau_s$ | Shear Stress (Pa) |
| $\tau_{s\text{-}wall}$ | Shear Stress, Wall (Pa) |

The invention includes embodiments of a tool for in vitro or in vivo use in biological, tissue-engineering, and medical processes. A DWDT embodiment of the invention for in vitro use is illustrated in FIG. 1. Embodiments for in vivo use may be sized and shaped to enable use of the tool in MIS procedures as shown in FIGS. 2A-F. As set forth in further detail below, the tool in its in vivo embodiments may be a suitably small and maneuverable device to allow its use in endoscopic procedures. Alternatively, such small and maneuverable embodiments may be utilized for in vitro applications in a tabletop setting (FIG. 1). In other alternative embodiments intended for in vitro use, a larger, less maneuverable tabletop version of the tool is contemplated in which constituent materials may be dispensed through multiple, discrete dispensing heads. Tabletop embodiments may also be utilized to perform all of the same biological, tissue-engineering, and medical-process applications using the same constituent printing materials as the in vivo embodiments described herein. Thus, all embodiments disclosed herein for application in vivo may suitably be adapted for in vitro use and for tabletop settings. Similarly, embodiments disclosed herein for in vitro application may also be used or adapted for use in vivo. The described embodiments are not to be viewed as limited to either in vivo or in vitro usage.

DWDT and HAT specifically for tabletop processes or in vivo and in vitro medical processes are unique in at least four aspects: First, in some embodiments, the DWDT/HAT may include an imaging device 500, a detector 600, and a location control device 800 that permits navigation among internal cavities, and structural elements such as bones, muscles, tendons, mucosal layers, nerve channels, as well as arteries and veins, within the body. Additionally, an optional material remover 300 allows the disposal of tissue or fluids removed or cut from the target area, and an optional temperature controller 400 enables the user to heat or cool materials dispensed through the tool or elements within the tool itself. An optional apparatus stabilizer 900 allows positional control of the tool with respect to the target area. The optional detector 600 permits visualization through various spectroscopies including laser-induced fluorescence (LIF), time-resolved LIF, infrared (IR), Raman scattering, ultrasound, optical coherence tomography (OCT); and/or terahertz imaging interrogation to distinguish healthy and diseased tissues; and an optional therapeutic emitter 700 enabling therapies such as low-energy photon therapy (LEPT). Furthermore, prior generated imaging processes such as magnetic resonance imaging (MRI) or thin-film histology may be used in concourse with the HAT.

Second, the DWDT/HAT has the ability to add desirable and/or subtract unwanted tissues and materials in a seamless and facile fashion. In one embodiment, the apparatus may perform subtractive processes using a material destroyer 200, which in one embodiment comprises a USP-laser-based system that replaces the cutting tools in a traditional orthoscopic tool. The laser system may be equipped with USP or long-pulse (LP) capability, combinations thereof, or a pulse duration ($\tau_p$) within the LP-USP cusp region (1-300 ps). This permits the apparatus to trim, to shape, and to remove tissue in the damaged or construction region in either a thermal or an a thermal manner, with the a thermal process not damaging such surrounding materials as tissue.

Third, in some embodiments the DWDT/HAT combines the fabrication and assembly processes. For example, DWDT/HAT may include a material dispenser 100 that facilitates the fabrication and assembly of biocompatible scaffolds, cells, nutrients, growth factors, ECM proteins, therapeutics, and other biological, organic, or inorganic components as desired to form various components, such as 3D engineered tissue constructs (ETC).

Fourth, the DWDT/HAT allows the processes to be performed both outside and within the body.

In some embodiments, the HAT device for in vivo use is similar in visual appearance to existing MIS devices. HAT can image, add, and subtract, in vivo, a wide range of materials with reproducible precision. The precise 3D in vivo direct deposition of cells, bioactive factors, and supportive 3D scaffolding using the miniaturized dispensing nozzle deposition system may help harness the potential of modern biology to deliver therapeutic regenerative medicine. The ability to precisely and selectively add, in real time, supportive 3D matrices, bioactive factors, and cells that differentiate and grow brings about a new-to-the-world advance to the metabolic- and tissue-engineering communities. It also enables medical procedures intended to repair, replace, rebuild, and/or reactivate tissue with minimized trauma to the human and/or animal body. The HAT device and methods enable the precise in vivo placement and microenvironment control of cells with high proliferative capacities and specified differentiation.

A goal of molecular medicine is to channel multipotent human cells with high proliferative capacities into specified differentiation programs within the body. This goal may be achieved by leveraging the biological knowledge of the importance of three-dimensionality and cell microenvironment to achieve normal tissue morphogenesis, vascularization, and organ functions. A multitude of therapeutic uses can be envisioned. Among these are the in situ generation of different types of neurons for treatment of Alzheimer's disease, spinal cord injuries, or Parkinson's disease; the production of heart muscles for congenital heart disorders or for heart-attack victims; the generation of insulin-secreting pancreatic islet cells for treatment of certain types of diabetes; or even the generation of dermal papilla or hair-follicle stem cells for the treatment of certain types of baldness. Ultimately, it may be possible to move beyond the generation of specialized cell types to entire organs. In some embodiments, the same basic tool may be used for all of the aforementioned procedures.

Currently contemplated applications for 3D engineered tissue constructs include cartilage, skin, and bone tissue replacements. Other applications include islets of Langerhans, which form the endocrine portion of the human pancreas. The differences in the applications revolve around the level of difficulty in the biomedical aspect of the tool, the need for vascularization, and the medical procedures.

Culturally, MIS procedures have been widely adopted for orthopedics, changing some knee replacement and reconstruction operations from a hospital stay of up to three days, to deal with trauma induced to the body, to half-day outpatient procedures. DWDT/HAT technology can further improve these procedures and provide a true cure.

Indeed, the burdens to the patient and the health-care delivery system arising from the extensive surgery often required and the high number of repeat procedures are no longer in line with the objectives of today's treatment preferences. Mechanical devices, such as kidney dialysis machines, continue to provide important therapeutic functions but fall short of the mark of real curative medicine. One illustrative example is the treatment of diabetes with islet-cell transplants from donors. Currently, islet cells are obtained from the pancreases of cadavers. For the process to be successful, it requires two donors that have similar genetic structures to the patient. The extraction and delivery process damages the viability of the cells, creating a requirement to use two pancreases from different donors to obtain sufficient islet cells to grow and take over the function of the original pancreases. Multiple donors significantly complicate the medical procedure, and then force the patient into a lifetime regimen of immunosuppressive medication and therapy. This procedure has resulted in a true cure for diabetes, but lifetime use of immunosuppression has its own medical side effects that reduce the patient's lifetime and quality of life. DWDT/HAT, in some embodiments, precisely delivers and controls the in vivo microenvironment and vascularized network of the cellular construct in a MIS-compatible manner, and can provide a suitable setting for islet cells to proliferate and regenerate, enabling a complete cure for diabetes with minimal trauma.

Tissue engineering uses tissue-specific cells and growth factors in a 3D organization, provided by the scaffolding material, to return partial functionality to a damaged organ. Many factors are considered in tissue engineering. The 3D structure is an important component of engineered tissue development as discussed in further detail below. Yanas and Burke have shown that pore size, pore orientation, and fiber structure are important characteristics in the design of cell scaffolds. See I. V. Yannas and J. F. Burke, *Journal of Biomedical Materials Research* 1980, 14, 65, which is expressly incorporated herein in its entirety by this reference. Another strategy involves the use of polymer-cell constructs composed of stem cells seeded into a porous, biodegradable polymer scaffold. The transplanted cells may secrete a new matrix and other factors necessary for tissue growth, and as the transplanted cells grow into a structure, the polymer matrix gradually degrades. See S. L. Ishaug-Riley, G. M. Crane, A. Gurlek, M. J. Miller, A. W. Yasko, M. J. Yaszemski, and A. G. Mikos, *Journal of Biomedical Materials Research* 1997, 36, 1, which is expressly incorporated herein in its entirety by this reference.

The choice of scaffolding material can significantly affect the outcome of the transplantation. The scaffold material has many traditional requirements, including biocompatibility, biodegradability into nontoxic degradation byproducts, ready availability, ready conformability to the size and shape of the defect, and pore volume. In addition to the traditional scaffolding requirements, because the cells and scaffolding matrix can be deposited by the DWDT/HAT simultaneously, the scaffolding matrix precursors should not be cytotoxic.

In particular, for in vivo applications, the choice of the scaffolding material bears on the success of the technique. The reason is that many common scaffold materials use organic solvents and/or processing conditions that are not amenable to in vivo use. For example, poly(lactic acid), poly (glycolic acid), and their copolymers are suitable for many tissue-engineering applications in a prefabricated form. However, they cannot be used as injectable in situ-forming materials because they are very hydrophobic and require the use of an organic solvent or heat for processing. See A. G. Mikos and J. S. Temenoff, *Electronic Journal of Biotechnology* 2000, 3 (2), http://www.ejb.org/content/vol3/issue2/full5/index.html; accessed Jun. 11, 2002, which is expressly incorporated herein in its entirety by this reference.

Some of the material introduced with the DWDT/HAT may advantageously be formed in situ. Some of these materials are in situ polymerizable (crosslinkable) materials. They may be monomers or unsaturated polymers. They can polymerize by chemical initiation or by photoinitiation. Acceptable materials for use with the DWDT/HAT include unsaturated polyesters such as poly(propylene fumarate)(PPF) and its copolymers developed at Rice University. They can produce materials with tailored mechanical, degradative, and biological properties required for specific applications serving as delivery vehicles for cells and bioactive molecules, including proteins and deoxyribonucleic acid (DNA). They can further serve as carriers for microparticles and nanoparticles for controlled release of antibiotics and biochemicals to modulate cell function and to induce tissue regeneration. See J. S. Temenoff and A. G. Mikos, *Biomaterials* 2000, 21, 2405, which is expressly incorporated herein in its entirety by this reference.

The identification of proper photoinitiators offering fast photo-crosslinking of polymers while simultaneously having low toxicity to cells and tissue components is an important issue. Most of the existing photoactivators were designed to be stimulated by ultraviolet (UV) light, which can be damaging to cell cultures. The identification and use of photoactivators sensitive to visible light could reduce those damaging effects. Moreover, the creation of an injectable engineered tissue construct leads to the idea of subsequent transdermal photopolymerization. See J. Elisseeff, K. Anseth, D. Sims, W. McIntosh, M. Randolph, and R. Langer, "Transdermal Photopolymerization for Minimally Invasive Implantation," *Proceedings of the National Academy of Sciences of the United States of America* 1999, 96 (6), 3104, which is expressly incorporated herein in its entirety by this reference. Visible, especially red, light penetrates skin more readily and with less loss; again, activators sensitive to visible light would be of considerable benefit. Currently, photoactivators are being selected from those used in the polymer and painting industries and in laboratory practice. Irgacure 819 and Irgacure 784 (both available from Ciba Chemicals), H-Nu 470 and H-Nu 635 (both available from Spectra Group Limited, Inc.), and Eosin Y (available from Sigma-Aldrich and other companies)

exemplify activators sensitive to both UV and visible radiation. Among them, only Irgacure 819 provides reliable activation in wide variety of conditions and in the presence of oxygen, but it is relatively toxic to cells.

Another factor with regard to scaffold materials is the proper balance of polymer scaffold degradation and tissue ingrowth. The polymer foam should be present for a sufficient time to allow construction of new tissue. After formation of new tissue, the scaffolding material is no longer needed; it can degrade. This attribute of controlled degradation can be achieved through a variety of techniques, including varying the monomer ratio and molecular weight of the polymer scaffold.

The porosity and the surface area are, in addition to the degradation rate, other important characteristics of the scaffold material. In order to promote tissue growth, the scaffold should have a large surface area to allow cell attachment. This can be achieved by creating highly porous polymer foams with pore sizes large enough so that cells penetrate the pores. Additionally, the pores may be interconnected to facilitate nutrient and waste exchange by cells deeper into the construct. The diversity of organ structure and function is such that the design requirements of scaffolds for tissue engineering may be specific to the tissue of interest.

Most scaffolds can be populated with adult-derived cells that are capable of undergoing subsequent differentiation after being cultivated in vitro. In this category are cells of skin, cartilage, muscle, tendon, ligament, bone, adipose tissue, endothelium, and many others. Aside from skin, the foregoing cell types are harbored as stem-cell populations in the marrow and fat, in addition to those of the hematopoietic and immune systems. Stimulating factors, the cytokines, which move some of the cells into circulation, can be important for engineering a cellular scaffold. Other stem cells are available for tissue engineering, such as embryonic stem cells, satellite cells found in striated muscle and, to some degree, keratinocytes of the skin. Where host cells are available, a cellular scaffold, particularly one enhanced with signals and possessing the binding sites needed for cell attachment, can mobilize host cells to populate the scaffold. Recently, new sources of stem cells, particularly neuronal stem cells, have been discovered in the adult brain. They are opening the door to the reconstruction of nerve tissue for tissue engineering.

The cell microenvironment is important to the fields of metabolic and tissue engineering. The DWDT/HAT apparatus and methods are an enabling technology platform for these communities. The engineered tissue construct initially discussed is cartilage, which has been considered an "ideal tissue to engineer." Some of the reasons for the elevated tissue status of cartilage include: Its regeneration is limited, it is comprised of one cell type, it has a low oxygen requirement (no vascularization is required), and it can be stored for relatively long periods. See H. J. Mankin, *Journal of Bone and Joint Surgery,* 1982, 64A, 460; G. Meachim, *Journal of Bone and Joint Surgery* 1963, 45B, 150; and, W. Bloom and D. W. Fawcett, in D. Dreibelbis, ed., *Bloom and Fawcett: A Textbook of Histology,* 10th Ed. (Philadelphia: W. B. Saunders Company, 1986), p. 188, which are expressly incorporated herein in their entirety by this reference.

In vitro cultures offer the possibility to induce chondrocyte proliferation using static Petri dishes, rotating bioreactors, and/or perfused vessels. A limitation with these two-dimensional (2D) approaches is dedifferentiation of the chondrocytes. In fact, it has been observed that the collagen switches from type II to type I in a 2D microenvironment. Type I acquires a fibroblast-like appearance and is associated with a change in the cell configuration. See A. L. Aulthouse, M. Beck, E. Griffey, J. Sandford, K. Arden, M. Machoado, and W. A. Horton, *In Vitro Cell Development and Biology* 1989, 25, 659; Y. Kato and D. Gospodarowicz, *Journal of Cell Biology* 1985, 100, 477; and H. Ramdi, C. Legay, and M. Lievremont, *Experimental Cell Research* 1993, 207, 449, which are expressly incorporated herein in their entirety by this reference.

On the in vivo front, several researchers have attempted to regenerate cartilage from isolated chondrocytes. Their success rates were not encouraging, because once the cells were delivered without an appropriate matrix they were simply dispersed into the surrounding tissue. For example, researchers found that the implanted chondrocytes under these conditions displayed irregular arrangements; likewise, the quality of the newly regenerated cartilage did not mimic the properties of the original tissue. See J. Kawiak, S. Moskalewski, and A. Hinek, *Acta Anatomical* 1970, 76, 530, which is expressly incorporated herein in its entirety by this reference.

Thus, in the past, low proliferation rates have typically been observed for the chondrocyte cells, with the major limiting factor being the appropriate matrix onto which to seed and shape the cells. Metabolic and tissue engineering enables the use of autologous cells and custom-designed synthetic biodegradable and bioresorbable scaffolding matrix to recreate the shape and size needed. See C. A. Vacanti, W. Kim, B. Scholl, J. Upton, and J. P. Vacanti, *American Journal of Sports Medicine* 1994, 22, 485 and A. M. Rodriguez and C. A. Vacanti, *Frontiers in Tissue Engineering* (New York: Elsevier, 1998), p. 400, which are expressly incorporated herein in their entirety by this reference. For example, 3D chondrocyte-polymer scaffold constructs lead to proper and healthy cartilage formation. The proper 3D microenvironment has enabled the chondrocytes to engraft and form cartilage. The engineered tissue also showed collagen type II content. Ancillary controls done by implanting the in vivo polymer without the chondrocyte cells formed no cartilage as would be expected. See C. A. Vacanti, R. Langer, B. Schloo, and J. P. Vacanti, *Plastic and Reconstructive Surgery* 1991, 88 (5), 753, which is expressly incorporated herein in its entirety by this reference.

Thus, despite the nonvascularized nature of cartilage, the proper 3D microenvironment improves cell formation and proliferation. Therefore, for vascularized tissue (e.g., but not limited to, bone, muscle, heart), the proper control of the 3D microenvironment is believed to be an important factor.

A factor for growing organ tissue in vitro or in vivo is that its thickness and complexity require that it be nourished by a 3D vascular network within the host organ. Vascularization, and the concomitant action of supplying oxygen and nutrients in addition to carrying off waste material, has been a barrier to the successful construction of large engineered tissue constructs. The survival of cells deep within the structure can be at risk. Tissues with dimensions much larger than ~1 mm therefore require, in some applications, the creation of new blood vessels for nutrient supply. The risk of mortality may be reduced, inter alia, by utilizing angiogenic cytokines and methods of tissue design that can promote development of adequate circulation with sufficient rapidity in vivo. However, with DWDT/HAT, the scaffolding provides a vehicle for the generation of vascularized structures. Previous researchers have relied on tissue diffusion to deliver oxygen and nutrients to cells grown in the laboratory. However, in general, this technique is not effective for thicker tissues or organs. All living systems rely on the mass transfer of oxygen and nutrition for maintenance and survival. At some critical point, relying on the open pores from the system and diffusion from the nearest source of oxygen and nutrition no longer works. While blood vessels can develop in thin tissues, many cells in thick tissues die before there is sufficient ingrowth to support them. It is possible that proper vascularized networks will only be realized in vivo.

Tissues in the body overcome issues of mass transport by containing closely spaced capillaries that provide conduits for convective transport of nutrients and waste products to and from the tissues. It is similarly considered advantageous for any engineered tissue construct of significant size to become vascularized.

At least four approaches are contemplated by which to promote vascularization of engineered tissue construct. First, scaffolds utilized for cell transplantation may be designed to promote invasion of host fibrovascular tissue by the inclusion of large, interconnected pores.

The second, more active, approach to promote vascularization of engineered tissue construct is the delivery of angiogenic growth factors to the implant site. D. J. Mooney and A. G. Mikos, "Growing New Organs," *Scientific American*, http://www.sciam.com/article.cfm?articleID=00032414-5E8D-1C70-84A9809EC588EF21&catID=2, April 1999, accessed Jun. 11, 2002, which is expressly incorporated herein in its entirety by this reference. Growth factors are polypeptides that transmit signals to modulate cellular activities. Growth factors can either stimulate or inhibit cell proliferation, differentiation, migration, adhesion, and gene expression. Experiments have demonstrated that these factors may be directly included within the tissue engineering scaffolds for a sustained delivery at the desired site. Many angiogenetic factors, such as vascular endothelial growth factor (VEGF), fibroblast growth factor (FGF), platelet-derived growth factor (PDGF), and others are now commercially available; trials are being conducted to test them as potential treatments for arterial blockages and related conditions. See MicroHeart, Inc., http://www.microheart.com/01tech02.htm, 1999-2000, accessed Jun. 11, 2002 and T. D. Henry, BMJ 1999, 318, 1536; http://www.bmj.com/cgi/content/full/318/7197/1536, accessed Jun. 11, 2002, which are expressly incorporated herein in their entirety by this reference.

Despite good progress regarding growth factors, some issues remain. For instance, many have short half-lives, are relatively large, and exhibit slow tissue penetration, therefore novel means can be required to administer them. See J. E. Babensee, L. V. McIntire, and A. G. Mikos, *Pharmaceutical Research* 2000, 17, 5, which is expressly incorporated herein in its entirety by this reference. One such way to enhance the in vivo efficacy of growth factors is to facilitate the sustained release of bioactive molecules over an extended time by their incorporation into the polymer carrier. See H. Lo, S. Kadiyala, S. E. Guggino, and K. W. Leong, *Journal of Biomedical Materials Research* 1996, 30, 475, which is expressly incorporated herein in its entirety by this reference. Through incorporation into the scaffold material during deposition, protein structure—and thus biological activity—can be stabilized, prolonging the length of time over which activity is released at the delivery site. In a biodegradable system, the growth factor used to induce tissue regeneration would be directly incorporated into a bioresorbable polymer scaffold and released by a diffusion-controlled mechanism, regulated by the scaffold architecture and its degradation.

The efforts to regenerate tissues in model systems to date (e.g., bone, blood vessels) have typically relied on the delivery of a single growth factor. However, Mooney et al. reported a new polymeric system of two growth factors, with controlled dose and rate of delivery for therapeutic angiogenesis. See T. P. Richardson, M. C. Peters, A. B. Ennett, and D. J. Mooney, *Nature Biotechnology* 2001, 19, 1029, which is expressly incorporated herein in its entirety by this reference. They found that the dual delivery of VEGF-165 and PDGF-BB, each with distinct kinetics, results in the rapid formation of a mature vascular network. It is believed that this work is the first report of the delivery of multiple angiogenic factors that led to improved action in tissue regeneration and engineering. DWDT/HAT enables the fabrication of layers with multiple materials via multiple miniaturized dispensing nozzles and the building of different configurations that can come about via layer-by-layer (z-direction) growth along with controlled gradients in the xy plane.

A third approach is to enhance angiogenesis in an engineered tissue construct by co-transplanting endothelial cells along with the primary cell type of interest. See D. J. Mooney and A. G. Mikos, "Growing New Organs," *Scientific American*, http://www.sciam.com/article.cfm?articleID=00032414-5E8D-1C70-84A9809EC588EF21&catID=2, April 1999, accessed Jun. 11, 2002, which is expressly incorporated herein in its entirety by this reference. The endothelial cells seeded into an engineered tissue construct scaffold form capillaries that can merge with the capillaries growing into the scaffold from the host tissue.

A fourth approach is to construct a network of channels for vascularization within and around the periphery of the scaffold. In various embodiments, these channels could be built into the scaffold during the layer-by-layer deposition process, ablated with a laser, or formed by other means. Notably, the scaffold pores may be randomly distributed and oriented. The replacement of pores with ordered channels may further boost the performance of tissue scaffolding. The channels may be placed in a two-layer "log cage" scaffold constructed of biodegradable PPF, in which 100-µm-diameter wire probes have been inserted to emphasize the open channels.

Building a "log cage" or a "log cabin" from a biodegradable material, such as medical plastic or hydrogel polymer, is a possible pathway to achieve better-organized artificial tissue. The "logs" should be sufficiently flexible and adhesive at the time of deposition onto a supporting slide, yet hard and rigid enough not to hang down into "channels" of the underlying row and clog them. In one embodiment, focused photopolymerization of the plastic "log" may be used during the deposition process, with fiber light-guides properly oriented with respect to dispensing nozzles to provide "illumination on the fly" and "illumination after deposition" modes, as discussed in more detail below. Another option is to fill the channels temporarily with a soluble or degradable "stuffing."

Possibilities include concentrated solutions of carbohydrates (e.g., honey), poly(ethylene glycol)(PEG), or a biological hydrogel. The "stuffing" can play both support and functional roles if, for example, it also contains growth factors, nutrients and/or seeding cells. As discussed below, the DWDT/HAT in vivo can employ multiple dispensing nozzles to mix cells, growth factors, and polymer scaffold materials in a spatially controlled way, or they can be commixed in the fluid reservoir. The DWDT/HAT enables new scaffolding architectures to be fabricated that could not be formed otherwise. Such architectures include the "log cabin" discussed above as well as others with multiple pore sizes, which may be optimal for engineered tissue construct. Larger ones likely enable mass transfer (e.g., of growth factors to grow and proliferate cells or aid angiogenesis), while smaller ones enable cell and/or growth factor adhesion to the construct. Likewise, the laser capability in DWDT/HAT can be used to ablate channels for vascularization into the scaffold.

In vivo studies show that nearly any cell type in the "right" supportive microenvironment can demonstrate profound growth capacity and full restoration of differentiation specific to the founder cell. Further, accumulating evidence shows "terminally differentiated" adult cells to have the capacity to be a source for retrodifferentiation to bipotential, pluripotential, or totipotential stem-cell populations that can give rise to seemingly unrelated tissues. In other words, developmental biology is highly plastic and multidirectional, provided the micro- and macroenvironments support and drive it. Therefore, in some embodiments of the invention, it is important to recreate the three-dimensional microenvironment needed to support the normal range of in vivo cell functions.

An attribute of the DWDT/HAT device and methods, in some embodiments, is that biocompatible materials may be constructed that replicate and possess a large number of characteristics of the natural matrix (e.g., 3D microenvironment, vascularization), but are capable of facile manufacture and customization in vivo.

The DWDT/HAT technology has a plurality of aspects that, in some embodiments, combine to make a tool capable of producing a modeled structure through 3D direct construction of various materials into complex shapes. The DWDT/HAT technologies are now discussed in detail. Referring now to the drawings (FIGS. 2A-2F, 4-7, 10, 34 and 36) the DWDT/HAT includes a material dispenser 100 for performing additive procedures by which constructs, such as engineered tissue constructs, are made from a wide range of constituent materials; a material destroyer 200 for performing subtractive procedures, such as laser-ablation; a material remover 300 for suctioning or other removal of unwanted materials; temperature controllers 400, such as heating and cooling systems; vision and imaging devices 500, such as cameras; detection devices 600, for performing processes such as optical coherence tomography infrared spectroscopy, Raman scattering, and LIF detection; therapeutic emitters 700 for performing processes such as photon therapy; location control devices 800, such as robotic manipulation systems; and stabilization devices 900, such as guides and stabilizers for the apparatus. Accordingly, the DWDT/HAT technologies provide both a unique tool and a system design, and also include the use of the several embodiments of the technologies as an integrated apparatus or tool.

Figure 2C:
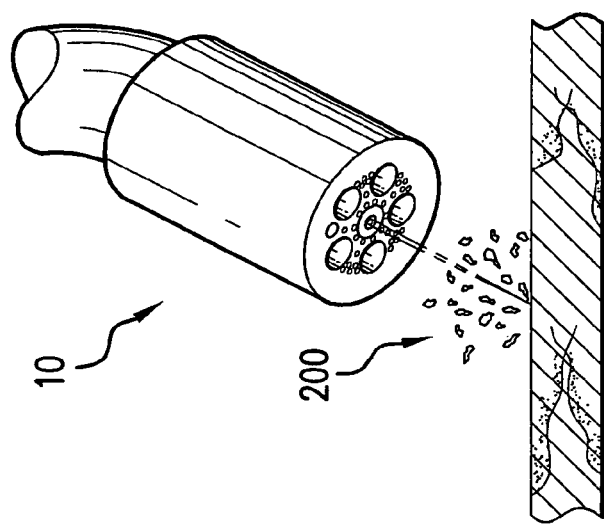
FIGS. 2A-2F are a series of perspective views of embodiments of the invention for in vivo use.
Figure 2B:
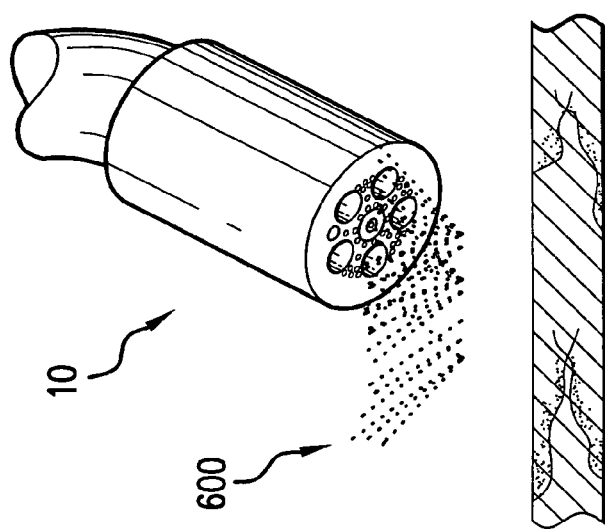
Figure 2A:
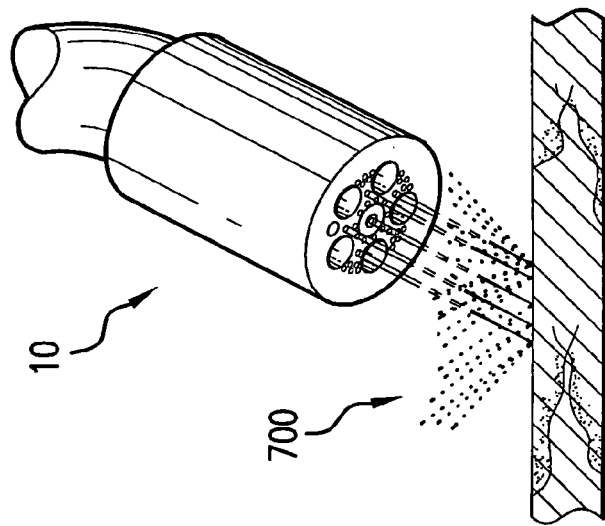
Figure 2F:
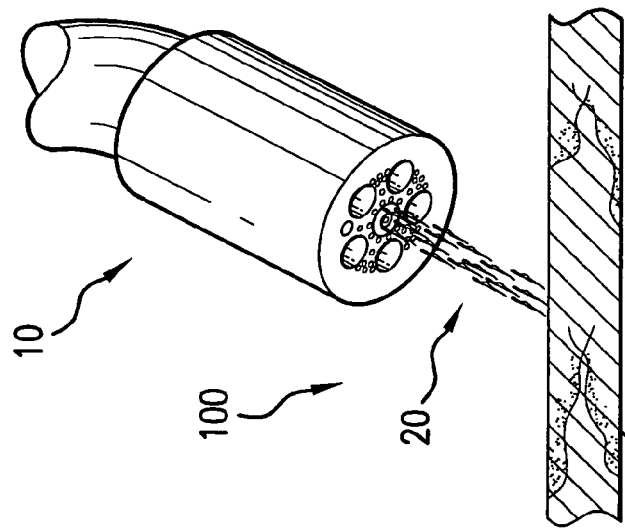
Figure 2E:
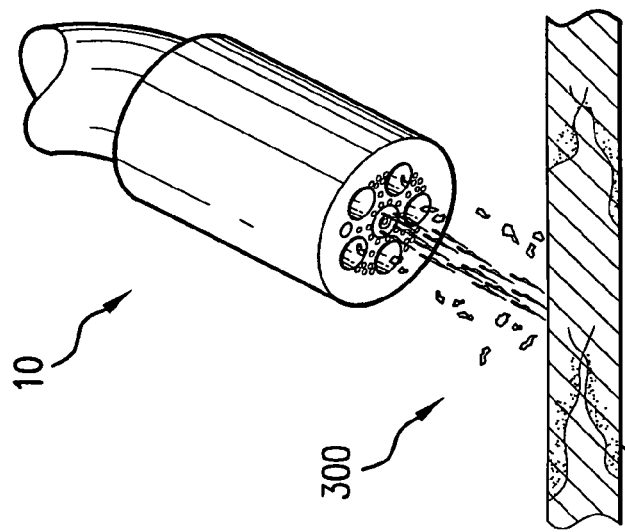
Figure 2D:
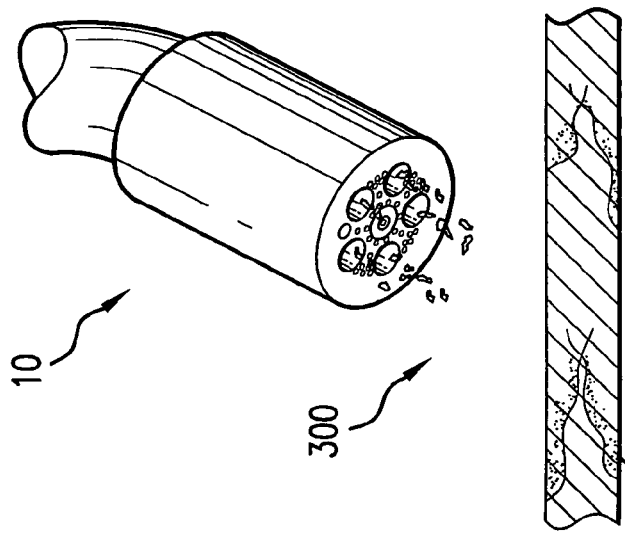
Figure 3:
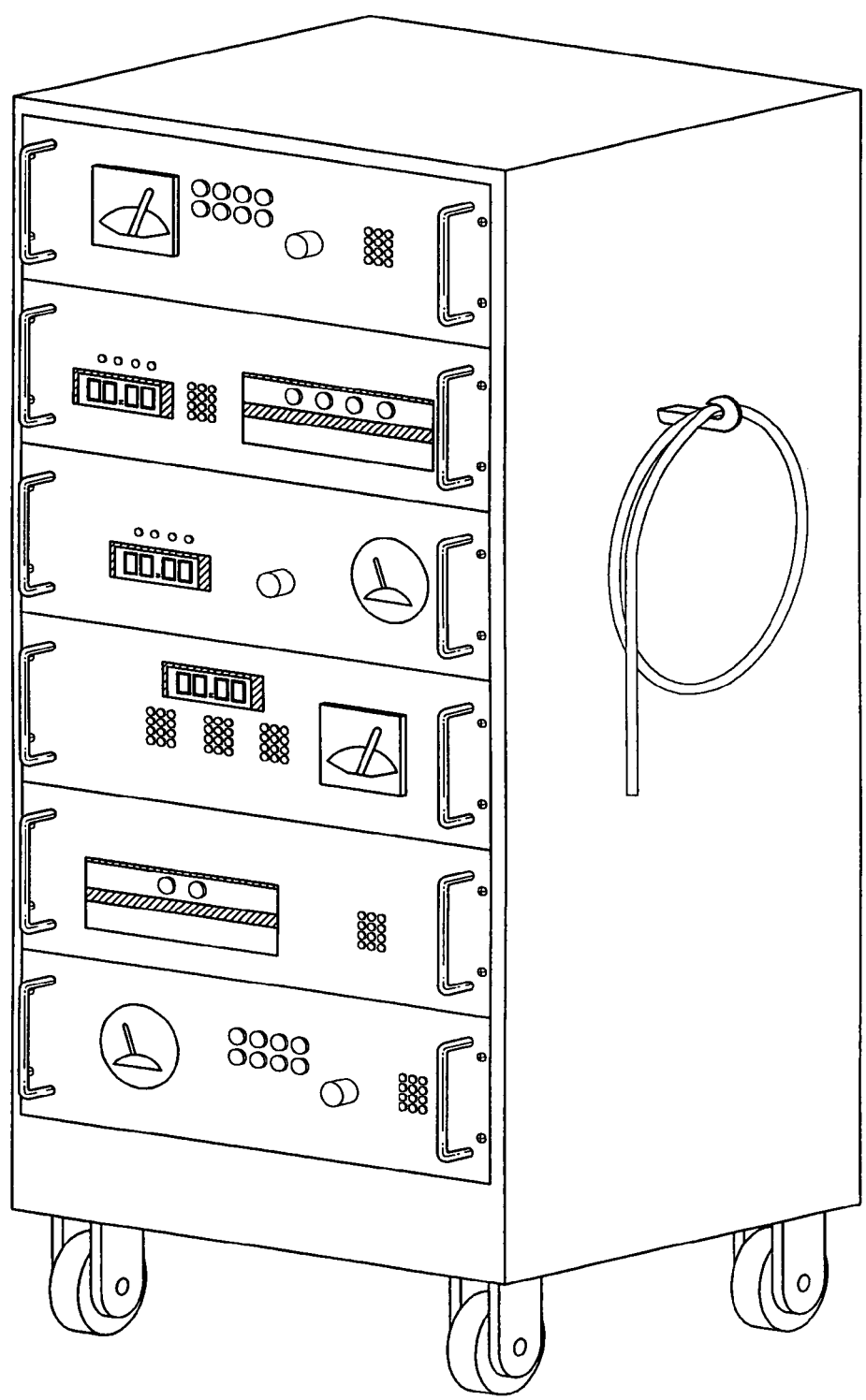
FIG. 3 is a perspective view of a cart carrying support components of the invention.

Illustrations of several MIS-compatible embodiments of the invention are set forth in FIGS. 2A-2F, and one embodiment of an associated table or medical cart for the surgical suite is set forth in FIG. 3. The system includes the necessary power supplies, delivery mechanisms, laser, and computer to control the tool. An umbilical cord is connected to the system that can be handheld by a surgeon or controlled via robotics.

Detection and Imaging Technologies

The ability to distinguish healthy from unhealthy tissue while providing control feedback to the laser system is provided in some surgical embodiments to provide information to the surgeon about where to begin and where to end the procedure. Several imaging techniques can be incorporated into the DWDT/HAT system, including but not limited to fiber-based integrated detection schemes such as LIF, time-resolved LIF, Raman and IR spectroscopies, and optical coherence tomography (OCT), as desired.

The capability to reliably visualize and distinguish normal and pathological tissue may be compared to driving at night-without headlights. Even on familiar roads, driving blind is dangerous and slow. As one example, many groups have worked on related techniques to detect accurately cancerous cells.

Figure 4:
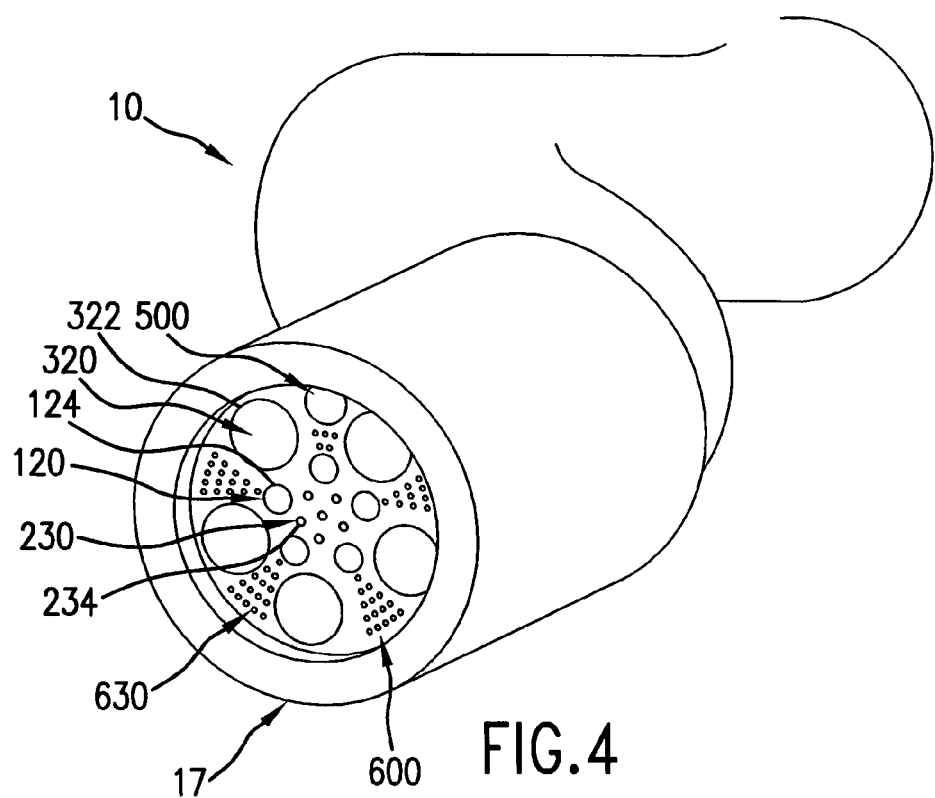
FIG. 4 is a perspective view of an embodiment of the invention for in vivo use.

Imaging and detection techniques may be integrated in the embodiments of the DWDT/HAT device and methods. Referring now to FIG. 4, in some embodiments, the apparatus 10 may include one or more detectors 600. In one embodiment, the detector 600 is an optical fiber based detector. Such embodiments may be integrated with an endoscope for real-time observation and detection of differing tissues both in the plane of the tissue as well as into the tissue (OCT).

As one example, some of the optical fibers 230 may be sources for laser output and may include a white-light output for the endoscope. A light collector 630, which is an optical fiber in the illustrated embodiment, may be used to detect fluorescence signals induced by relatively weak UV laser pulses and emitted either immediately by natural tissue fluorophores (autofluorescence (AF)) or by special fluorophoric markers selectively absorbed by normal or pathologic tissues (exogenous fluorescence (EF)). See F. Koenig, F. J. McGovern, A. F. Althausen, T. F. Deutsch, and K. T. Schomacker, *Journal of Urology* 1996, 5, 1597; J. Hung, S. Lam, J. LeRiche, and B. Palcic, *Lasers in Surgery and Medicine* 1991, 11, 99; G. Zonios, R. M. Cothren, J. Arendt, J. Wu, J. M. Crawford, J. Van Dam, R. Manoharan, and M. S. Feld, *Proceedings of SPIE* 1994, 2324, 9; N. Ramanujam, *Neoplasia* 2000, 2 (1-2), 89; Y. Kusunoki, F. Imamura, H. Uda, M. Mano, and T. Horai, *Chest* 2000, 118 (6), 1776; and A. Leunig, C. S. Betz, M. Mehlmann, H. Stepp, S. Abrogast, G. Grevers, and R. Baumgartner, *Laryngoscope* 2000, 110 (1), 78, which are expressly incorporated herein in their entirety by this reference.

Figure 5:
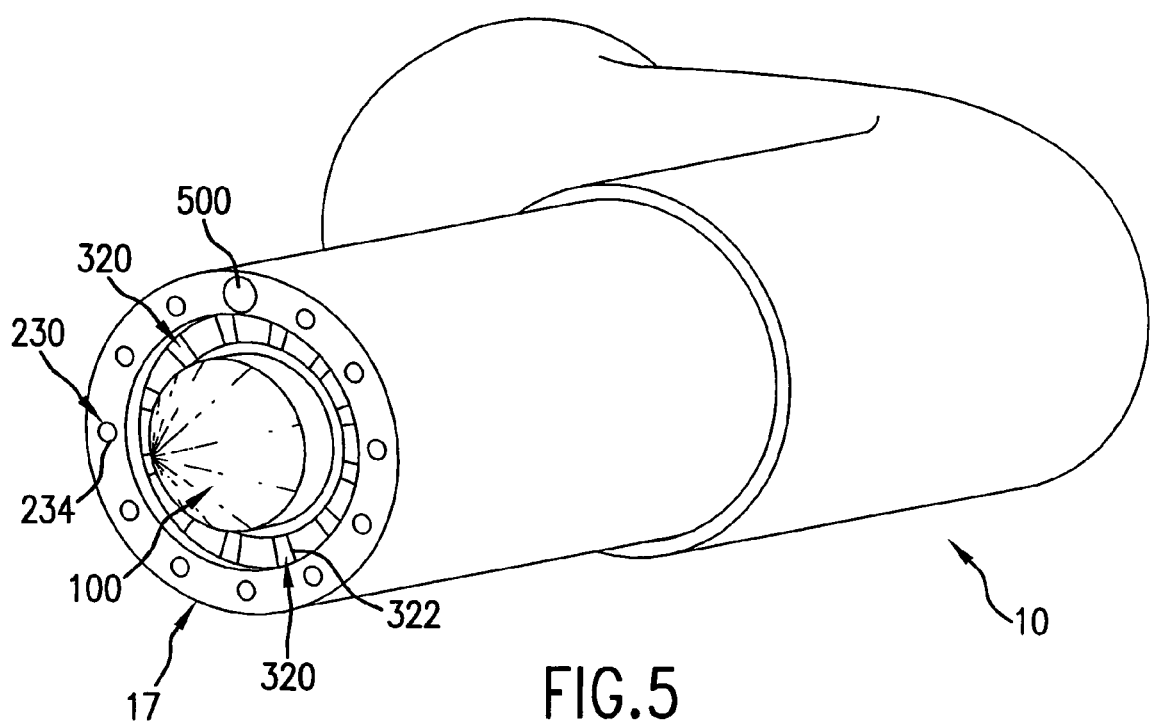
FIG. 5 is a perspective view of another embodiment of the invention for in vivo use.

Other embodiments of the DWDT/HAT device, such as that shown in FIG. 5, use a dual use optical fiber 230 for multiple processes, as many imaging and vision processes are in the visible to near-IR regimes. In some embodiments, the tip end 17 of the tool, which is the portion to be inserted in a MIS procedure, is from about 7 to 10 mm in diameter.

Figures 6A, 6B:
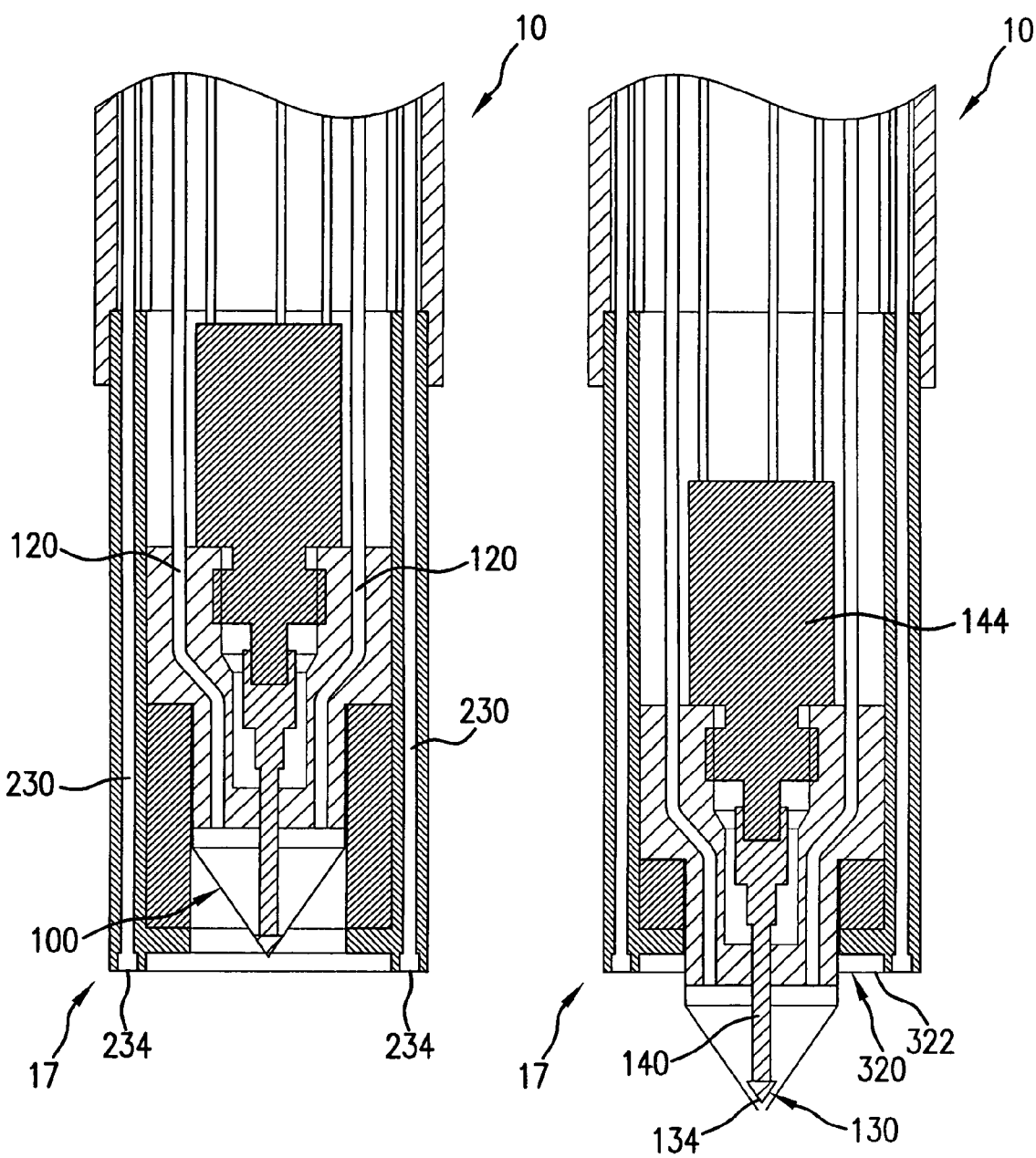
FIGS. 6A and 6B are cross sectional side views of the embodiment of FIG. 5 showing extension and retraction of the material dispenser.
Figure 7:
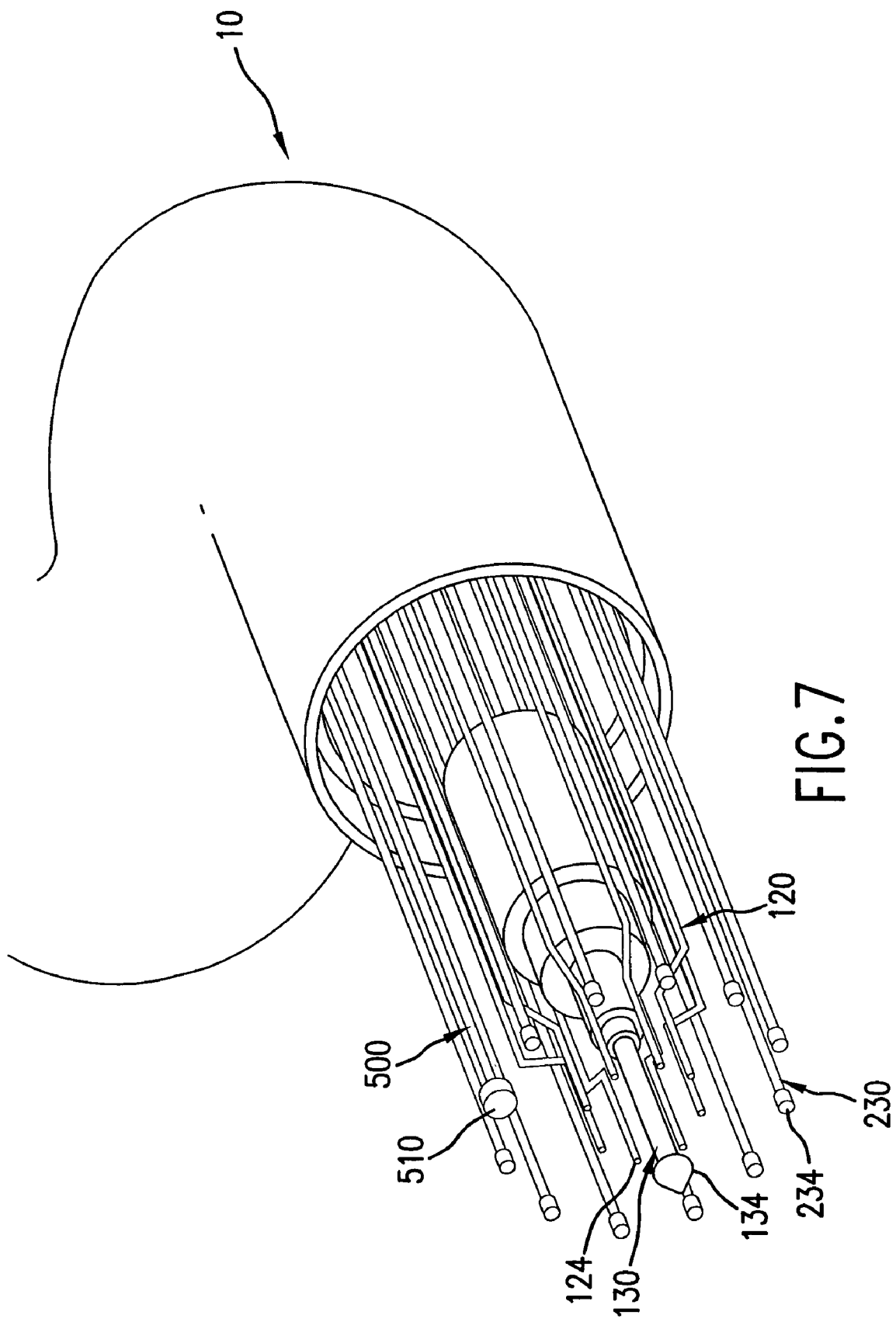
FIG. 7 is a perspective view of an embodiment of the embodiment of FIG. 5 with components stripped away to show certain internal structures.

FIGS. 5-7 illustrate an embodiment of the device having a tip end 17 comparable to that shown in FIG. 4 but featuring dual-use optical fibers 230 and a retractable tapered material dispenser 100, the cover 42 (FIG. 5) of which can be constructed of any suitable material, including metals and hydrophobic plastics.

Various embodiments of the invention allow for a variety of light sources to be coupled into the laser-emitting fibers for enhanced data, producing such results as reflection and fluorescence signatures to be used in the analysis routine.

Infrared (IR) Imaging/Detection

In one embodiment, the invention is a tool 10 (e.g., FIG. 2B) that includes a means for performing infrared spectroscopy to collect diagnostic information from tissue at a target area or a substrate 22. While guiding light is a well-understood phenomenon, certain applications may be enhanced by utilizing advanced fibers, materials, and techniques for success. The use of endoscopes to provide imaging of diseased tissues is described in various patents (e.g., U.S. Pat. Nos. 5,507,287, 5,827,190, 5,840,017, 6,364,829, 6,364,831, 6,377,842, 5,921,916, and 5,984,861, which are expressly incorporated herein in their entirety by this reference). Near-IR radiation can be coupled into and propagate within a typical silica ($SiO_2$) fiber. However, for longer wavelengths ($\lambda$), these fibers are not effective. Hollow stainless-steel tubes and zinc selenide (ZnSe) fibers are used to guide the 10.6-µm radiation typical of carbon dioxide ($CO_2$) lasers.

A material recently developed by J. Simmons and colleagues of the University of Arizona (UA) has proven to be effective for the IR regime. This is useful in certain embodiments of the present invention, because this spectral regime is that used for Fourier-transform infrared (FTIR) spectroscopy.

The inclusion of FTIR capabilities allows certain embodiments of the DWDT/HAT to perform elemental analyses via a fiber delivery system. The use of optical spectroscopy to determine surface reactions of cells for diagnostic purposes is very attractive due to the nondestructive nature of the tests and the possibility of conducting them in real time and in situ through a fiber-optic probe. This broad IR window makes possible conducting FTIR spectroscopy through a fiber probe. The combination of the new analytical method with IR-transmitting fibers makes possible remote sensing of cellular surface composition and structure by IR reflection spectroscopy. The method is sensitive to the surface layer to a depth of about 0.1 μm. A concern in application of this method to biological systems is the presence of water, which absorbs strongly in the IR (e.g., a broad band centered near 3,600 cm$^1$ or 2.8 μm).

A two-pronged approach to remote IR analysis of cellular surfaces comprises (1) deconvoluting the water signal and (2) focusing on the spectrum away from the water lines. In the first, the results of research at UA, which show that Kramer-Kronig analysis allows the clear identification of absorption lines in the IR for each chemical species studied, can be used. See S. A. MacDonald, C. R. Schardt, D. J. Masiello, and J. H. Simmons, "Dispersion Analysis of FTIR Reflection Measurements in Silicate Glasses," *Journal of Non-Crystalline Solids* 2000, 275, 72, which is expressly incorporated herein in its entirety by this reference. This allows the subtraction of the water signal from the analyzed data to reveal the underlying spectral features of other components. A second approach is to conduct in vitro tests of typical cellular structures to determine the presence of characteristic line shapes.

These tests can lead to a design for a fiber-optic sensor for the chemical reactions taking place in situ on cellular surfaces. This sensor can be used to determine differences between diseased and healthy cells and to diagnose other cellular malfunctions, such as cancer.

Laser-Induced Fluorescence (LIF)

In another embodiment, the invention is a tool 10 (e.g., FIG. 2B) that includes a means for performing laser-induced fluorescence (LIF) to collect diagnostic information from tissue at the target area 22. The LIF method may be utilized in the present invention to extract unique signatures from diverse cells. LIF methods include examining the fluorescent light emitted upon stimulation of the tissue by a relatively weak laser—i.e., its irradiance or power density (H) value is low—that does not ablate, it only probes.

Minimum laser fluence depends on quantum yield of the fluorescence material, fluorescence detector sensitivity, and fluorescence measurement technique (imaging, time resolved fluorescence emission spectra etc.)

For example
1. Ti:Sapphire with amplifier-1 μJ pulses 10 ps duration at 5 KHz at 415 nm, using an intensified CCD as the detector.
2. Nitrogen laser 3 ns, 10 Hz, 337 nm, 0.6 μJ pulses, microchannel plate photomultiplier as the detector.

To be safe, typical fluences for LIF applications are in the range of 1 μJ/mm$^2$ to 1 mJ/mm$^2$; much less than the ablation threshold no matter what pulse width is used.

In one such embodiment shown in FIGS. 5-7, the tool 10 includes a tip end 17 and a spaced back end (not shown). The detector 600 includes a laser source (not shown) for supplying energy used in the detection process. At least one fiber 230 is included for carrying the laser light, having a remote end (not shown) operatively coupled to the laser source and a spaced emitting end 234 adjacent the tip end 17 of the tool. The detector also includes a light collector 630 for examining fluorescent light emitted from tissue at the target area.

The detection process can distinguish variations in spectral features, chiefly fluorescence wavelength ($\lambda_f$) and decay duration ($\tau_f$), between normal and malignant tissues. Applications of LIF to cancer diagnosis have previously been demonstrated, as have in vivo applications over limited areas of the body. Specifically, the fluorescence of a malignant esophageal tumor is less intense than that of healthy tissue. See T. Vo-Dinh, M. Panjehpour, and B. F. Overholt, *Annals of the New York Academy of Sciences* 1998, 838, 116. However, differentiation between normal tissue and pathological regions is often difficult, since the desired differential can be masked by variations in signal intensity, by measurement noise, or by numerous physiological factors. This capability can create a powerful diagnostic tool for identifying cancerous regions in MIS procedures.

Multiple sources and routes of detection provide a more accurate method of quantification, which is one of the major reasons justifying the diverse approach to light delivery in both ways.

Computerized Tomography (CT)

The DWDT/HAT also provides the ability to perform diagnostics via computerized tomography (CT). As known, a CT scan is a procedure that uses a computer to combine many X-ray or laser images into cross-sectional views of the internal organs of the body. CT scans are commonly used to image both normal and abnormal structures and can be used to help guide the placement of instruments or treatments.

For CT scans in the HAT, the laser beam sweeps three hundred sixty (360) degrees around the internal tissue or organ, or the external body part to be imaged. The image is obtained by comparing the energy that is absorbed at various angles about the outside of the object. The data is acquired by the fiber optical light emitter of the DWDT/HAT MIS-compatible head, where the tissue can be reconstructed into 3D cross-sectional images. These views are used to create a rotatable 3D image of the tissue and are able to probe 2-3 mm into the tissue.

These images are processed by computer algorithms and the resulting images appear as slices taken through the tissue. Techniques are now available that enable slices to be summed as a whole to replicate a 3D picture of the tissue or organ.

The tunable and intense IR pulse generation, compact high-power laser systems, "plug-and-play" femtosecond-regime (FSR) pulsed light sources, and the ability to couple a wide range of laser pulses (including USP's) through optical fibers have important applications for 3D imaging or tomography in the HAT. The MIS-compatible HAT enables the ability to perform CT imaging either in vitro or in vivo. Furthermore, the laser diode system (discussed later) in the HAT can be used for CT and ablation purposes in the same tool format.

Optical Coherence Tomography

Figure 35:
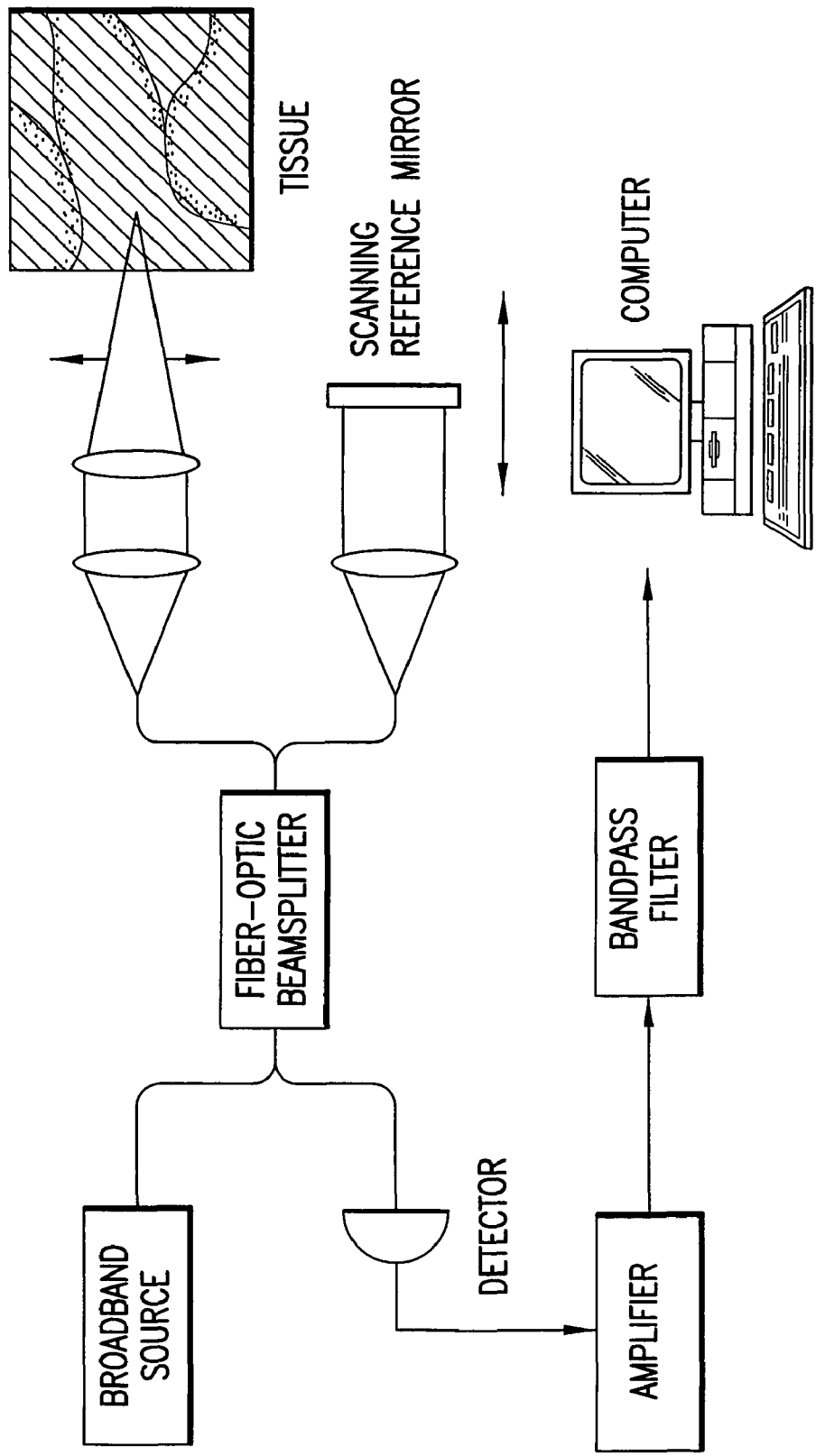
FIG. 35 is a schematic illustration of a devices and methods for performing optical coherence tomography of the invention.
Figure 36:
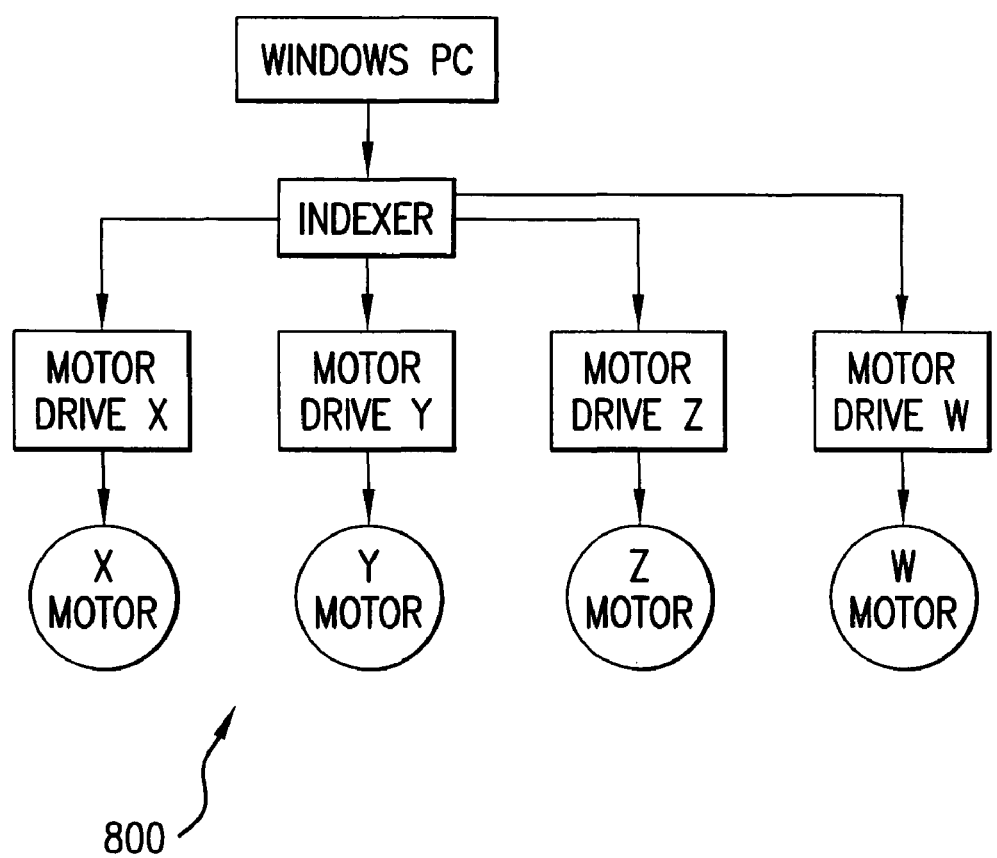
FIG. 36 is a schematic illustration of devices and methods for controlling and synchronizing the position of the material dispenser and the position of the valve within the material dispenser of the invention.

In another embodiment, the invention is a tool 10 (e.g., FIG. 2B) that includes a means for performing optical coherence tomography (OCT) to collect diagnostic information from tissue at the target area 22. OCT is an interferometric imaging technique that can provide detailed three-dimensional views of the subsurface microstructures of biological tissue. In separate embodiments, OCT may be incorporated in the tool 10 to provide both user observation and closed loop feedback control for other HAT processes. A block diagram of a standard OCT system is illustrated in FIG. 35.

In one embodiment in which the detector 600 is a means for performing OCT, the detector includes a laser source (not shown) for supplying energy used in the detection process. At least one optical fiber 230 is included for carrying the laser light, having a remote end (not shown) operatively coupled to the laser source and a spaced emitting end 234 adjacent the tip end 17 of the tool. The detector also includes a light collector 630 for examining fluorescent light emitted from tissue at the target area. The laser source may be a broadband light source, and the optical fiber 230 may include scanning optics and a fiber-optic beamsplitter (which may also act as an interferometer). A detector/signal processing section may also be provided for analyzing information collected by the light collector 630.

The broadband light source provides the optical "probe" that allows imaging into biological tissue. The scanning optics have two components: a scanning reference mirror that controls the z-axis depth of view and a lateral scanning mechanism that provides x-y positional control. A variety of scanning architectures are available for OCT that can optimize the system for a variety of desired parameters. See J. M. Schmitt, "Optical Coherence Tomography (OCT): A Review," IEEE Journal of Selected Topics in Quantum Electronics, vol. 5, July/August 1999, which is expressly incorporated herein in its entirety by this reference. The beamsplitter provides identical light pulses to the reference and probe arms of the OCT system, and the detector/signal processing section determines a variety of tissue properties based upon the interference pattern obtained from the beamsplitter. In one embodiment of the invention, only a portion of the probe arm and the lateral scanning optic control would be invasive with the rest of the system remaining external to the tissue host.

The requirement for a broadband light source is a good match for the ultra-short optical fiber delivery source employed in some embodiments of the invention. The advantages of an ultra-short pulse are made apparent when one looks at the equation for z-axis resolution available from a broadband light source with a Gaussian shaped pulse:

$$Zr \approx 0.44 \frac{\lambda_o^2}{\Delta\lambda}$$

where $\lambda_o$ is the source center frequency and $\Delta\lambda$ is the FWHM of the coherence function. The spectral spreading accomplished by using an ultra-short pulse may be of great benefit in axial system imaging resolution. Additionally, most USP laser systems have center wavelengths ~800 nm which is compatible with deep penetration into biological tissue. Hence, the light source discussed herein (reduced in power density) may provide a robust OCT broadband source.

Precision control of the tool 10 may provide a "coarse" scanning mechanism, while in some embodiments, incorporation of miniature beam focusing and directing optics into the tip end of the tool will provide precision beam focusing as well as additional x-y and rotational control over the imaging area. Such a system has been successfully demonstrated with up to video rate imaging. See G. J. Tearney, et al, "Scanning single-mode fiber optic catheter-endoscope for optical coherence tomography", *Optics Letters*, vol. 21, April 1996, which is expressly incorporated herein in its entirety by this reference. This detailed optical control when combined with the high precision mechanical control provided in some embodiments of the tool enable detailed mapping of large regions of tissue.

In Vivo Ultrasonic Pinger

An in vivo ultrasonic pinger, i.e., a soundwave generator may be located at or near the tip of the device. The pinger periodically emits an ultrasonic pulse to allowing tracking of the insertion of the device, using existing medical ultrasonic equipment, and allowing, for instance, faster device insertion. This can be powered, for example, by electrical wires run along the length of the tube, by pneumatic or hydraulic pressure to a micromechanical trip-hammer hitting a miniature tuning fork, by adsorbing energy from the laser, or from the ultrasonic energy that the external ultrasonic equipment introduces. In one embodiment, this can work in concert with the other imaging techniques, such as a movable laser beam in vivo television (TV) camera (described below), to provide a broad field of view, as compared to the narrower field of view of the laser beam camera. The signal-to-noise (S/N) ratio in principle should be higher since impedance (Z) mismatch is less of an issue. The transducer is located inside the body attached to the tool end.

Optical Imaging

Modern endoscopic techniques allow relatively precise approaches, on the submillimeter scale, to undesirable lesions such as polyps and tumors. Visual information is able to supplement effectively LIF data and to promote further in situ optical tissue discrimination and diagnosis. In some embodiments, selective filtering and special data processing may enable better and more tissue-specific visual imaging according to the invention. However small the miniaturized tool can be, it still can employ binocular vision using oppositely situated bunches of reception fibers. This can determine and maintain the distance to the site of action with precision of 10-50 µm. To boost further precise dimensional control, optical and fluorescent markers may be deployed from one of the fluidic nozzles in some embodiments. Small plastic beacons can also be delivered temporarily and inserted into the incision by an endoscopic micromanipulator. Such other optical imaging means as would be known to one of ordinary skill in the art are also contemplated within the scope of the invention.

Movable Laser Beam as In Vivo Television Camera

A laser waveguide with a beam movable in 2D with respect to the end of the tool can be made to scan, and is therefore contemplated to be another means of detection and imaging according to the invention. Reflections may be picked up by the same and/or one or more other optical fibers (other fibers might or might not be moved with the beam) and, after processing, displayed on a TV screen. This may be done in color by sequentially firing laser pulses with red, green, and blue wavelengths. This may also be done in at least the near-IR and near-UV regimes, which may yield additional information (fluorescence, temperature, or IR signatures). The scan may be the TV type with a series of lines, but could also be a series of concentric circles, or a spiral, e.g., starting at the center and spiraling outwards. The display may be made by controlling the electron beam of a cathode ray tube (CRT) to move it in the same pattern, or by using a computer, convert the display to be viewed on a conventional TV or with advanced 3D virtual-reality equipment.

In one embodiment, the beam is scanned by applying modulated electric fields across a pair of quartz crystals. The same waveguide may be used for in vivo laser ablation of tissue.

Therapeutic Emission Technologies

In some embodiments, the apparatus and methods of the invention include at least one therapeutic emitter 700 (e.g., FIG. 2A) for performing therapeutic processes at the target area. In one embodiment, the invention includes an apparatus and methods for performing low-energy photon therapy (LEPT) that is activated by lasers or light-emitting diodes (LED's). LEPT is a treatment for wounds, especially ulcers and other ischemic wounds that do not heal normally. In another embodiment, the therapeutic emitter 700 comprises a low-energy photon generator for generating a therapeutic light beam, and at least one delivery fiber for carrying the light beam from the generator to the tip end of the tool.

LEPT is contemplated as a treatment for diabetic ulcers, laser-induced retinal lesions and dental pain, as well as for inducing healing of refractory wounds (e.g., radiation-induced ulcers) and increasing the rate of healing in various experimental wound models. See Pekka J. Pöntinen, "Low-Energy Photon Therapy," in A. M. Schoen and S. G. Wynn, eds., *Complementary and Alternative Veterinary Medicine: Principles and Practices* (St. Louis, Mo.: Mosby, 1998), Chapter 17, which is expressly incorporated herein in its entirety by this reference. For instance, H. T. Whelan of the Medical College of Wisconsin has shown that near-IR light promotes wound healing in human and animal studies. See Whelan, H. T.; et al. "Medical Applications of Space Light-Emitting Diode Technology—Space Station and Beyond," *Space Technology Applications International Forum* 1999, 458, 3; Whelan, H. T.; et al. "The NASA Light-Emitting Diode Medical Program—Progress in Space Flight and Terrestrial Applications," *Space Technology Applications International Forum* 2000, 504, 37; and Whelan, H. T. et al. "NASA Light-Emitting Diode Medical Applications from Deep Space to Deep Sea," *Space Technology Applications International Forum* 2001, 552, 35, which are expressly incorporated herein in their entirety by this reference. His preliminary results have also demonstrated two- to fivefold increases in growth-phase-specific DNA synthesis in a variety of non-neuronal cell types in cultures treated with near-IR light. Results of previous studies have shown that optimal wavelengths to speed wound healing include 680 nm, 730 nm, and 880 nm. See Pekka J. Pöntinen, "Low-Energy Photon Therapy," in A. M. Schoen and S. G. Wynn, eds., *Complementary and Alternative Veterinary Medicine: Principles and Practices* (St. Louis, Mo.: Mosby, 1998), Chapter 17, which is expressly incorporated herein in its entirety by this reference. Optimal exposures reported are energy density or fluence (F) values of approximately 4-8 J/cm$^2$ (40-80 kJ/m$^2$), and irradiance (H) values of approximately 50 mW/cm$^2$ (500 W/m$^2$).

Mouse-derived osteoblasts were observed to demonstrate increased cell growth of 100%-115% at 24 hours after LED irradiation with individual wavelengths of 670 nm, 730 nm, and 880 nm, F=8 J/cm$^2$ (80 kJ/m$^2$), and H=50 mW/cm$^2$ (500 W/m$^2$) compared to untreated controls. See Pekka J. Pöntinen, "Low-Energy Photon Therapy," in A. M. Schoen and S. G. Wynn, eds., *Complementary and Alternative Veterinary Medicine: Principles and Practices* (St. Louis, Mo.: Mosby, 1998), Chapter 17, which is expressly incorporated herein in its entirety by this reference. Exposure to LED irradiation accelerated the growth rate of fibroblasts and osteoblasts in culture for 2-3 days (growing phase), but showed no significant change in growth rate for cells in culture at 4 days (stationary phase). This demonstrates cell-to-cell contact inhibition, which occurs in vitro once cell cultures approach confluence. This is analogous, in vivo, to a healthy organism, which can regenerate healing tissue, but stop further growth when healing is complete.

In some embodiments, DWDT/HAT incorporates methods by which to perform LEPT in vivo through an endoscopic device. LEPT could be used in vivo to accelerate cell migration, cell differentiation, or cell proliferation. In some embodiments, the DWDT/HAT may include multiple discrete fibers to deliver light of wavelengths from the IR through the UV regimes for performing detection functions as discussed in detail above (including LIF and FTIR), for possible enhanced cell proliferation or differentiation (visible, IR) and for the delivery of high-H laser pulses for ablation. In some embodiments, two or more of these discrete functions may be performed using a single fiber to deliver light for different purposes as desired.

Vision Technologies

In some embodiments, the invention includes at least one imaging device 500. For example, in one embodiment the imaging device 500 is an endoscopic camera 510. (FIG. 7). Various suitable embodiments and implementations of such endoscopic cameras are known to those having ordinary skill in the art.

Many endoscopic devices for vision processing, which extract, correct, and combine images from a single endoscopic lens, introduce a "fish-eye" effect into the resultant images. Such devices are suitable for use in the present invention, but in some embodiments this effect is such that features are not readily recognizable to the operator, nor is relative spatial and scale information accurate. Therefore, some correction to the raw image created by such devices is desirable.

Existing research into this area has shown favorable results indicating that computationally efficient methods can reverse the "fish-eye" effect. See K. Vijayan and D. Radhakrishnan, *IEEE Transactions on Medical Imaging* 1999, 18 (4), 345, which is expressly incorporated herein in its entirety by this reference. After the correction of single-frame images, it is necessary to combine them into a panorama that can allow the user to see a greatly expanded field of view. Research into this problem has shown that a series of "warped" images can be corrected and combined into a mosaic with only a small error introduced. See H. S. Sawhney and R. Kumar, *IEEE Transactions on Pattern Analysis and Machine Intelligence* 1999, 21 (3), 235, which is expressly incorporated herein in its entirety by this reference. The computational efficiency of this approach is enhanced by using multiscale processing preceded by the application of a Laplacian-Gaussian filter (LGF). According to the invention, this process may be enhanced by replacing the LGF with a nonlinear process to eliminate the edge blurring and movement associated with the linear LGF approach. See J. Bosworth and S. T. Acton, "The Morphological LOMO Filter for Multiscale Image Processing," in *International Conference on Image Processing* (October 1999), which is expressly incorporated herein in its entirety by this reference. Precise location of edges may improve the user's ability to identify tissue features.

Material Destruction Technologies

In some embodiments, the invention includes an apparatus for performing subtractive processes, also referred to herein as a material destroyer 200 (e.g., FIG. 2A). As referred to herein, a material destroyer is any apparatus adapted for separating material from its endogenous position, including any apparatus for separating cells or tissue by any means from their endogenous position in the body.

In one embodiment, therefore, one such subtractive process is the cutting action of a conventional MIS surgical instrument, such as an endoscope, as known to those having ordinary skill in the art. In another embodiment, subtractive processes include a laser-based material destroyer instead of, or in addition to, the cutting action of a traditional MIS tool. Referring now to FIGS. 4-7, in one such embodiment, the tool 10 includes a tip end 17 and a spaced back end (not shown). The detector material destroyer 200 includes a laser source (not shown) for supplying energy used in the destruction process. At least one optical fiber 230 is included for carrying the laser light, having a remote end (not shown) operatively coupled to the laser source and a spaced emitting end 234 adjacent the tip end 17 of the tool. The material destroyer 200 also includes an energy density concentrator (not shown) operatively coupled to the laser source for concentrating energy supplied by the source.

Such a laser-based system may include a fiber-delivered laser beam with variable-pulse-duration—from continuous wave (CW) to ultrashort-pulse (USP). The USP permits the material destroyer 200 to trim, to shape, and to remove tissue precisely with cellular specificity in either the damaged or the construction regions without compromising the surrounding tissue.

The fiber delivery system also allows controlled thermal heating. Dr. K. Bartles of Oklahoma State University (OSU) has developed a technique in which a laser elevates the temperature in specified locations to "boil" unwanted tissues or cells. See K. Bartles, Oklahoma State University, personal communication, 2002, which is expressly incorporated herein in its entirety by this reference. In some cases, a chemical tag is added to increase the absorptivity of the target. In either eventuality, this technique is fully compatible with the apparatus of the invention, which could both dispense the chemical tag and deliver the laser source to the specified location for destroying unwanted tissue (e.g., malignant tumors). The remaining healthy tissues and/or organs cleanse themselves of the destroyed tissue debris over time, thus allowing new growth of healthy tissue. See K. Bartles, Oklahoma State University, personal communication, 2002, which is expressly incorporated herein in its entirety by this reference.

In general, lasers have affected many lives by changing the practice of medicine and offering new approaches to major health problems, such as the treatment of cancer, kidney stones, and eye diseases as well as diagnostic techniques. The use of optics and fiber optics has led to less invasive ways of treating disease by replacing open surgery with MIS, enabling the surgeon to visualize the body's interior.

Lasers, with dozens of established medical procedures and applications, are no longer new to the world of medicine, and with the advent of LASIK (laser in situ keratomileusis), medical lasers have become familiar to the public. Current medical-laser techniques use lasers that range from CW to pulses with durations ($\tau_p$) in the nanosecond regime (NSR, $10^{-9}$-$10^{-7}$ s). The corresponding material-removal mechanism varies from purely thermal to a combination of thermal and ablative. The degree of ablation is directly related to the peak irradiance at the substrate. At H~100 MW/cm$^2$ (1 TW/m$^2$) for NSR pulses, ablation becomes the dominant mechanism. However, as illustrated below, even NSR pulses have a distinct thermal component.

A thermal interaction arises from absorption of laser radiation by the tissue. This type of laser-material interaction occurs up to H~1 MW/cm$^2$ (10 GW/m$^2$), and is typical of CW lasers or LP ($\tau_p$~1 ms) lasers. In these photothermal processes, the substrate is heated beyond its boiling or decomposition point, after which it becomes vaporized. This is a very energy-intensive process and requires a relatively large ancillary power supply. When a NSR laser pulse interacts with a material, several things occur. First, thermionic emission occurs and electrons are ejected. The laser pulse is sufficiently long enough to couple into the conduction-band electrons in the substrate and heat is transferred to the lattice through photon-phonon interactions. Ionization of the material also occurs, probably through multiple-photon ionization. Han and Murray have measured this effect; at high H values, the ions in the plasma obtain substantially high velocities, over 30 km/s, by the inverse Bremsstrahlung effect. See G. Han and P. T. Murray, *Journal of Applied Physics* 2000, 88 (2), 1184, which is expressly incorporated herein in its entirety by this reference.

Wavelength-dependent absorption tends to promote thermal ablation in a more-or-less linear fashion for absorptive materials. The operator must be careful of undesired absorption of the laser energy by bodily fluids before desired absorption by the target tissue. This case will necessitate subsurface focusing. At elevated fluences, the target material will melt and evaporate; increased fluences above the so-called ablation threshold ($F_{ablation}$) cause ionization and plasma formation—a process typically referred to as "plume formation." In the case of $\tau_p$>1 ns laser sources, the zone immediately surrounding the ablated area will have large particles and resolidification zones due to excessive localized heating and melting of the residual target material (e.g., tissues). LP lasers have the positive attribute of inducing cauterization due to the thermal melting process, but they also induce significant damage to the surrounding tissue due to the longer thermal diffusion length.

Ultrashort Pulse (USP) Lasers

During an USP, the laser may have insufficient time to couple into the substrate through photon-phonon interactions. This is illustrated by laser-induced damage studies that show a definite change in damage mechanism when $\tau_p$<25 ps. See W. Koechner, *Solid-State Laser Engineering*, 5th ed. (Heidelberg: Springer-Verlag, 1999), which is expressly incorporated herein in its entirety by this reference. The subtractive process here, using USP lasers, is not thermal but rather photoablative. Specifically, with respect to USP lasers, the absorption leads to optical breakdown and permanent structural changes in the immediate vicinity of the focus, while leaving the surrounding material substantially unaffected. See Materials Research Society, *Materials Research Society Bulletin* 2001, 26 (2), 86, which is expressly incorporated herein in its entirety by this reference. For USP lasers, a photoablative phenomenon dominates. Atomic and molecular bonds are directly broken by very large local electric fields induced by the tremendous irradiance resulting from highly focused, ultrashort-duration laser pulses. This photoablative phenomenon is the result of microplasma caused by avalanche ionization, and multiphoton absorption and ionization (both of which are nonlinear processes). The atoms and molecules near the laser pulse are not in thermal equilibrium. Instead, they experience intense electric fields (over $10^7$ V/cm or $10^9$ V/m) that directly ionize atoms and induce avalanche multiplication that breaks molecular bonds and causes material ejection. Despite the very high irradiance of the laser pulse, H>$10^{10}$ W/cm$^2$ (100 TW/m$^2$), it has a very short duration, $\tau_p$<$10^{-12}$ s. This period is sufficient for plasma to leave the point of immediate contact, yet is too short to transfer acquired kinetic energy to the neighboring substance. Therefore, the pulse energy is dissipated by breaking interatomic bonds and ejecting the plasma cloud, which does not increase temperature. Targets such as tissues subjected to irradiation using FSR to picosecond-regime (PSR) pulsed laser sources have the positive attribute of being quite smooth and comparatively free of extensive melt-zone regions to surrounding tissues.

In some embodiments, the invention incorporates a laser system that can be used for subtractive processes (e.g., ablation). The DWDT/HAT subtractive laser capability provides: (1) the ability to remove cells without inducing damage to surrounding media (with the appropriate numerical-aperture lens); (2) a thermal tissue ablation and cauterization in one system; and (3) the construction of tissue-engineering tracks for controlled topology (e.g., for enhanced cell proliferation and attachment) and vascularization (angiogenesis).

In one embodiment, such features are achieved by utilizing one or more lasers and a laser-delivery system that has attributes of both long- and ultrashort-duration pulses. In another embodiment, the invention incorporates a fiber coupling/delivery system that features: fiber coupling of laser light of different pulse durations ($\tau_p$, s), wavelengths ($\lambda$, m), fluences (F, J/m$^2$) and irradiances (H, W/m$^2$); fibers for vision and/or imaging systems; various fiber designs for USP lasers (modeling and fiber development); and the ability to focus (and thereby increase F and H) at the fiber tip.

The Cusp Between Ultrashort and Long Pulse Durations

In some embodiments, the use of both LP and USP lasers may be advantageous for laser subtractive processes with tissues as the target. See M. D. Perry, B. C. Stuart, P. S. Banks, M. D. Felt, V. Yanovsky, and A. M. Rubenchik, *Journal of Applied Physics* 1999, 85, 6802, which is expressly incorporated herein in its entirety by this reference. The USP lasers provide a clean cut to the tissue with the LP lasers being used immediately afterwards to induce cauterization.

Figure 8:
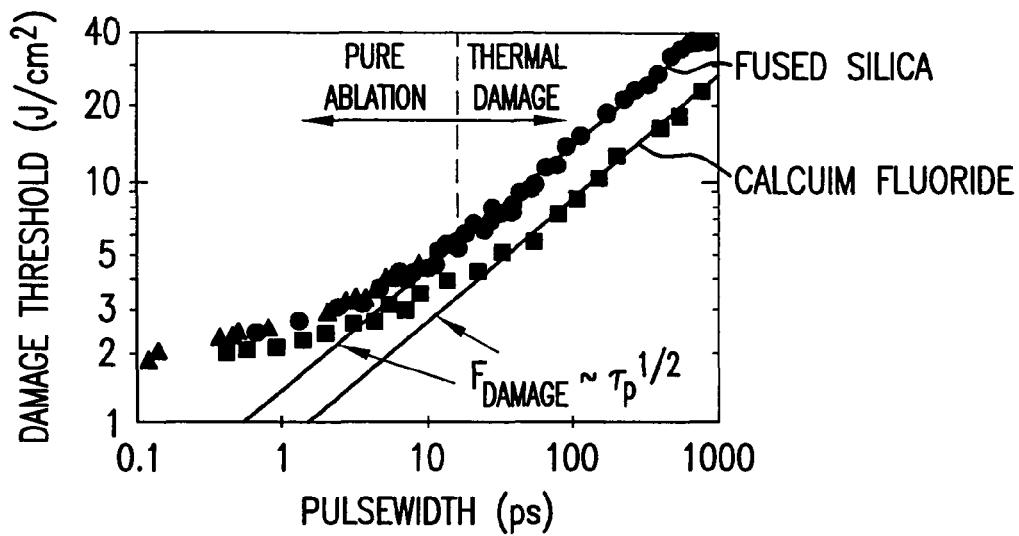
FIG. 8 is a graph of damage threshold versus pulsewidth for one embodiment of a laser source for the invention.

Thus, in one embodiment, the material remover may comprise one laser that has a $\tau_p$ value near the cusp of traditional LP and USP lasers. FIG. 8, adapted from M. D. Perry, B. C. Stuart, P. S. Banks, M. D. Felt, V. Yanovsky, and A. M. Rubenchik, *Journal of Applied Physics* 1999, 85, 6802 (which is expressly incorporated herein in its entirety by this reference), shows the damage threshold fluence ($F_{damage} \leq F_{ablation}$) for lasers of various pulse durations. A clear materials demarcation exists between the USP ($\tau_p \leq 1$ ps) and LP lasers ($\tau_p > 300$ ps). The fluence of LP lasers is a function of $\tau_p^{1/2}$, a direct consequence of the thermal diffusion length. Thus, there exists a "fuzzy" $\tau_p$ zone between the USP and LP regimes, somewhere between 1-300 ps. In this $\tau_p$ regime, to first order, the benefits of both laser types will be achieved, i.e., a relatively clean tissue cut with some localized thermal damage to induce cauterization.

Laser Sources

To generate the high-H USP's, many USP lasers use regenerative amplified titanium-doped sapphire lasers (TSL's) and amplified dye lasers. Due to their absorption in the blue-green part of the visible spectrum, TSL's are usually pumped by gas-ion lasers or frequency-doubled neodymium(III)-based lasers. These particular USP laser systems are of considerable size and complexity; however, such USP lasers may be used in the medical arena. Such systems therefore comprise an embodiment of the invention.

Figure 9A:
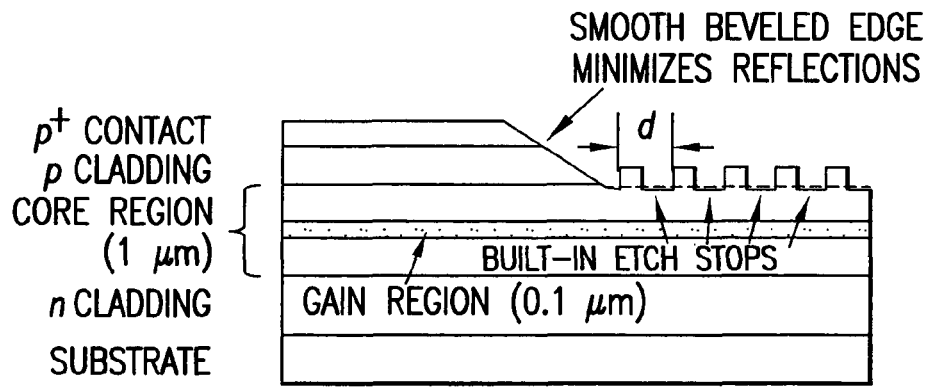
FIGS. 9A and 9B are views of a grating coupled surface emitting laser diode according to the invention.
Figure 9B:
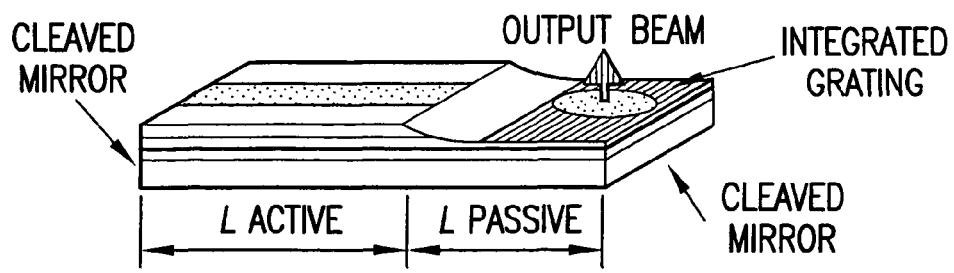

In other embodiments, laser diodes may be utilized, which are significantly smaller than traditional solid-state USP lasers and compatible with MIS procedures. The technology is based on the integration of dispersive optical elements (e.g., gratings) within the cavity of the laser diode as shown in FIGS. 9A and 9B (14). In one embodiment, this laser diode may be a Grating-Coupled Surface-Emitting Laser (GCSEL) about 1-3 mm long.

GCSEL diodes overcome both of the limiting features of Fabry-Perot diodes. The larger emissive area of GCSEL diodes allows significantly more optical power to be pumped out of the laser for the same gain areas as in Fabry-Perot diodes. Furthermore, the larger vertical emissive surface also allows the GCSEL to have an incredibly small divergence of about 0.1°.

Compared to current TSL technologies, the GCSEL offers the following potential advantages: the size of the laser head can be reduced by several orders of magnitude; efficiency can be improved by many orders of magnitude (laser diodes are routinely ~40% efficient as compared to 0.2%-efficient TSL's); power supply requirements can be reduced by several orders of magnitude; and the economy of scale of integrated electronics can reduce the unit price from $250,000 to less than $10,000. Thus, the integration of the GCSEL diode offers many advantages in parallel to those offered by the integrated circuit for microelectronics.

In another embodiment, the laser source is a fiber laser, which is a solid state laser comprised of diode lasers for pumping, a short pulse generator and fiber amplifiers. The short pulse generator can be comprised from a variety of fiber and non-fiber sources, but fiber sources include mode locking a fiber laser to generate ultra short pulses. Coupling from a fiber generator to a fiber amplifier can provide efficient coupling. The pulse width through the amplification can be varied by varying the fiber length. Dispersive fibers will expand pulses as a function of length. Fiber amplifiers also have pump sources which are typically diode lasers. Advantages of the fiber laser include extreme powers in small areas, as given by fiber diameter. The output of the fiber laser is through the fiber, therefore placing the output coupler in an endoscope is feasible and compatible.

Fiber Delivery

A USP delivery system must be able to withstand pulses in the FSR ($10^{-15}$-$10^{-13}$ s). The FSR gives the ability for the pulse to interact with "any" material, including those that are typically transparent at a specified wavelength when irradiance is sufficiently high. Calculations for the FSR laser have indicated that a typical single-mode fiber with a core diameter of 5 μm would not survive the transmission of microjoule laser energy. The subtractive process can consist of the GCSEL coupled to one or more fibers for ablation purposes. Since large irradiances may destroy a typical single-mode fiber, the core is expanded. This reduction in H also implies that a focusing lens typically can be used on the end of the fiber to increase H back to ablation values at the desired spot.

Designs and possibilities for the USP laser delivery system, particularly the fiber-based system discussed herein, are of particular interest because they are robust, compact, efficient, flexible, and MIS-compatible. They also have high heat-load capacity.

In a conventional optical fiber, light is confined in a silica inner rod by a "cladding" of glass with a slightly different composition than that of the core. Typically, the silica-based core is doped with either germanium or phosphorus to provide a different refractive index (n) from the cladding. The change in refractive index ($\Delta n$) causes the light striking the interface between the core and the cladding to become reflected. This causes the light to be bounced back and forth down the fiber core; it remains largely within the core.

The limitations specific to conventional optical-communications fibers include scattering, leakage, inability to tolerate high H, and nonlinear-optical (NLO) effects. Some of the light passing through a conventional fiber is "scattered" by part-per-billion to part-per-million concentrations of impurities in the silica, including hydroxyl (—OH) groups. These scattering impurities disrupt the transmission of some of the laser light as it travels through the fiber core. Some of the light is also able to escape from the fiber because its core and cladding interfaces are not perfect mirrors. The largest factor, however, that limits the use of conventional fibers for USP laser delivery is that the fiber core is very narrow and cannot support high-H pulses; high-H light that emanates from USP lasers destroys most conventional fibers. Lastly, NLO effects can be a large impediment to the use of traditional fiber materials.

In several embodiments, single-mode fibers, as well as the following alternative fiber designs are contemplated according to the invention.

Wide-Core Fibers

Compared to single-mode fibers, wide-core multimode fibers have larger diameters and therefore reduce H in the fiber core, allowing the high-power pulses required for tissue ablation to propagate without experiencing NLO effects or damaging the fiber. The multimode behavior can likely induce some dispersion in the light, though dispersion in the PSR can be minimal. Multimode behavior is not ideal from a pure "physics" point of view due to the inability to focus tightly, but is likely reasonable from a tissue ablation point of view if larger spot sizes are acceptable. Advantages of the wide-core fibers include a large numerical aperture (NA)—it is easy to couple light into the fiber—and low bending losses.

The step-index multimode fiber was initially tested with a commercial femtosecond-regime titanium-doped sapphire laser source. Approximately two meters of fiber were coiled with a bend radius of r≈11.5 cm. The input power was $P_{in}$=620 mW. The operating wavelength was λ=800 nm, with a spectral bandwidth Δλ=9.5 nm full width at half maximum (FWHM). The output power was $P_{out}$=550 mW, corresponding to a transmission efficiency of 89%. The output spectrum exhibited several sharp peaks that shifted when the fiber input was translated in any transverse direction. In this case, the input and output powers were $P_{in}$=600 mW and $P_{out}$=490 mW, respectively.

Several changes were made to the experimental setup after the early tests with the TSL. Neutral-density filters were added to control $P_{in}$, allowing the fiber to be placed at the beam waist without being damaged. In addition, the coupling lens was replaced with a positive-negative lens combination to act as a beam reducer. The reducer permitted focusing to spot sizes of approximately the fiber diameter in a small NA. This allowed higher incident power at the fiber input face without damage and reduction of the number of propagated modes. Mode matching of the input beam to the fundamental mode of the fiber was attempted as a means to reduce intermodal dispersion and to increase output beam quality. The optimum spot size at the fiber input for the highest power coupling into the fundamental mode was calculated to be 0.64× the fiber diameter or 352 μm. The coupling optics were oriented to achieve this spot size and beam profiles were taken before and after passing through the fiber.

Using this coupling arrangement, the TSL was tuned to output $\tau_p$=100 fs pulses and $P_{out}$ was measured as a function of $P_{in}$. Multicolored light was observed at the output for $P_{in}$>16 mW, corresponding to a peak power of $P_{peak}$=160 MW. The calculated stimulated Raman scattering (SRS) threshold power for the 62-cm-long fiber was 153 MW, so these numbers are in good agreement. For $P_{in}$>25 mW, white light emerged from the fiber. Measurements were taken up to $P_{in}$=470 mW.

The SRS threshold power was set as the upper limit for delivered power in the material ablation experiments. This being the case, the only fiber that delivered sufficient energy to ablate the proposed material samples was the 550-μm step-index multimode fiber.

The ablation setup was comprised of 61 cm of 550-μm step-index multimode fiber and the two-lens beam-coupling optics. The input beam had a spot size of w=350 μm and a focal number (f/#) of 330, giving a spot size to core diameter (d) ratio of w/d=0.61. (The focal number is the ratio of the lens focal length to the beam diameter at the lens and is inversely related to the numerical aperture: f/#=1/(2 NA).) See F. L. Pedrotti and L. S. Pedrotti, *Introduction to Optics*, 2nd Edition (Upper Saddle River, N.J.: Prentice Hall, 1993), which is expressly incorporated herein in its entirety by this reference. The calculated SRS threshold power was $P_{th}$≈62 MW, corresponding to an average power of $P_{avg}$=43 mW. The $P_{in}$ measured before the fiber was 48.5 mW; however, taking into account reflection from the fiber input face and coupling efficiency, the power coupled into the core was closer to $P_{in}$=39 mW. The actual measured $P_{out}$=37 mW, which is below the SRS threshold. The fiber output was focused using a 50× microscope objective with a NA of 0.85. The samples were attached to a translation stage with stepper motor control in the horizontal direction and manual adjustment in the vertical and axial directions. A shutter was placed before the focusing optics to control the number of pulses incident on the sample.

The samples were ablated under three different conditions: before the fiber, with the fiber kept straight, and with the fiber bent 45° with a 5-cm bend radius. In each case, the sample was placed at the focus of the 50× objective and was translated horizontally to the fiber output. The beam was passed over the sample=until the material was machined through to the substrate. The $P_{avg}$ before the objective for each of the three cases was 48.5, 37, and 35 mW, respectively. The translation speed for all cases was 0.5 mm/s.

The samples were gold lines ≈380 μm wide and 8-10 μm thick. Cuts were made by placing the 50× objective immediately before the fiber input and translating the sample at 0.5 mm/s in a single pass. The width of the cut was 25 μm. Therefore, given the pulse energy of $E_p$=48.5 μJ, the fluence at the focus was F 9.9 J/cm² (99 kJ/m²). This is well above the gold $F_{ablation}$≈0.4 J/cm² (4 kJ/m²) for FSR pulses. See M. D. Perry, B. C. Stuart, P. S. Banks, M. D. Felt, V. Yanovsky, and A. M. Rubenchik, *Journal of Applied Physics* 1999, 85, 6802, which is expressly incorporated herein in its entirety by this reference. In another trial, a cut was made by placing the 50× objective after the fiber and translating the sample at 0.5 mm/s for 5 passes. The width of the cut machined through to the substrate was ~25 μm; however, the entire width of the machined region was =60 μm. This was due to the inability to focus tightly the multimode output from the fiber. The result was a wider machined cut with staggered sidewalls.

Machining was also performed with the fiber bent at 45° with a 5-cm bend radius. The cut was made by translating the sample at 0.5 mm/s for 10 passes. In this case, the width of the cut increased to =30 μm. Since the width of the machined region was still ≈60 μm, the increase in the cut width was most likely due to the increased number of passes, though it is possible that the bending excited higher-order modes and limited the ability to focus.

Air-Gap Fibers

The idea of having light traverse through air is one possible approach, because light travels through air with little scattering. Likewise, it is less likely to "destroy" the air "core" at the higher H of USP lasers because air does not ionize until very high H at normal λ. Such hollow waveguide fibers, also known as air-gap fibers, have an additional benefit in that they reduce NLO effects. Several variants of hollow core fibers and proposed for in vivo and in vitro DWDT/HAT.

One meter of 500 mm core diameter hollow waveguide (HWG) was tested with input pulses from a Spitfire Ti:Sapphire regenerative amplifier. The input pulses were ~87 fs full width at half maximum (FWHM) and had a central wavelength of 800 nm. A positive/negative reducer lens combination was used to focus the beam to a spot size of ~320 um with an f/# of ~310 at the waveguide input. This excitation corresponded to near-optimum coupling to the fundamental (HE11) mode of the waveguide, significantly reducing the number of higher order modes in the waveguide and thereby limiting the amount of intermodal dispersion and divergence at the waveguide output. To suppress bending loss and higher order mode excitation within the waveguide, the fiber was held straight under slight tension between two fiber holders. For an input average power of 675 mW (7.75 GW peak), the power transmitted through the coupling optics and into the waveguide was 605 mW. This ~10% loss is mainly due to the loss from the uncoated negative lens in the reducer combination. The average power measured at the output of the waveguide was 220 mW (220 µJ output energy), giving a transmission efficiency of 36%. The far-field output 2-D and 3-D beam profiles were single lobed, indicating a significant suppression of most higher-order modes. The measured spot size at 310 mm from the fiber output was 2.4 mm×2.9 mm, resulting in an output f/# of ~119 (numerical aperture=0.0042). The output was focused with a 10× microscope objective and air breakdown was observed at focus. With a 50 mm spot at focus, the 220 mJ output energy of the hollow waveguide gives a fluence of ~11.2 J/cm^2, which is enough to ablate most materials, given an ultrashort pulse. Aluminum and Kapton samples were also readily ablated at focus.

Metallic Waveguides

In some embodiments, metallic waveguides may be utilized as the transmitting fiber or medium for the laser beam. A simple concept of a hollow fiber is one having metallic mirrors (such as silvered glass) and which acts like a metal light waveguide. Typically, these metallic waveguides are not nearly reflective enough to work in fiber optics; they absorb and dissipate a small but significant part of an incoming beam. A light signal traveling down a silver-lined glass tube would travel only a short distance before dispersing entirely. However, this is primarily a problem for optical-communications applications, in which the light must traverse significantly long distances. For some embodiments of the present invention, the light is only required to traverse a very short (1 m) distance. Metal waveguides have been successfully applied to high-energy PSR pulses in vitro. See Y. Matsuura, K. Hanamoto, S. Sata, and M. Miyagi, "Hollow Fiber Delivery of High Power Pulsed Nd:YAG," *Optics Letters* 1998, 23, 1858, which is expressly incorporated herein in its entirety by this reference. Furthermore, the hollow waveguides make it possible to guide both long-and short-pulse light in the same fiber. See H. Jelinkova, J. Sulc, P. Cerny, Y. -W. Shi, Y. Matsuura, and M. Miyagi, "High Power Nd:YAG Laser Picosecond Pulse Delivery by a Polymer Coated Silver Hollow Glass Waveguide," *Optics Letters* 1999, 24, 957 and Y. Matsuura, K. Hanamoto, S. Sata, and M. Miyagi, "Hollow Fiber Delivery of High Power Pulsed Nd:YAG," *Optics Letters* 1998, 23, 1858, which are expressly incorporated herein in their entirety by this reference. Again, just like the wide-core fibers discussed earlier, the laser light emanating from the metal waveguide can be multimode and hard to focus. However, smaller spot sizes can be realized by using waveguides with smaller cores (100-µm spot sizes are possible). If the hollow waveguide is placed close to the object to be ablated, then the spot size will not be overly enlarged due to solid-angle effects.

Spot size reduction at the output of a hollow waveguide may be achieved by fundamental-mode excitation at the input. Fundamental-mode coupling in a multimode waveguide requires that the spot size and focal number of the input beam give a fundamental-mode coupling efficiency near 100%. For most hollow waveguides, this occurs for w/d≈0.64.

One meter of 500-µm-diameter hollow waveguide was tested with input pulses from a TSL regenerative amplifier. The input pulses had duration $\tau_p$=87 fs FWHM, repetition rate $R_p$=1 kHz, and central wavelength λ=800 nm. A positive/negative reducer lens combination was used to focus the TSL beam to a spot size of w≈320 µm with f/#≈310. This excitation significantly reduced the number of higher-order modes in the waveguide, thereby limiting the amount of intermodal dispersion and divergence at the waveguide output. To suppress bending loss and higher-order mode coupling within the waveguide, the fiber was held straight under slight tension between two fiber holders. For an input $P_{avg}$=675 mW ($P_{peak}$=7.75 GW), the power transmitted through the coupling optics was 605 mW. This ≈10% loss is mainly due to the loss from the uncoated negative lens in the reducer combination. The power measured at the output of the waveguide was $P_{out}$=220 mW, giving a transmission efficiency of 36%. The measured spot size at 310 mm from the fiber output was w≈2.6 mm, resulting in an output f/# of 119 (NA=0.0042). The output was focused with a 10× microscope objective and air breakdown was observed at focus.

The hollow waveguide used in this experiment was designed for the delivery of erbium-doped yttrium aluminum garnet (Er:YAG) output at λ=2.94 µm. It has a silver layer on the waveguide walls for reflection and a dielectric layer coating the silver. The loss in the near-IR region near λ=800 nm could be reduced with smoother silver layers to reduce scattering and dielectric layers of optimal thickness to increase reflection.

Flexible Flat Optical Waveguide/Probe

For a given core area, flattened optical waveguides that are smaller in one direction and larger in the other, ie., elliptical, as compared to waveguides with a round cross-section may be utilized in some embodiments. A horn can concentrate the energy into a desired spot size and shape with either type. Advantages to such a flat optical waveguide include high flexibility in two (opposite) directions and relative stiffness in the other two. Thus, it may be generally easier to handle as it is less likely to be damaged by bending in the thin directions and resists bending in the other directions. Partially inserted as a probe, it can be steered to some extent by twisting the uninserted portion. It can also be wound around a smaller-diameter spool. An incision for a flattened tube may be smaller and/or heal quicker than for a round tube.

One variation is to have an elastic-covered, notched rib on one side, such that the waveguide would only bend easily in one direction. This device may be easier to steer as a probe. A second variation is be to have an elastic-covered, linearly expandable bellows, rather than the notched rib, on one side, such that the waveguide bending could be controlled. Another is be to use three or four fluid jets to move and steer the probe.

In Vivo Pulse Concentrator

The in vivo pulse concentrator avoids transferring high-H fields through the body. It transfers only nonablative H through a tube and then concentrates the electric field adjacent to the point of use. It is a grating built into the fiber for pulse compression through such methods as ion implantation. The grating design is complementary to the grating design of the GCSEL used for pulse compression, which can lead to USP and high H. Thus, a crack in the tube would not cause unwanted ablation.

Photonic Bandgap Fiber (PBF) Materials

Photonic bandgap fiber (PBF) materials, which are usually doubly periodic structures, can be designed with engineered stopgaps that disallow the transmission of light. The engineered stopgaps can be loosely defined as the mitigating specific wavelengths of light; those wavelengths simply cannot enter the material. The heart of a PBF is simply a microstructured material, with the microstructure on the scale of the optical wavelength of interest. If the structure is regularly repeating (periodic), the material is called a "photonic crystal." This is analogous to a normal crystalline material (e.g., silicon, quartz, gallium(III) arsenide) in which atoms or groups of atoms are arranged in a repeating pattern to form the electronic bandgap of the material as described in quantum mechanics (e.g., the Kronig-Penney model). The difference with a PBF is that the repeated period is on a much larger scale, the order of a micrometer rather than a fraction of a nanometer, which is the interatomic distance in a crystal.

The PBF materials in principle do not allow light to escape from an empty core (air-gap core) wrapped within them. See J. Knight, B. Mangan, W. Wadsworth, G. Kakarantzas, W. Reeves, A. Ortigosa-Blanch, E. Davies, T. Hedley, and P. Russell, "Photonic Crystal Fibre," http://www.bath.ac.uk/Departments/Physics/groups/opto/pcf.html, July 2001, accessed Jun. 11, 2002 and R. F. Cregon, B. J. Mangom, J. C. Knight, T. A. Birks, J. Russell, D. Allen, and D. J. Roberts, "Single Mode Photonic Band Gap Guidance of Light in Air," Science 1999, 285, 1537, which are expressly incorporated herein in their entirety by this reference.

The light beam is confined to the hollow core by the holes in the surrounding glass material, which looks like a honeycomb in cross-section. The doubly periodic triangular arrangement of holes creates the light stopgap. This high-n "defect" in the repeating structure acts as the core of an optical fiber. Light expelled from the periodic structure surrounding the core can only propagate along it.

The PBF's "leak" less light and carry more intense light pulses without distortion, attributes required for USP delivery systems. Another advantage to PBF's is that they are single-mode or at least quasi-single-mode. Thus, it is possible to focus tightly the light to small spot sizes.

In some embodiments, the invention may include PBF's as low-loss waveguides for FSR laser pulses with novel properties for ablation and perhaps tomography applications. Studies at the University of Bath (U.K.) have shown that these PBF's are single-mode at all wavelengths, unlike standard fibers, which become multimode at short wavelengths. See J. Knight, B. Mangan, W. Wadsworth, G. Kakarantzas, W. Reeves, A. Ortigosa-Blanch, E. Davies, T. Hedley, and P. Russell, "Photonic Crystal Fibre," http://www.bath.ac.uk/Departments/Physics/groups/opto/pcf.html, July 2001, accessed Jun. 11, 2002 and R. F. Cregon, B. J. Mangom, J. C. Knight, T. A. Birks, J. Russell, D. Allen, and D. J. Roberts, "Single Mode Photonic Band Gap Guidance of Light in Air," Science 1999, 285, 1537, which are expressly incorporated herein in their entirety by this reference. Of particular promise is that the PBF can have a large (>50 µm) core while still being single-mode. The PBF still guides light by total internal reflection as a conventional fiber because the cladding with its air holes effectively has a lower refractive index than the core.

The fiber can have a maximum energy that it can transmit without being altered or destroyed (in which the laser ablates the fiber as opposed to the tissues or cells). To ensure further that high irradiances do not damage the fiber, the light traversing through the fiber will not be highly focused. Thus, to induce ablation, it will be necessary to focus the laser light, hence significantly increasing F and H, outside the fiber. This laser spot size must then be focused to w~5-10 µm out of the fiber to increase F and H to ablate the material constructs. Two general concepts of focusing the light are available: (1) a non-integrated lens/collimator and (2) optics integrated with the fiber. A collimating lens can be attached, grown, or milled into the fiber end for collimation. Once collimation is achieved, the light can then be focused to the desired spot size. The fiber assembly can be able to deliver a more powerful laser beam of multiple wavelengths and pulse durations to ablate, cauterize, or enhance wound healing. This multiple use of fibers enables miniaturization of the device. For the latter, it is possible to use microlens and diffractive optics milled via focused ion beam (FIB).

In one embodiment, the subtractive process of the invention may include viable and tunable-$\tau_p$ lasers (from CW to USP) such as the compact GSCEL diode. This tunable-$\tau_p$ capability enables researchers and surgeons to remove material athermally using USP's, and to thermally induce coagulation around the periphery of the ablated area with longer $\tau_p$, or to work near the cusp between athermal and thermal ablation processes (1-200 ps).

Suction Technologies

During or after material destruction, it may be desirable in some embodiments to extract or remove destroyed material from the target area. For this purpose, in some embodiments the invention may include at least one material remover 300 (e.g., FIGS. 2D-2E). In one embodiment, the material remover 300 may include one or more suction channels or a concentric suction tube that may be large in comparison to optical fibers, with channel diameters ranging from 0.4-4.0 mm. Most unwanted materials can pass through tubes of this size without difficulty. However, it may become necessary to increase tube diameter as tests are performed on various tissues, which would also increase the diameter of the tip end 17 of the tool. Any other channel design or diameter may be utilized in some embodiments, as known. Another method would be to wash the destroyed tissue, which could then be vacuumed into the tubes as shown in FIGS. 9-12.

In the illustrated embodiment of FIGS. 4-7, the tool 10 comprises a tip end 17 and a spaced back end, and the at least one material remover 300 includes at least one vacuum generator (not shown), and at least one elongate vacuum channel 320. Each vacuum channel is disposed at least partially within the tool, and has a first end 322 adjacent the tip end of the tool and a spaced second end (not shown) operatively coupled to the vacuum generator.

In another embodiment, the material remover also includes a means for flushing the target area or substrate with a flushing fluid, such as water, saline solution, or any other suitable flushing fluid, as known. Flushing fluid in such an embodiment is maintained in a reservoir, which is operatively coupled to the second end of the fluid channel. When actuated by the user, a pump that is connected to the reservoir selectively pumps flushing fluid through the fluid channel or channels to the tip end of the tool to flush the target area or substrate.

In a similar manner to the dispensing system, the vacuum/suction system in some embodiments may also use retractable channels or tubing with an outer diameter of slightly more than 1 mm. These channels may be made of similar materials as those used in the dispensing tubes, which in some embodiments can allow for easy guiding down an endoscope, but also support its weight when extended out of the endoscope. Once suction is needed, the channels in some embodiments may be extended out beyond the end of the endoscope, where the vision system can acquire the position of the channels and allow the surgeon to irrigate where needed. If the channels should become clogged, the surgeon can easily remove and replace the channels. An advantage of such an embodiment is that it uses existing vacuum and irrigation equipment with only a small modification of the irrigation tubing, such as illustrated in Ref. See Medical Replacement Parts LLC, "Biopsy Channel Information Page," http://www.endoscopepartsplus.com/biopsychannels.htm, 2001, accessed Jun. 11, 2002, which is expressly incorporated herein in its entirety by this reference.

As set forth above, in some embodiments, the material remover 300 may include one vacuum channel or a plurality of vacuum channels. Alternatively, the material remover may include one or more larger concentric vacuum channels, which may be disposed near the periphery of the endoscopic head. In one embodiment, the channels are sized so that most unwanted materials can pass therethrough without difficulty. For example, in embodiments including a material destroyer 200 that utilizes USP laser ablation, byproducts are likely to be simple atomic species. These simple byproducts can be easily collected by vacuum or saline flushing with reduced risk of forming toxic compounds compared to the thermal decomposition of cellular structures. However, it may become necessary to increase diameter of the vacuum channels to remove larger tissues, which may also increase the diameter of the tip end 17 of the tool. An alternative method would be to wash the ablated tissue, which may then be vacuumed into the channels.

Temperature Control Technologies

Temperature control of the constituent materials deposited by the apparatus in tabletop, in vivo or in vitro settings may be achieved by utilizing at least one temperature controller 400 as part of the apparatus. Materials may be heated or cooled as conditions of the procedure may require. For example, temperature control may be desired to enable the user to adjust viscosity of the constituent materials, to accelerate or decelerate setting of a scaffold material, or otherwise to provide a suitable environment for delicate or temperature-sensitive constituent materials.

In one embodiment, the temperature controller 400 including a fluid bath system may be utilized as illustrated in FIGS. 10A-10C. In such an embodiment, cooling or heating fluid may be pumped via a fluid pump 405 from a temperature-controlled reservoir 410 through the void space 411 surrounding the delivery tubes and other dispensing fibers 412 in a tool bundle 415. This technique allows any selected length of the dispensing fibers to be enveloped by the thermal control fluid. In one exemplary embodiment, therefore, thermal control fluid may be passed along the entire length of the fibers in the bundle, and both ends of the bundle may be sealed with fluid seals 420. At the distal end of the bundle, a fluid return tube 425 may be cut short of the fluid seal, creating a flow loop within the bundle.

In other embodiments, fluid may be passed along some portion of the length of the fibers. These embodiments may utilize a dedicated fluid flow for temperature control, or may utilize existing fluid delivery means existing in the device and used for other purposes. For example, some in vivo and in vitro embodiments of the device may include a material remover 300 having a means for flushing the target area with a flushing fluid or to enable general rinsing or cleaning of the device, as known. The embodiments illustrated in FIG. 2 and FIGS. 5-7 are exemplary. In such embodiments, fluid in the existing flushing means may be temperature-controlled to perform the additional function of heating or cooling the constituent materials.

In other embodiments, temperature control of the constituent materials may be provided by other means. For example, one or more heating or cooling elements may be provided inside the material delivery device, or in contact with or in close proximity to the walls of the material delivery device. However, it is envisioned that any suitable heating or cooling media may be used.

The distal end of the bundle also may be provided with a temperature sensor for feedback control of the fluid pumping/temperature control system. Alternatively, sensors may be provided at other locations along the bundle, or at multiple locations as needed.

The ability to control temperature can allow the tool head to be maintained at a constant temperature if desired. Additionally, the biological material or other constituent materials delivered by the tool may be heated or cooled as desired. The heating and cooling means of the invention, however, enable the user slowly and deliberately to change the temperature of the tool head or constituent materials, while providing the temperature control functionality in an efficient means in terms of size and heat removal.

Environmental Control Technologies

In tabletop DWDT or in vitro HAT embodiments, the user may wish to control environmental conditions, e.g., sterilization, in the work area. For example, the user may wish to control oxygen content, humidity, or other environmental factors to optimize the environmental conditions of certain procedures. In such embodiments, a chamber may be provided surrounding the work area, the chamber being constructed of suitable impermeable material. (f 1). In exemplary embodiments, the chamber may be comprised of a sealed box made of a glass, a plexiglas, a plastic, or any other suitable transparent, impermeable materials adapted for use in enclosing the work area.

Additive Technologies

In one embodiment, the invention includes at least one material dispenser 100, (e.g., FIG. 2F) also referred to herein as additive technologies, for depositing at least one material on a substrate or the target area to which the user wishes to apply materials.

As discussed in detail herein, exemplary embodiments of the material dispenser 100 are illustrated in various figures, including FIGS. 11A-D and 13A-C. In the illustrated embodiments, the material dispenser 100 includes at least one elongate feed channel 120 having an inlet 122 and a spaced outlet 124. The feed channel 120 is sized and shaped to hold material to be deposited onto the substrate or target area, so that material stored in the feed channel flows from the inlet to the outlet when the user wishes to deposit materials.

The material dispenser also includes a tip chamber 102 having a proximal end 104 defining a proximal orifice 106 therethrough. The tip chamber 102 has a spaced distal end 108 defining an opening, or tip orifice 110, through which material is dispensed onto the target area or substrate. The outlet 124 of the feed channel 120 is positioned adjacent the tip orifice 110. Thus, during material dispensing, the material flows through the feed channel 120 and the outlet 124, into the tip chamber 102, then out through the tip orifice 110 and onto the substrate or target area. Material flows through the tip chamber along a material flow path extending from the proximal end to the distal end, and generally along a longitudinal axis LX through the tip chamber. As discussed in greater detail below, the tip chamber 102 has an inner surface 112 that, in some embodiments, is tapered from the proximal end 104 toward the distal end 108 such that the proximal orifice 106 is larger than the tip orifice 110. In some embodiments, that taper may be defined by angle A between the longitudinal axis LX and the inner surface 112.

The material dispenser 100 also includes a valve 130 (FIG. 11A) for controlling the flow of material through the dispenser. The valve 130 is generally moveable between an open position P1 (FIGS. 11B and 11D), in which material is permitted to flow through the outlet 124, and a closed position P2

(FIG. 11C), in which material is not permitted to flow through the outlet 124. An actuator 144 is operatively coupled to the valve 130 for selectively moving the valve between the open position and the closed position.

In some embodiments, the material dispenser 100 may include a conventional suction device for withdrawing material from the tip orifice 110 when the valve is in its closed position. As discussed in greater detail below, such a "suck back" feature may improve start/stop characteristics of the device.

In various embodiments, the material dispenser further comprises at least one location control device 800 (FIG. 36) adapted to position the tool, specifically the tip orifice, at any selected position with respect to the substrate or target area. In some embodiments, the control device controls the position of the tool in the x or y direction (i.e., a line). In other embodiments, the control device comprises a planar location controller adapted to selectively position the tip orifice within both x and y dimensions (i.e., a plane) that is substantially parallel to the substrate or target area. In yet another embodiment, the control device further comprises a linear location controller adapted to selectively position the tip orifice within the z dimension (i.e., a line) that is substantially perpendicular to that xy plane. In such embodiments, the planar location controller may be synchronized with the linear location controller so that the control device can selectively position the material dispenser 100 in xyz space (i.e., in three dimensions) as desired by the user.

As discussed in greater detail below, some embodiments of the material dispenser 100 also include a means for selectively synchronizing the location control device 800 with the actuator, to provide fine control over material dispensing.

In one embodiment, the controllers may each comprise, or may together comprise a Windows based PC, indexer, and translation system. In such an embodiment, as illustrated schematically in FIG. 36, the indexer accepts commands from the PC and computes the necessary commands that need to be sent to the translation system. Most indexers either plug-in to the PC bus or communicate with the PC via Ethernet. The indexer will preferably have a large memory cache and be capable of operating in the Khz range. The translation system is comprised of translation stages to give motion control in the required axes. The translation stages may be of the ball-screw variety. They may have associated linear encoders to improve positional accuracy but can typically operate with 1-2 um of accuracy without them. If nanometer accuracy is required, a linear stage with linear encoders may be needed. In linear stages, the external motor is not required as it is inherent in the stage itself. For ball-screw stages, a motor and a motor driver are required. In addition, the stages must be sized to carry the desired load (weight). The motor is selected to deliver the required torque for a given speed.

The signal chain is PC to indexer and indexer to motor controller resulting in motion along the required axis. Suitable location control devices and means for synchronization are commercially available. Manufacturers of suitable indexers include Compumotor, Galil, and Aerotech. Manufacturers of suitable translation stages include Parker-Dadel, Deltron, and Nu-tech. Manufacturers of suitable motors and motor drives include Compumotor, Qtech and Intelligent Motion Systems.

Through-Nozzle Design

In one embodiment, illustrated in FIGS. 11A-11D and 12A-12B, the material dispenser 100 may include a through-nozzle design, which may incorporate one or more of the following design aspects: the integration of a linear actuator 144 to control valve opening and closing; the placement of a valve 130 near the point of dispensing; the use of a suck-back valve design; a valve extension 142 that is placed between the valve 124 and the tip orifice 110 to assist in the movement of fluid during start up or shut down; integration of a tapered micro-dispensing tip chamber 102; and synchronization of the actuator 144 that controls the opening and closing of the valve 124 with substrate motion or the motion of the material dispenser 100 during the deposition process.

One embodiment of the material dispenser 100 incorporating aspects of a positive-displacement/suck-back pump system is illustrated in FIGS. 11A-11D. In this embodiment, the pump 148 powers a simple process of applying positive pressure to a material in a reservoir 149, and the flow of the material is controlled by adjusting the open position P1 and closed position P2 of the valve 130 (additional flow rates can be adjusted by reservoir pressure). The design may be easily adjusted to accommodate any type of dispensing requirement, as known.

In the illustrated embodiment, when the valve 130 is in the open position P1, the valve is positioned within the tip chamber 102 between the outlet 124 of the feed channel(s) 120 and the tip orifice 110. In the closed position P1, the valve is positioned at least partially within the outlet 124 of the feed channel(s) 120. The valve tip 134 is sized and shaped to substantially seal the tip orifice 110 against the flow of material therethrough.

The rate and degree of valve opening and closing may be dynamically controlled by using a conventional linear actuator 144 to control the valve 130, which provides a means to control precisely the rate (speed) and the degree of valve opening and closing. That is, the valving mechanism may be synchronized with the xyz motion of the dispenser.

There are at least three choices available when synchronizing the valve with the substrate motion in xyz. The actuation of the valve 130 is effectively a fourth axis, and so all moves by the substrate and valve can be together considered a 4 axis move. The valve axis with hereafter be referred to as the W axis. The first choice is to open the valve independently before any xyz motion begins, then finish opening the valve over a set xyz distance. This may be called the "distance invariant" mode (i.e., if xyz motion speed was increased the valve still opens completely at the same xyz location, albeit faster due to the faster xyz speed).

The valve 130 can be thought of as having a range of motion from 0.0 (completely closed) to 1.0 (completely open). In some embodiments, actual flow of material does not occur until about the 0.3 position, and thus 0.0 is actually well back from the point at which flow is possible in some embodiments, to allow for the "suck back" phase, discussed in greater detail below.

The first motion of the valve 130, which is valve activity occurring before xyz motion begins, is referred to as a "header routine." Header routines may be programmed and stored for each different material. The user of the dispenser may select a specific header routine and instruct the actuator 144 to follow any selected header routine. All other routines are also stored in this manner, and so a library of paste valve routines may accumulate on the machine(s) being operated.

After the header routine is complete, any necessary valve motion that needs to occur to complete the valve opening then is performed synchronously with the xyz motion. The valve has now reached "steady state" and its position is not changed until near the end of the motion or at certain "trouble spots" in the middle of a path (such as at a corner where there is too much material being deposited, the valve position can be slightly closed as the corner is being approached, and then opened again after reaching it). When nearing the end of the path, the valve goes through two phases, which are the "closing versions" of the previously described opening routines. First the valve is shut somewhat in a "position versus xyz distance" manner, then once xyz motion is complete, the valve finishes closing in a "position versus time" manner.

Another choice for valve position control is to control the amount of material dispensed per second. For the same length of line (i.e., distance) traversed twice as fast, the valve would have to open faster and farther (combined with a pressure increase if necessary) to provide the necessary flow rate of fluid to write the same thickness of line. This may be called "volumetric invariant" mode. Both modes may be susceptible to the type of material being dispensed (i.e., nonlinearities in behavior).

A combination approach is to define the speed at which the dispenser should move, and then adjust with the aforementioned techniques, primarily the "distance invariant mode" (setting valve (W) positions to be reached at certain xyz locations). As automation is increasingly implemented, the valve may be characterized over nearly its entire range of operation for any material, and so automatic "volumetric invariant mode" calibrations may provide satisfactory results.

Some embodiments of the material dispenser 100 function in a manner similar to a syringe (not shown), in which the actuation or pressure-generation point within the system is removed some distance from the tip orifice 110. While such systems are suitable for use in embodiments of the invention, the distance between the actuation point and the tip orifice in such systems results in a time delay between actuation and the start of material flow. A similar latency will exist between the time of termination of the applied pressure and the time when material flow ends. The time delay is the result of the second-order system comprised of a long flexible column of material. The column must be compressed before the actuation pressure appears at the tip orifice.

In the embodiment illustrated in FIGS. 11A-11D, the valve 130 includes a linear-actuated piston 140 that controls the position of the valve 130, the piston being operatively coupled to a miniature displacement pump 148. During the initial opening of the valve, the piston moves forward at a controlled rate, displacing any material within the tip chamber 102. Once the seal of the valve 130 has been broken, the material begins to flow and simultaneously exits the tip orifice 110. In retrospect, closing the valve creates a negative displacement or "suck back" effect. As the valve 130 begins to seal, the retraction of the piston 140 creates a vacuum and pulls the material in a reverse direction, into the tip chamber 102 from the tip orifice 110.

In this embodiment, the linear actuator 144 controls the material dispensing rate and improves start and stop characteristics by controlling the position of the valve piston 140 and speed of displacement. During the initial valve opening, the motion of the piston 140 transfers a momentum to the material and causes the material to flow at a specific flow rate. This transfer of momentum primes the material in the tip chamber 102, so that the material flowing through the valve 130 will have the same flow velocity, thereby leading to a smooth dispensing start. In conditions where the displacement is too fast, the material may be ejected without any control, which may lead to poor start characteristics (e.g., splashing, puddle formation, and voids). In conditions where the displacement is too slow, the material may be dispensed with some control, but may not have a steady-state flow characteristic upon leaving the tip orifice 110, which can lead to inconsistent volumes and inaccurate starting times. Through precise rate control of the piston opening, the initiation of material flow followed by valve opening can be smooth, seamless, and very reproducible.

In the illustrated embodiment, the valve 130 is placed near the tip orifice 110 which reduces the length of the material column, which in turn reduces the latency between actuation and material start or stop. In addition to reducing the material column length, a valve extension 142 may be placed between the valve 130 and the tip orifice 110 to assist in the movement of material during startup or shutdown. On startup, the valve extension 142 forces a volume of material toward the tip orifice 110 that is sufficient just to start the flow of material. The pressure applied for continuous flow remains on the reservoir and the tip orifice. Conversely, the valve extension 142 evacuates the small volume just inside the tip orifice 110 back into the tip chamber 102 when the reverse actuation is applied, stopping the material flow.

Some material dispensers 100 include of a large-diameter material column that terminates in a smaller-diameter material column leading to the tip orifice (not shown). This type of dispenser generates a significant pressure gradient (Δp) in the small-diameter fluid column. The Δp may exaggerate the start and stop problems described in the previous section.

Referring now to FIGS. 11A-11D, in one embodiment, the material dispenser 110 incorporates a tip chamber 102 having a gradual change in diameter between the proximal orifice 106 and the tip orifice 110. Implementation of such a tapered tip into the design may improve the flow characteristics in the system and to improve the response of the material during start and stop sequences. Providing a gradual taper to the tip chamber 102 reduces Δp approaching the tip orifice 110 and directs the material toward the tip orifice 110. The reduction in Δp enables the material to flow with less resistance, thereby improving flow characteristics and lowering the potential for clogging. With a lower Δp at the tip, opening and closing of the valve 130 occurs with a reduced latency in the start and stop of material flow.

Such tapered nozzles may reduce shear forces within materials passed through the material dispenser 100, which reduces the possibility of material (e.g., cell) damage during the deposition process. By way of analysis, it is an accepted principle of basic aerodynamics that flows bending around a corner are accelerated. For flow in a small nozzle, it can be shown that the shear force at the wall ($\tau_{s\text{-}wall}$), where it is a maximum, has the form given in Equation (1):

$$\tau_{s\text{-}wall} = -\frac{\mu}{2}\frac{\partial}{\partial r}\left(r\frac{\partial u}{\partial r}\right), \quad (1)$$

where r is the radius of the nozzle cross-section, μ is the fluid dynamic viscosity, and u is the velocity in the axial direction. Therefore, when the flow is bent around the nozzle exit, its velocity profile is skewed and the ∂u/∂r term increases, thereby increasing $\tau_{s\text{-}wall}$. Hence, the larger the bend around which the fluid must flow, the greater is the resultant increase in $\tau_{s\text{-}wall}$. In addition, as r becomes small, Δp increases, which also increases the ∂u/∂r term. So, for a given flow rate, if the average value of r (as measured from the entrance to the exit) is small, the overall pressure drop across the nozzle is expected to be large (due to the higher total friction) and the average velocity is expected to be large.

The design approach takes into account two design parameters, L (the length of the nozzle, from the proximal end 104 to the distal end 108 as shown, e.g., in FIG. 11A) and r(x) (the radius of the tip chamber at any (x) location along the longitudinal axis LX). From the analysis above, it can be noted that these two design parameters conflict. A gently varying r(x) is required to minimize the flow's "bending gradient," but this increases the value of L, which decreases the average r, thereby resulting in a higher Δp. Computational fluid dynamics (CFD) modeling may be utilized to provide optimal profiles of L and r(x) for various flow rates and viscosities, thus defining the shape of the surface 112 of the tip chamber 102 in certain embodiments.

In another embodiment (FIGS. 11A-11D, 12A and 12B), the inner surface 112 of the tip chamber 102 is substantially continuous, is substantially circular in cross section taken perpendicular to the longitudinal axis LX, and exhibits a straight taper, i.e., r(x) is a linear function in these embodiments. In one embodiment, an angle A measured from=the longitudinal axis LX to the inner surface 112 is in the range from about 20 degrees to about 45 degrees. In another embodiment, the angle A measured from the longitudinal axis LX to the inner surface 112 is in the range from about 20 degrees to about 45 degrees. In yet another embodiment, the angle A measured from the longitudinal axis LX to the inner surface 112 is about 32 degrees. For different materials, however, any selected angle A that creates acceptable shear conditions within the material is contemplated to be within the scope of the invention.

Figure 12A:
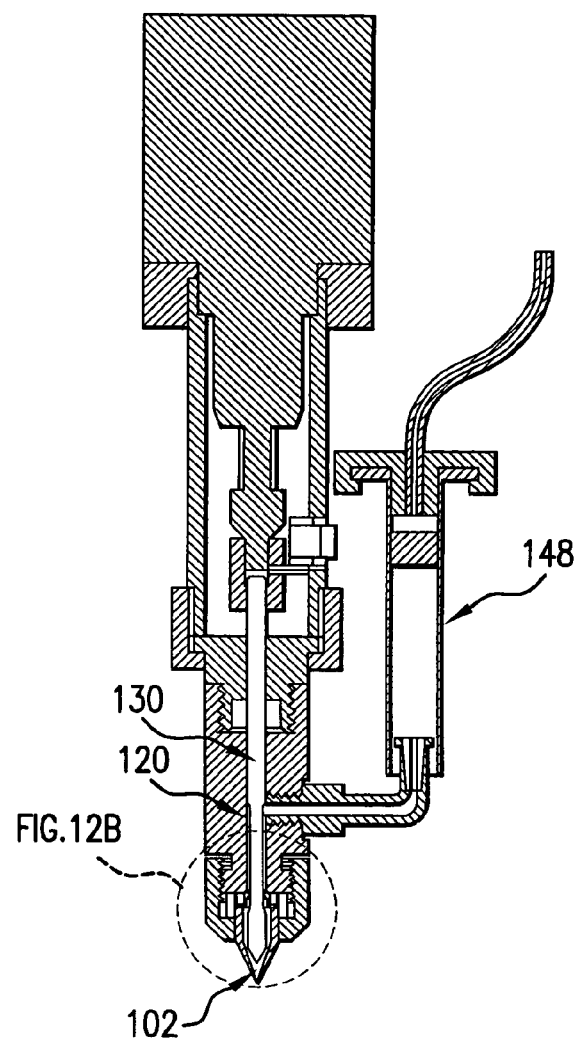
FIGS. 12A and 12B are views of an embodiment of the material dispenser of the invention.
Figure 12B:
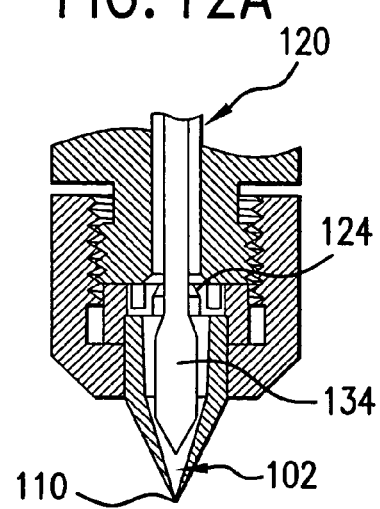

FIGS. 12A and 12B illustrate an embodiment of the material dispenser 100, utilizing a compact, optically encoded linear actuator 144 with a Nema 17 motor to actuate the piston 140 between its closed and open positions. The valve 130 forms a suck-back valve close to the tip orifice 110. In the illustrated embodiment, the tip chamber 102 is tapered to a tip orifice 110 having an outer diameter of about 25 μm and an inner diameter of about 12.5 μm.

The actuator 144, in various embodiments, may be a stepper-controlled linear actuator, a servo-controlled linear actuator, a hydraulically controlled linear actuator, a pneumatically controlled linear actuator or other actuating devices, as known.

Needle-Valve Dispensing Design Solution

Figure 13C:
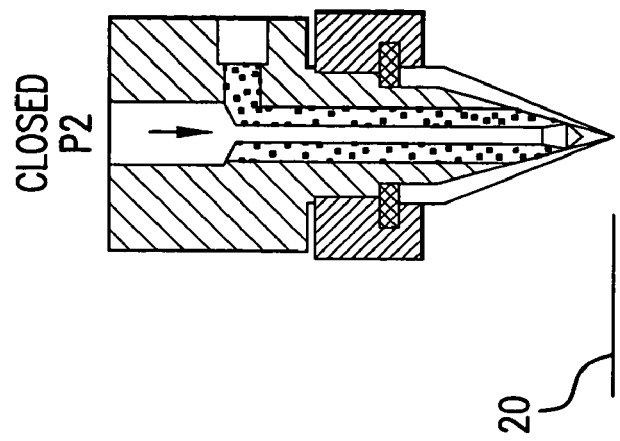
FIGS. 13A-13C are sequential operational views of an embodiment of the material dispenser of the invention.
Figure 13B:
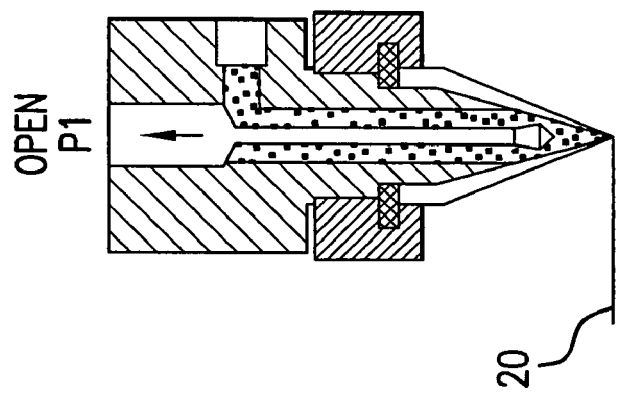
Figure 13A:
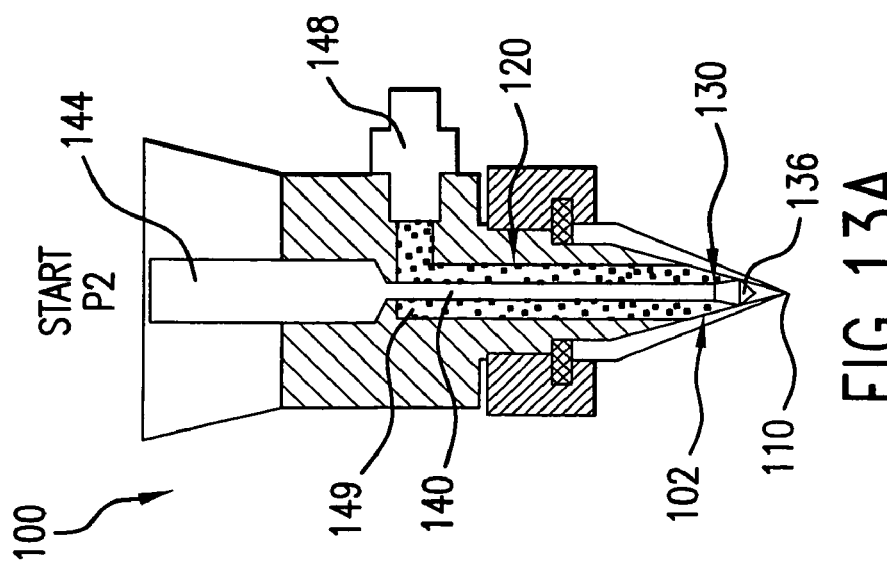

Referring now to FIGS. 13A-13C, in another embodiment, the at least one material dispenser 100 comprises a needle-valve design, in which the valve 130 comprises a needle valve 136. The needle valve design may incorporate one or more of the following design aspects: the integration of a linear actuator 140 which drives the piston 140, which is in turn connected to the needle valve 136 to control opening and closing; the placement of the valve 130 near the tip orifice 110 to reduce dead volume; integration of a tapered microdispensing tip chamber 102; and synchronization of valve actuation with xyz motion.

In one embodiment, the needle-valve material dispenser includes a pump 148 that applies a positive pressure to material in the at least one feed channel 120. Material flow through the material dispenser is controlled by adjusting the valve's open and closed positions P1, P2 (additional flow rates can be adjusted by reservoir pressure). In the open position P1, material is permitted to flow through the tip orifice 110. In the closed position P2, material is not permitted to flow through the tip orifice 110. The design can be adjusted to accommodate any type of dispensing requirement. As set forth above, the rate and degree of valve opening and closing may be synchronized with xyz motion of the material dispenser 100.

In the illustrated embodiment, the linear-actuated piston 140 controls the position of the valve 130. During the initial opening of the valve, the piston moves backward (from the tip orifice 110 toward the proximal end 104 of the tip chamber 102) at a controlled rate. Once the seal has been broken, the material begins to flow and simultaneously exits the tip orifice 110. As the valve 130 begins to seal, the flow is retarded. The unique aspect of synchronizing the valve actuator with the xyz motion of the dispenser provides fine control over start-stop characteristics.

In this embodiment, during the initial needle valve opening, the retraction of the valve 130 does not transfer momentum to the material, it merely opens the valve to the flow. Momentum is transferred to the material via pressure applied to the reservoir by the pump 148. Poor stop conditions which may result, such as splashing and puddle formation, may be overcome by using a servomotor or stepper motor or the other motor embodiments described in greater detail above as the linear actuator controlling the needle valve position in synchronization with respect to the target area or substrate.

As discussed above, in one embodiment, the valve 130 is located close to the tip orifice 110 to reduce latency between valve opening and material dispensing.

Sensoric Quill-Pen Dispensing Design

In another embodiment, the at least one material dispenser 100 comprises a sensoric capillary- and/or quill-pen, in which a constituent material such as a cell suspension or slurry would function as "ink" for the dispenser. In the embodiment illustrated in FIG. 19, the capillary tube 115 communicates a material supply chamber 116, such as a supply, reservoir, or feeder for storing a sufficient volume of the constituent material. The "sensoric" feature of such quill-pens enables the tool to sense and maintain optimum contact with the deposition target while the constituent material is being dispensed from the dispenser as discussed in greater detail below.

Miniaturized Positive-Displacement Dispensing Design

In yet another embodiment, the at least one material dispenser 100 may comprise a pumping system capable of dispensing a single material, or a plurality of discrete materials. In one embodiment, a MIS-compatible HAT deposition head may have an array of dispensing units to deposit, the scaffold material, cells, growth factors, enzymes, saline wash, and a vacuum for extraction, as desired, and constructed as illustrated in FIGS. 5-7 (9-12). Each feed channel 120 within the dispenser may have its own reservoir that is remotely actuated to dispense a material through the feed channel. The integration of feed channels close to the dispensing nozzles minimizes void volumes of scarce cells and bioactive compounds. The material in the discrete feed channels 120 may be individual materials, e.g., hydrogel, stem cells, growth factors. Alternatively, the material may be a combination of materials, e.g., hydrogel that is commixed with stem cells, nutrients, proteins, growth factors, and other materials. As discussed above, the material dispenser 100 in some embodiments may include means for minimizing shear forces within the materials during dispensing.

Figure 14:
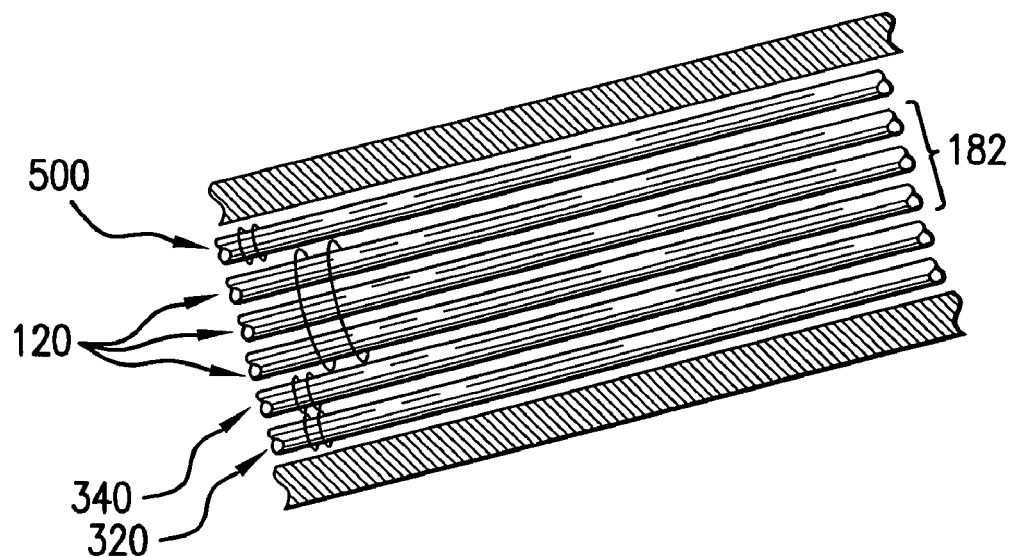
FIG. 14 is a perspective view of an embodiment of an insertion bundle for use the material dispenser of the invention.

In one embodiment, the material dispenser 100 includes at least one feed channel 120, each feed channel being operatively coupled to at least one pump 148. As shown in FIG. 14, a plurality of feed channels 120 may be packaged as part of an insertion bundle 182. This concept allows the user to exchange a bundle of feed channels 120 for optical fibers, vacuum tubes, or a combination of all functionalities as needed. Each insertion bundle 182 may be removed and replaced with another insertion bundle or other functionalities depending upon the specific application. In an in vivo embodiment of the invention, for example, once the tip end of the tool is inserted into the body, the insertion bundle 182 within the tool can be easily interchanged to dispense multiple types of materials. Without moving the tip end of the tool, various components of the tool may be extended, actuated, and retracted as desired. (FIGS. 6A and 6B). Changing the insertion bundle 182 does not require removing the tool once it is inside the patient. The endoscopic tip end of the tool may "find" the desired area or position of interest.

Various types of pumps 140 may be utilized according to the invention. In one embodiment, the pump may be a linear piston pump, an augur pump, a pressure reservoir pneumatic pump, or other suitable design(s). In various embodiments, the pump 140 may be driven by a stepper-controlled or servo-controlled linear actuator. Besides a stepper motor, pneumatic or hydraulic activated configurations may also be used, or other pumping means that enable control of material flow.

FIGS. 15A-15D illustrate a sequence of steps in which the material dispenser 100 is inserted into the tool and actuated to dispense a preloaded material. In the illustrated embodiment, the material dispenser 100 including the pump 140 is inserted into the tool 10, which may be introduced into the body. Upon full insertion, the feed channel 120 may be extended to dispense material through its outlet 124. The outlet 124 may then be directed to a specific target area where the material is to be deposited. Once the outlet 124 is in position, the pump displaces the working fluid or a flexible rod in the feed channel 120, thereby depositing the material in a controlled manner. After dispensing, the feed channel 120 may be retracted and the material dispenser 100 may be removed from the tool.

Each feed channel 120 may be independently controlled, such that the user may select and control the flow rate of each feed channel 120 independently. In one embodiment illustrated in FIGS. 29A-29C, this objective may be accomplished by providing each feed channel 120 with an independent pump to drive material flow. In other embodiments, each feed channel may be provided with an independent valve controlling egress of material from the feed channel. In still another embodiment, a combination of independent pumps and independent valves may be provided to refine further control of individual feed channels.

In another embodiment, the pump assembly uses a flexible positive-displacement pump. Since the diameter of the feed channel may be small (≈1 mm) and may use low-viscosity materials, a stainless steel or plastic rod can be used as a piston 140. Dispensing is accomplished by pushing the material through a small-diameter flexible feed channel.

Referring now to FIG. 14, the feed channels may be designed to slide into one of several dispensing ports that are a part of the insertion bundle 182. The dispensing ports in the bundle then allow several fluids to be dispensed through discrete feed channels, and allow for the discrete feed channels to be retracted and reinserted or replaced. Once extended beyond the distal end of the bundle, the placement of the feed channels may be monitored and controlled by feedback from an imaging device 500 (e.g., FIGS. 4, 5 and 7), if provided. After insertion into the field of view of the imaging device, the feed channels may be clamped into a location control device 800 (FIG. 36) and precisely located as desired. Driving input to the location control device may be computed from input from the imaging device 500. Rinsing fluids may be pumped down the extent of a fluid channel 340, if provided, or unwanted materials can be drawn into a vacuum channel 320, if provided.

FIGS. 5-7 illustrate a miniaturized dispensing nozzle with a plurality of individual channels. In the middle of the assembly is a needle valve 136 for controlling deposition of materials through the material dispenser 100. As illustrated, the material dispenser 100 has a distal end 108, which may be selectively extended beyond the tip end 17 of the tool.

In embodiments of the invention having multiple feed channels within the material dispenser, additional control over the flow of the constituent material through the feed channels 120 may be provided by discrete valves at the outlets 124 of each feed channel 120. In all such embodiments, the plurality of feed channels 120 may be provided with the valve 130 positioned downstream of fluid channel outlets 124 that enables precise control over material flow through the tip orifice 110.

The feed channels 120 may be comprised of any suitable material, including plastics (e.g., Teflon®). An important issue when dealing with surgical procedures is the sterility of the process. In many embodiments, the feed channels may be small in comparison to a typical syringe. It is not common practice to wash syringes once they have been contaminated with fluids or biological materials; following this practice, the feed channels may be disposable.

The feed channels 120 may be formed together with a nozzle 126 adjacent the outlet 124, or a loading port 128 formed adjacent the inlet 122 and in one piece as shown in FIG. 16. As with a typical syringe, the material may be loaded into the feed channel before being inserted into the body, and the feed channel may be primed with material, the air removed, and set volumes of fluid material dispensed. As discussed above, the feed channel or set of feed channels can comprise an insertion bundle 182 and can be slid into the material dispenser 100. This can be done at any time, with the tool within or out of a body.

Figure 17B:
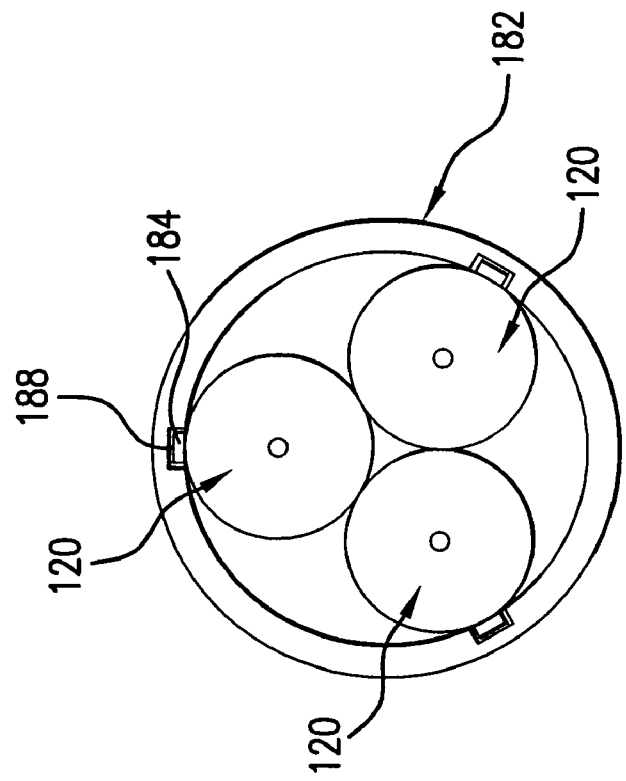
FIGS. 17A and 17B are views of an embodiment of an insertion bundle for use with the embodiments of the material dispenser of the invention.
Figure 17A:
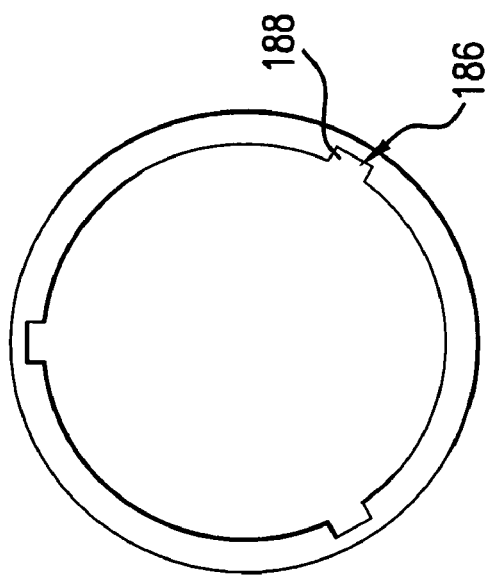

In yet another embodiment, specially designed double- and triple-insertion bundles 182 may be fabricated, following the same concept as the single disposable feed channel 120. Again, these may be filled with fluid and all air may be removed before insertion into a body. FIGS. 17A and 17B illustrate a double and a triple-channel configuration, respectively. The insertion bundle 182 is sized and shaped to be selectively removable from the tool and replaceable with a second insertion bundle. In the illustrated embodiment, the insertion bundle comprises a first alignment component 184, which is one or more set keys 188 formed or positioned on the outer perimeter of the insertion bundle. The material dispenser 100 also comprises a second alignment component 186, which in the illustrated embodiment is comprised of one or more set grooves 190 that is complementary in size and shape to the first alignment component. The first and second alignment components fit together to position the insertion bundle in a desired orientation within the material dispenser. The keys may be positioned on the insertion bundle and the grooves on the material dispenser, or vice versa, as desired.

In yet another embodiment, syringe technology may be used to connect to a manifold. Vibration, stirring, mixing, or simple combined-flow operations may be done within the manifold. The output of this system also allows a selection of materials to be used, thus allowing for layering or scaffolding of designed cells for optimal growth and performance. The complete system is flexible enough to allow biologists, physiologists, and physicians to mix various materials for deposition or simply to remove unwanted materials in vivo. The tool can be automated for accurate control using detection feedback. It can have a manual override for specialized procedures by researchers or physicians.

Figure 25:
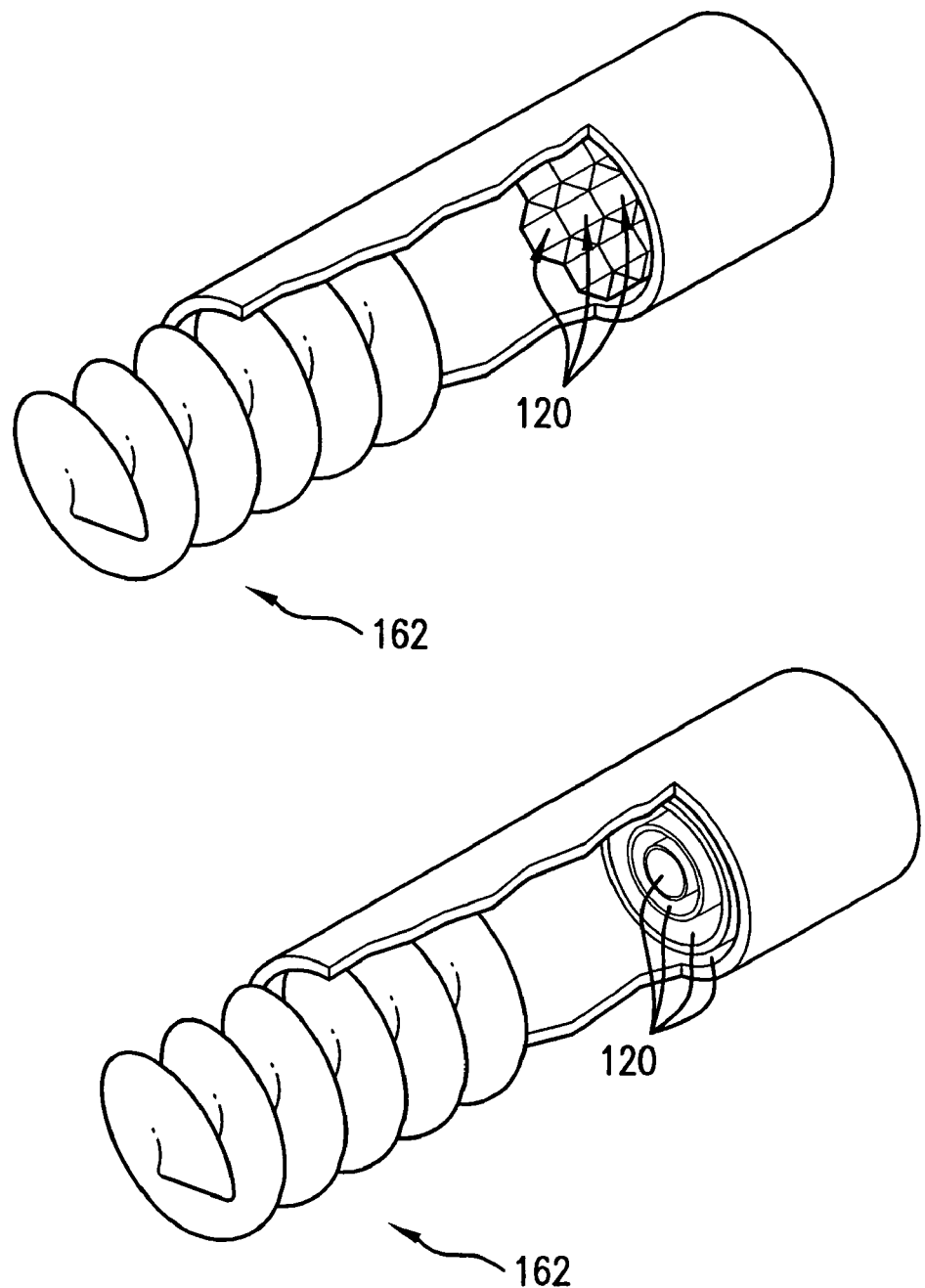
FIG. 25 illustrates two embodiments of an augur screw mixer for use with the embodiments of the material dispenser of the invention.

Embodiments of the DWDT/HAT utilizing a single material dispenser 100 or a plurality of dispensers are currently contemplated. For example, in one in vivo embodiment, the tool has a single dispenser containing multiple discrete feed channels 120 for carrying discrete constituent materials to the tip end of the dispenser for deposition at the target area. In such an embodiment, the dispenser may be constructed from a variety of different designs. For example, the dispenser may be constructed in a coaxial sleeve design, such that the multiple feed channels are formed as separate concentric cylinders defining a plurality of annular voids there between for carrying discrete constituent materials. (FIG. 25). As another example, the dispenser may be constructed in a packed-array design. In such embodiments, the dispenser may comprise a single outer sleeve encompassing a plurality of discrete neighboring feed channels. The plurality of feed channels may be arranged in generally parallel relation to one another, or may be braided or otherwise intertwined as desired by the user. Additionally, the individual feed channels may be of any suitable cross-sectional shape, including, but not limited to, a round, a hexagonal or any other desired shape(s). (FIG. 25).

In other embodiments, the tool may include multiple discrete dispensers. Each dispenser may itself contain multiple feed channels within a single dispenser as described above. Alternatively, the multiple dispensers may be dedicated to delivery of a single constituent material, or some combination of dedicated and multiple-constituent material dispensers may be included within a single embodiment of the tool. Thus, tabletop in vitro embodiments of the tool may be constructed in various ways. In one embodiment, the tool may contain only a single dispenser capable of dispensing multiple constituent materials similar to the in vivo embodiments described above. In another embodiment, the tool may contain multiple discrete dispensers, each dispenser capable of dispensing a plurality of materials. In still other embodiments, the tool may be limited to a single dispenser capable of dispensing only a single constituent material, may include a plurality of such single-material dispensers, or may contain some combination of multiple- and single-material dispensers. The user may construct any of a wide variety of tool configurations to meet the specific needs of the application.

The dispenser can have an array of feed channels to deposit scaffold material, cells, growth factors, enzymes, saline wash, and the like, and a vacuum for extraction. Each feed channels within the dispenser can have its own material reservoir that is remotely actuated to dispense the material. The integration of feed channels close to the tip orifice is one approach for minimizing void volumes of scarce cells and bioactive compounds. The fluid in the feed channels may comprise individual materials, e.g., a hydrogel, stem cells, and growth factors. Alternatively, it may contain a combination of materials, e.g., a hydrogel commixed with stem cells, nutrients, proteins, growth factors, and other materials. In such embodiments, the dispensing process may be sufficiently mild that deposited cells or surrounding cells are not harmed.

Figure 23C:
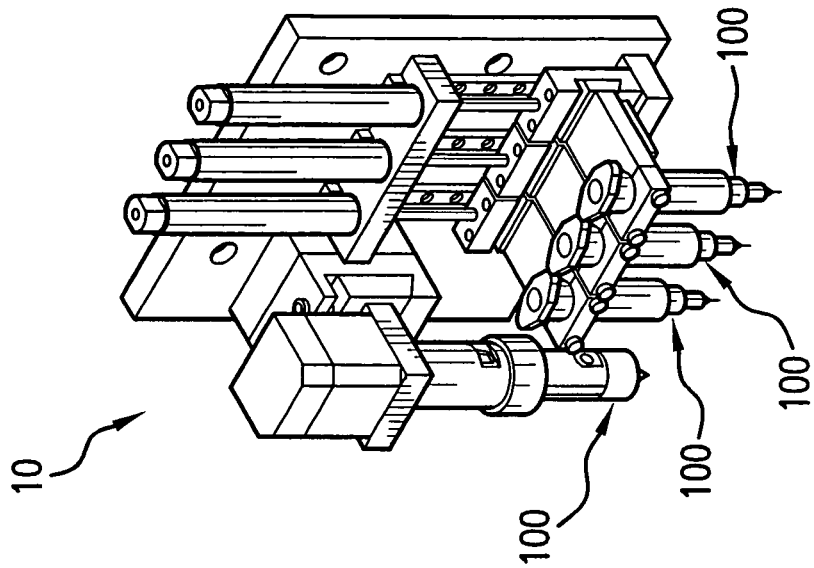
FIGS. 23A-23C are separate views of an exemplary embodiment of the invention having a plurality of material dispensers.
Figure 23B:
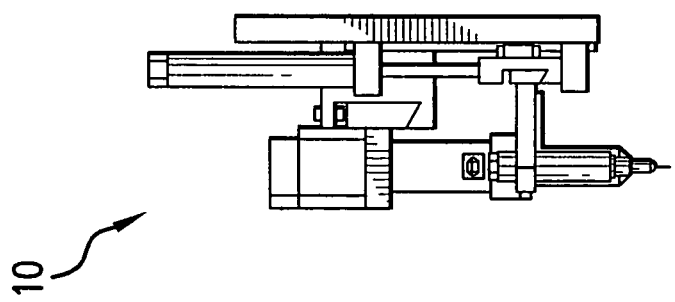
Figure 23A:
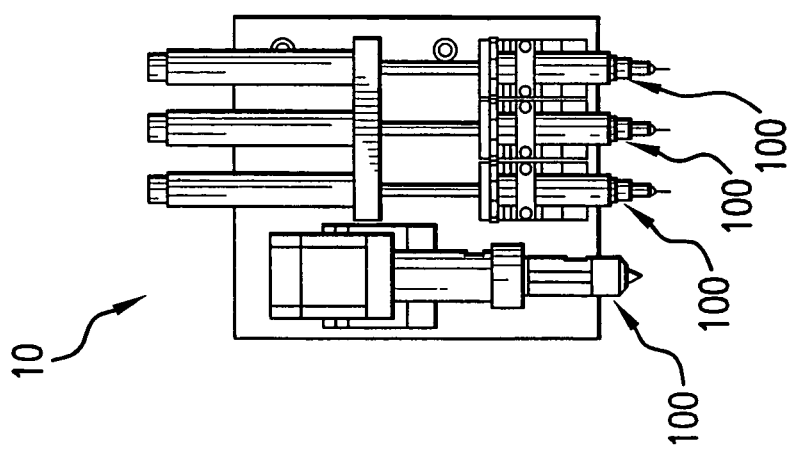

One specific embodiment of the tabletop in vitro tool design is now described in detail and illustrated in FIGS. 23A-23C. As illustrated, this embodiment includes four material dispensers, one through-nozzle dispenser and three capillary-based dispensers. In this embodiment, the through-nozzle dispenser includes a 25-200-μm conical tip attached to a suck-back spool valve, which may be used for more-viscous fluids. The capillary dispensers include >100 μm small capillary pen tips that may be used to dispense lower-μ solutions and/or cell suspensions. Each dispenser is independently controlled to deposit a predetermined amount of material. In the illustrated embodiment, the larger conical through-nozzle dispenser fills and dispenses larger areas with higher-μ materials, while the smaller capillary dispensers are retracted. When smaller detail and/or less-viscous materials than those possible with the conical through-nozzle tip are required, or if a different medium is needed, then a capillary dispenser can be extended into position to do its intended high-detail and high-precision dispensing. The capillary dispensers are mounted in a syringe that is jacketed with aluminum to provide the maximum amount of heat transfer. The jacketed aluminum syringe may be clamped into position with an aluminum tube clamp. The dispensers in the illustrated embodiment have been designed to extend and retract, so that only one dispenser is writing at a time; however, it is possible to have multiple dispensers writing at one time.

The capillary dispensers in the illustrated embodiment may be extended via a pneumatic air cylinder with a proportional control valve controlling extension and retraction speeds. A slight positive pressure may be applied to the capillary feed channels via pneumatic tubing (not shown). However, flow from the capillary dispensers in this embodiment is primarily controlled by capillary surface tension when the tip almost touches the substrate surface. The capillary dispensers may be extended on precision linear bearings to achieve a constant, repeatable, and accurate position. The entire assembly may be mounted to high-precision linear stages to move the respective dispensers into position as needed and to provide fine height adjustments.

Material dispensers may be provided in any of a wide variety of designs according to the invention, which were described in detail earlier. Each of the described embodiments may be utilized or adapted for use in either in vivo or in vitro embodiments of the tool.

In embodiments wherein a single dispenser 100 carries multiple distinct constituent materials, such as the packed-array and concentric-tube embodiments discussed above, separate valves may be provided for each feed channel to independently control the flow of each material into the tip chamber 102. For example, in packed-array designs, a rotating circular valve structure with defined "holes" or geometric configurations may be incorporated to control the passage of material through the feed channels. Such a structure would resemble the rotatable plate covering on many disposable condiment containers, for example those of salt-and-pepper shakers or grated-cheese containers. Valve control in such an embodiment could be provided by an array of electromagnets surrounding the rotatable valve, or by other suitable means.

In concentric-tube dispenser designs, similar individual valve control is also contemplated according to the invention. In one embodiment, a plurality of flat plate rings may be provided, each ring being sized and shaped to block material flow through one or more individual annular passages in the concentric channel. The individual rings may be mounted in the dispenser by any suitable means, such as by fixing individual rings to a post or axle external of the concentric feed channels and allowing the rings to rotate into and out of position at the outlet 124 of the feed channels.

System and Method for Controlling the Position of One or More Elements of a Dispensing System Using Force Feedback The present discussion is directed to a system and method for controlling a dispensing system. More particularly, the present component system is directed to a method and system for controlling the position of one or more elements of a dispensing system using force feedback.

As dispensing systems are widely used to deposit materials onto substrates, for proper deposition some knowledge is required of the intensity of the contact force between the dispenser tip and the surface where deposition is desired. Improper prediction of the intensity of this force may result in either destruction of the dispenser or the substrate as the tip crashes into the substrate material, or little to no control of the deposition geometry due to a large spacing between the tip and the substrate surface.

Tactile sensors including piezoelements have been used in atomic-force microscopes, quartz microbalances, and other devices in which it is important to determine the intensity of contact force between elements. Normally, piezoelements work as part of a self-tuning resonance system; i.e., the resonance frequency ($f_r$) is the parameter that is measured and monitored. To achieve higher $f_r$ values, which are advantageous with respect to reactivity and sensitivity, designers seek to miniaturize devices. This is not always convenient even if possible.

Therefore, a need exists for a system and method for controlling the position of one or more elements of a depositing system that accurately determines the intensity of the contact force between a dispensing tip and a substrate surface to maintain a desired contact force between the dispenser and the substrate.

The present invention is directed to a system and method for controlling the position of one or more elements of a dispensing system to maintain a desired contact force between the elements.

According to exemplary embodiments, vibration of particular amplitude (A) is imparted to one or more of the elements of the dispensing system. The vibration may be imparted to the dispenser, the substrate, or both the dispenser and the substrate. A change in the amplitude of vibration (ΔA) of the dispenser, the substrate, or both the dispenser and the substrate upon contact with each other, is detected by the system. This ΔA may be a change in amplitude of the primary harmonic vibration of the dispenser or the substrate, selected secondary harmonics of either, or combinations. The position of one or more of the elements is varied, based on the detected ΔA, to maintain a desired force of contact between the dispenser and the substrate. The positions of the dispenser, the substrate, or the dispenser and the substrate may be controlled in this manner.

According to exemplary embodiments, the system is sensitive enough to maintain a desired contact force between the dispenser and the substrate and even between material protruding from the dispenser and the substrate.

The objects, advantages, and features of the present invention will become more apparent when reference is made to the following description taken in conjunction with the accompanying drawings.

According to exemplary embodiments, a system and method are provided for controlling the position of one or more elements of a dispensing system. For illustrative purposes, the system and method may be understood as functioning in a manner analogous to a human hand that performs a physical action and maintains spatial orientation at the same time as using tactile capability.

Figure 18:
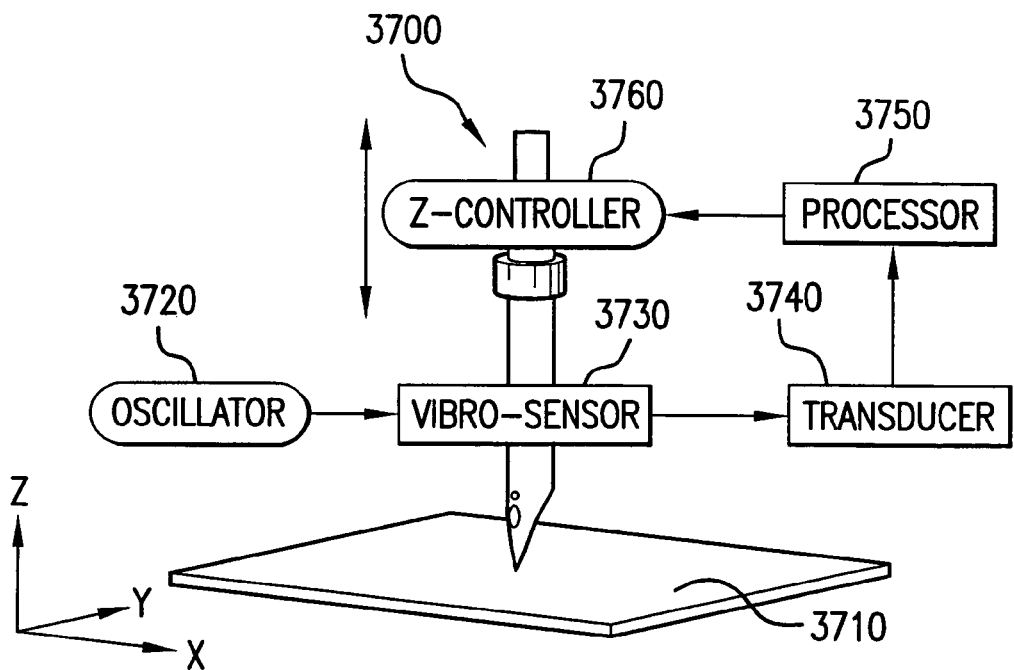
FIG. 18 is a schematic illustration of an exemplary system for dispensing materials using feedback to control the position of a dispenser according to one embodiment.

In a first embodiment, the position of a dispenser relative to a substrate is controlled. For example, FIG. 18 illustrates an exemplary system for controlling the position of a dispenser 3700 relative to a substrate 3710. Although the substrate 3710 in FIG. 18 is shown as being flat for ease of illustration, the substrate may have irregular surfaces. The dispensing system, by varying the position of the dispenser 3700 relative to the substrate 3710, enables the dispenser to follow irregular or curved surfaces.

The dispenser 3700 dispenses material on the substrate 3710 in a desired pattern. The material dispensed can include, for example, electronics materials or biological materials. The dispenser 3700 may be implemented differently, depending upon the application.

Figure 19:
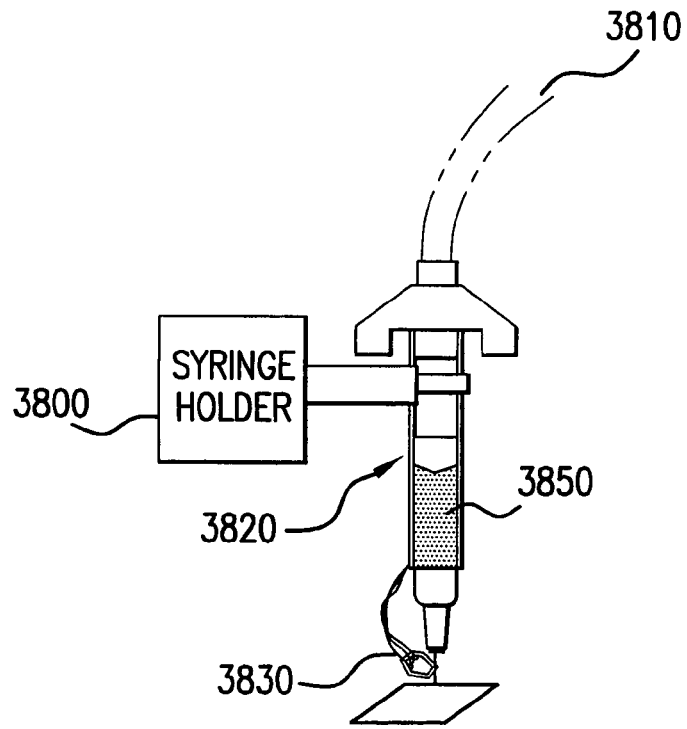
FIGS. 19, 20A and 20B are views of various elements of exemplary dispensing systems in detail.

For example, capillary vibro-sensor dispensing units, such as that depicted in FIG. 19, may be used, e.g., to facilitate both intermediate-density gelatinized slides and high-density plain and patterned slides of human white blood cells (WBC's). FIG. 19 illustrates in detail aspects of an exemplary dispensing system including a capillary dispenser held by a syringe holder 3800 and a piezomembrane 3830. The piezomembrane 3830 may be implemented with an electroceramic sensor and include a vibration actuator and vibration transducer, described in more detail below. This type of dispenser forces, e.g., fluid or paste, in a reservoir 3850 through the tip 3840 of a syringe using air pressure applied from a source 3810 to the top side of a plunger 3820. Capillary dispensers are capable of precise deposition, e.g., depositing a monolayer of cells; or depositing mono- or multilayered drawings of electronic elements and circuits, such as capacitors, inductors, and filters, on curved surfaces, etc. However, capillary dispensers may be prone to sudden clogging.

FIG. 19 illustrates in detail aspects of an exemplary dispensing system including a capillary dispenser and a piezomembrane. The piezomembrane includes a vibration actuator and vibration transducer, described in more detail below.

According to one embodiment, a noncontact, high-accuracy (submicrometer) fiber optic sensor may be used as the sensor element to monitor vibration. According to this embodiment, the sensor element may be decoupled from the dispenser assembly, allowing for reuse of the sensor element (i.e., the sensor is not required to be disposable).

Figure 20A:
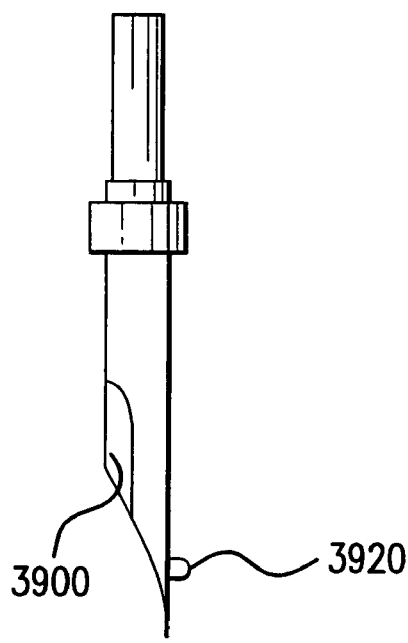
Figure 20B:
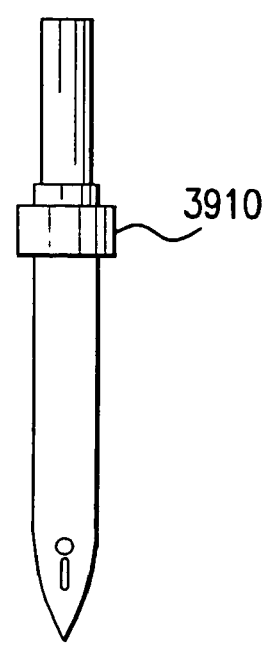
Figure 21:
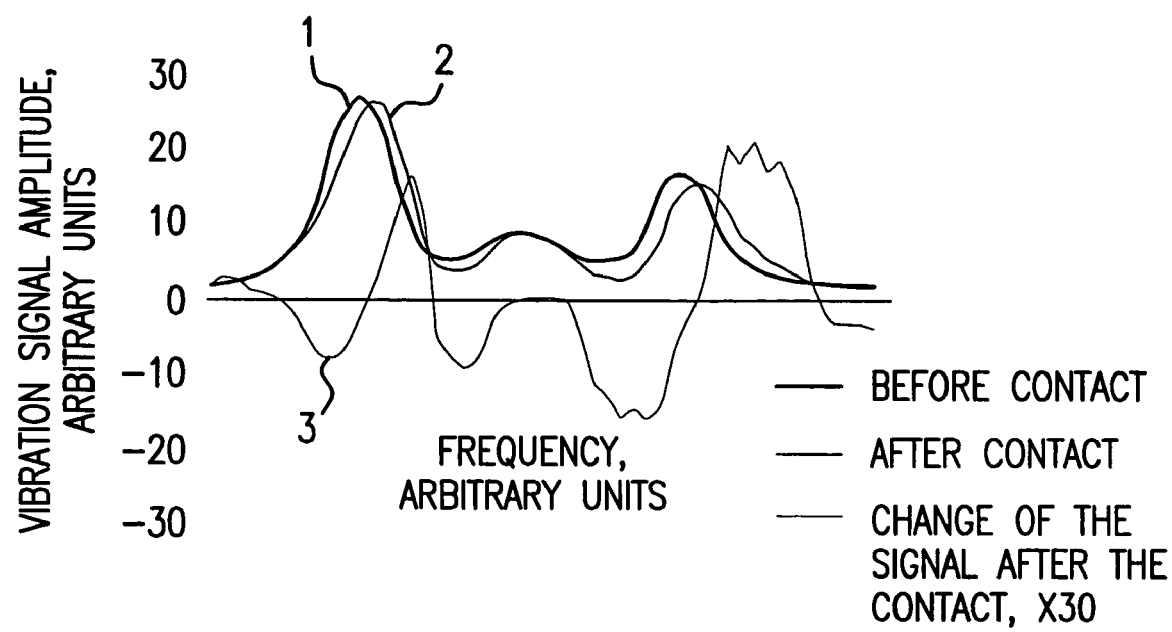
FIG. 21 is an exemplary graph of vibration $\Delta A$ vs. $\Delta f$ before and after contact between a vibrating element and another surface.

As another example, a quill-pen may be used, in which a cell suspension or slurry functions as "ink." An exemplary quill-pen is shown in detail in FIGS. 20A and 20B. These dispensers include a reservoir 3900 for the "ink". Vibrating the dispenser at, for example, low f, facilitates dispensing of the ink, thus overcoming issues regarding agglomeration and/or sticking of the cells. For illustrative purposes, the quill-pen is shown in FIGS. 20A and 20B as being part of a dispensing unit including a vibration actuator 3910 and a vibration transducer (receiver) 3920, as described in more detail below.

The material dispensers illustrated in FIGS. 19, 20A and 20B are shown by way of example only. The dispenser 3700 need not be limited to these implementations. In addition, the dispensers shown in FIGS. 19, 20A and 20B are not limited to being implemented in the system shown in FIG. 18.

Referring again to FIG. 19, a vibration oscillator 3720 is attached to the dispenser 3700 for imparting vibration to the dispenser 3700. A vibration sensor 3730 and a transducer 3740 are attached to the dispenser 3700 for sensing the A and f of vibration of the dispenser 3700. The oscillator 3720 and the transducer 3740 may be implemented with any suitable conventional devices. These elements may be spatially and physically separated or may be attached, e.g., to the same piezoceramic plate or membrane as shown, for example, in FIGS. 20A and 20B. According to one embodiment, these elements may be implemented in a piezoelectric bimorph ceramic element. Moreover, as shown in more detail, in FIGS. 20A and 20B, these elements may be included within the dispenser 3700. However, it will be appreciated that the actuator and the transducer need not be included within the dispenser. Furthermore, the actuator and/or the transducer may be included in dispensing systems employing other types of dispensers.

According to an exemplary embodiment, the vibration-actuating oscillator 3720 is activated by a function generator (not shown) that generates a vibration signal at a particular f and A. According to one embodiment, a high-f, low-A signal is generated by the function generator. For example, the function generator may employ a sinusoidal driver operating in the $90 \leq f \leq 100$ kHz range at P<1 W. Although it is considered a separate element, the function generator may be incorporated into the same element as the actuating oscillator 3720 and/or the transducer 3740.

The vibration imposed on the dispenser 3700 is changed, e.g., modulated, by the contact of the 3700 dispenser with the substrate 3710. The transducer 3740 senses and transfers the changed vibration signal to an amplifier (not shown), which then creates a feedback signal that is generally proportional to the intensity of the physical contact of the dispenser 3700 with the substrate 3710. The amplifier may be implemented with any suitable conventional device, e.g., an AD621 instrumentation amplifier. The feedback signal is used to control the position of the dispenser 3700 to maintain a desired force of contact between the dispenser 3700 and the substrate 3710. For example, the feedback signal may be used by a z-controller processor 3750 to control the z positioning of the dispenser 3700 via a z-controller step motor 3760. A personal computer (PC) may be used in conjunction with the z-controller 3750 for this purpose, in which case the feedback signal is fed directly to the PC.

The z-controller 3750 may be implemented with, e.g., a microprocessor, and the step motor may be implemented with any suitable conventional device, e.g., a Whisper™ Model 44103 Bipolar Drive. The amplifier and the z-controller 3750 may be separate elements or may be incorporated into the element(s) including the actuating oscillator 3720 and/or the transducer 3740.

According to exemplary embodiments, the vibration imposed by the function generator does not necessarily have to occur at $f=f_r$ of the piezoelement or the dispensing system. This brings additional flexibility and sensitivity to the system and permits it to expand significantly its f range. Systems of considerable size (from a fraction of an inch to inches) have been shown to work at frequencies up to $f\sim100$ kHz.

In addition, instead of monitoring the vibration f, according to exemplary embodiments the vibration A is monitored. Measurement of A generally provides the same sensitivity as does the measurement of f or period (t). If a bell-shaped resonance of frequency f and quality factor Q experience a small shift $\Delta f<<f/Q$, then $\Delta A$ measured at half-height of the resonance line is about $\Delta A/A \sim Q(\Delta f/f)$. If $\Delta f/f \sim 10^3$—a reasonable short-term stability threshold for a piezoelement resonance—and $Q\sim 50$, then $\Delta A\sim 5\times 10^2$, which is usually above the noise level for a piezotransducer. The minimal registration time is approximately the same for both registration schemes, i.e., of the order of one vibration period. However, when a vibrating element contacts an object, it does not necessarily shift $f_r$. In contrast, A is inevitably altered.

This $\Delta A$ can be understood with reference to FIG. 40, which illustrates graphs of $\Delta A$ in relation to $\Delta f$ at arbitrary A and f. The plots shown in FIG. 40 represent $\Delta f$ and $\Delta A$ of a complex vibration element, such as a dispensing system with a piezoelement attached. Plot 1 shows the relationship between A and f before physical contact of the vibration element with another surface, and Plot 2 shows the relationship between A and f after physical contact of the vibration element with the other surface. Plot 3 shows the absolute value of the relative $\Delta A$. The measured $\Delta A$ are widespread throughout the vibration spectrum, often staying apart from resonance lines. This enables the selection of a working f in a desirable region not limited by the self-resonance of piezoelements.

Another advantage of imposing vibration is that it is possible to observe $\Delta A$ on subharmonics and, especially, superharmonics, employing synchronous phase-sensitive detectors and f of the function generator as a standard. This may provide even better sensitivity and flexibility.

In the exemplary system shown in FIG. 18, a control method using dispenser motion relative to the substrate is used. This may be achieved by mounting the dispenser to a balanced coil driven in a bipolar fashion, thereby allowing the dispenser to move in relation to the substrate while maintaining sufficient dispensing or writing force. This method allows the use of multiple dispensers on a single substrate, since each dispenser has independent feedback.

Figure 22:
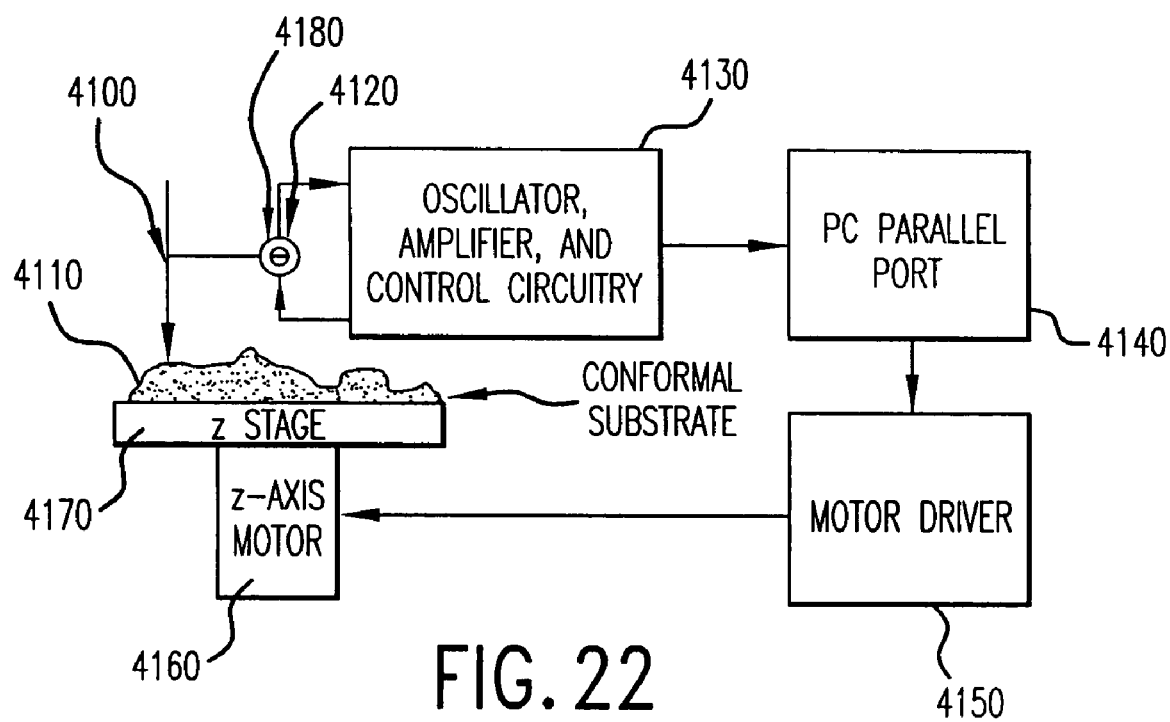
FIG. 22 is a schematic illustration of an exemplary system for dispensing materials using feedback to control the position of a substrate of an alternative embodiment.

Alternatively, a system for controlling substrate motion relative to a dispenser may be used, such as that schematically shown in FIG. 22. The active feedback system shown in FIG. 22 utilizes an element 4120, attached to the dispenser 4100, to provide indication of contact with the substrate 4110 upon which the material is being dispensed with the dispenser 4100. The system illustrated in FIG. 22 is similar to that shown in FIG. 18, with similar elements that may be implemented in a similar manner. For example, the dispenser 4100 may be implemented as described above with reference to FIG. 18.

In the system shown in FIG. 22, an oscillator, an amplifier, and a control circuit are combined in the element 4130, which may be a bimorph ceramic element. Alternatively, these components may be included in separate elements. Additionally, one or more of these components may be included as part of the dispenser 4100. The oscillator included in the element 4130 operates in a manner similar to the function generator described above to deliver a driving signal to the dispenser 4100, causing it to vibrate at $f_r$ of the dispensing system. A feedback signal is sensed by a transducer and an amplifier included in the element 4130 and sent to the control circuitry within the element 4130 for control of the position of the substrate 4110, e.g., the height relative to the dispenser 4100. The transducer and amplifier may be implemented in a manner similar to that described above with reference to FIG. 18. The control circuitry may include, e.g., a microprocessor.

When the substrate 4110 contacts the dispenser 4100, the vibration f spectrum of the dispensing system is changed, and the A of the feedback signal changes. This change is sensed and processed by the electronics unit 4130 and sent, e.g., to a PC 4140. According to one embodiment, the PC 4140, in conjunction with the control circuitry, controls the direction and speed of the z-axis stage 4170 upon which the substrate 4110 rests. Alternatively, the control circuitry may perform this function without the use of a PC.

Using the motor driver 4150 to drive the z-axis motor 4160, the position of the z-axis stage 4170 is changed relative to the dispenser 4100 to affect the vibration A so that A of the feedback signal is maintained at a constant level, thereby closing the feedback loop. According to one embodiment, the resolution of the system may be determined by the maximum speed and resolution of the z-axis stage 4170, since the substrate 4110 is moved relative to a fixed dispenser 4100.

Figure 22A:
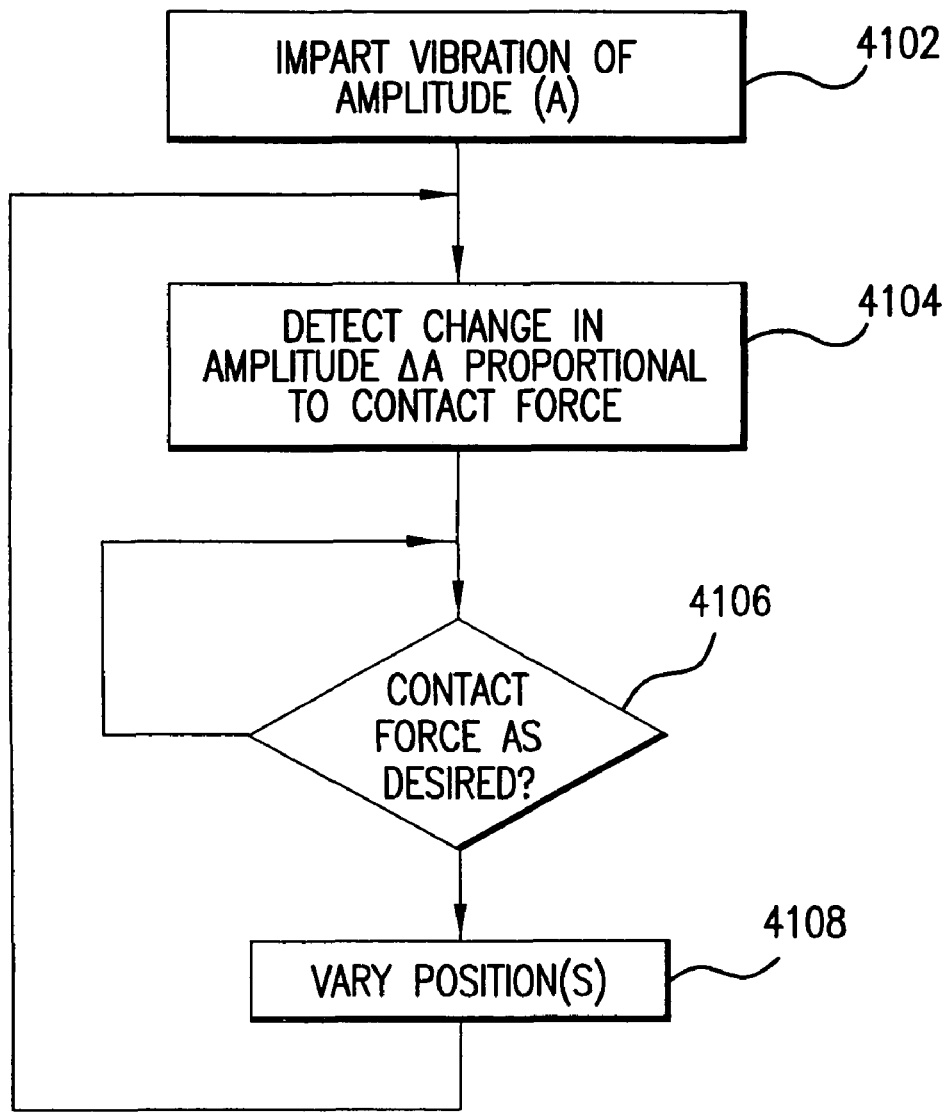
FIG. 22A is a flow chart of an exemplary method of controlling the position of the elements of a dispensing system.

FIG. 22A illustrates an exemplary method for controlling the position of one or more elements of a dispensing system including at least one dispenser and at least one substrate. The method begins at step 4102 at which vibration of a particular amplitude is imparted to the dispenser and/or the substrate. At step 4104, a change in the amplitude of vibration of the dispenser and/or the substrate is detected. This change in amplitude is proportional to the force of contact between the dispenser and the substrate. At step 4106, a determination is made whether the contact force is that which is desired, based on the detected change in amplitude. If the contact force is that which is desired, the process may stop, or this step may be repeated to ensure the contact force remains as desired. If at step 4106 it is determined that the contact force is not as desired, the position(s) of the dispenser and/or the substrate are varied at step 4108, causing a change in the amplitude of vibration. This change in amplitude is detected again at step 4104. Steps 4104, 4106 and 4108 are repeated as necessary to obtain a desired contact force between the substrate and the dispenser, e.g., to maintain contact of a desired force between the substrate and the dispenser, seek contact between the substrate and the dispenser, or break contact and seek contact again.

According to exemplary embodiments, a system and method are also provided that are capable of determining the point at which any form of contact between the dispensing tip and the substrate surface occurs. The force of contact between the dispensing tip and the substrate surface applied is controlled by a feedback measurement system.

According to one embodiment, a source of vibration is applied to the dispenser. A vibration sensor is also attached to the dispenser to sense A or f of the applied vibration. The A of the sensed vibration is then altered, e.g., modulated by the dispenser as it contacts the substrate. The amplitude of the modulation in the signal is proportional to the force applied between the dispenser and the substrate. The modulated vibration amplitude signal is then used as feedback to control the contact force between the dispensing structure and the substrate surface.

Control applied in this manner allows for dispensing to be accomplished onto conformal surfaces as the force feedback control continuously corrects the dispensing structure's z-height position as the z height of the substrate surface changes, either by modifying the dispenser's position, the substrate's position, or both. This enables the writing of fine lines, e.g., 20 µm wide, and writing on curved surfaces, e.g., placing electronic elements on a cylinder. Control applied in this manner also enables the dispenser to seek and find contact with a surface, maintain contact of a desirable intensity, accurate to a precision of micronewtons of force, if not smaller units of force, and to break contact on command and find it again. The system has been demonstrated to be sufficiently sensitive to allow for the sensing of the contact force as a dispenser contacts a substrate surface and even as the material protruding from a nozzle on a dispenser contacts the substrate surface.

In the embodiments discussed above, the change in vibration applied to the dispenser is used as a feedback signal. However, the same result can be achieved by applying the vibration source to the surface of the substrate material while sensing the ΔA transferred to the dispenser or by sensing the ΔA that occurs at the substrate upon contact with the dispenser. The result can also be achieved by applying the vibration source to the dispenser and sensing the A transferred to the substrate surface.

The dispensing system described above may be implemented as part of a multiunit system, such as that shown in detail in FIG. 22.

Embodiments of the Biological HAT Dispensing System

In appropriate situations, tissue engineering begins with a biocompatible scaffold that acts as a framework for the subsequent cell growth and proliferation. Under such circumstances, tissue engineering involves either seeding preformed porous scaffolds with host cells, growth factors, enzymes, antibiotics, and perhaps other bioactive substances, or blending of all ingredients in a fluid matrix (i.e., hydrogel), which is allowed to solidify within a support structure. In either case, the resulting composition is homogenous and provides no ability to achieve reproducibly a predetermined spatial orientation. This initial fabrication process is followed by culturing and subsequent implantation of these scaffolds into a person to direct the growth of new tissues.

HAT embodiments for in vivo use transform the "fabricate, cut, and paste" in vitro method into one that enables the surgeon to build from within the human body in vivo. To do this, the bioscaffold can require 3D fabrication processes to replace the targeted tissue using a microstylus dispenser. HAT overcomes many of the current tissue-engineering limitations by simultaneously depositing cells and cofactors with the scaffold material during the scaffold synthesis process. The HAT technology places a tissue-manufacturing process in the hands of a surgeon to fabricate scaffold microstructure with controlled spatial gradients of cells, growth factors, and other desired ingredients.

Cellular Deposition with Vibro-Sensoric Capillary Dispensers

In experimentation with one embodiment of a capillary vibro-sensoric dispenser in an in vitro application, the Applicants have fabricated both intermediate-density gelatinized slides and high-density plain and patterned slides of human white blood cells (WBC's). The cells have an areal density (a) in the range of $(0.5-1.0) \times 10^6$ cm$^{-2}$. This embodiment of the dispenser is able to deposit a monodisperse layer of cells. Capillary vibro-sensoric dispensers as illustrated in this embodiment possess tactile properties that enable them to follow and to cover curved surfaces.

Vibro-sensoric quill-pen, through-nozzle, capillary, and needle-valve dispensers may all be used for cellular deposition. Conventional inkjet dispensing technology, including pressure-driven and thermal inkjet dispensing techniques, may also be utilized in the HAT design for dispensing material constituents. However, some ink-jet dispensing units may be inappropriate for use with certain constituent materials, such as materials containing live cellular components, because destructive thermal or mechanical forces may be applied to the materials during propagation from the ink-jet head.

Surface Modifications for Monodisperse Cell Deposition

Figure 24:
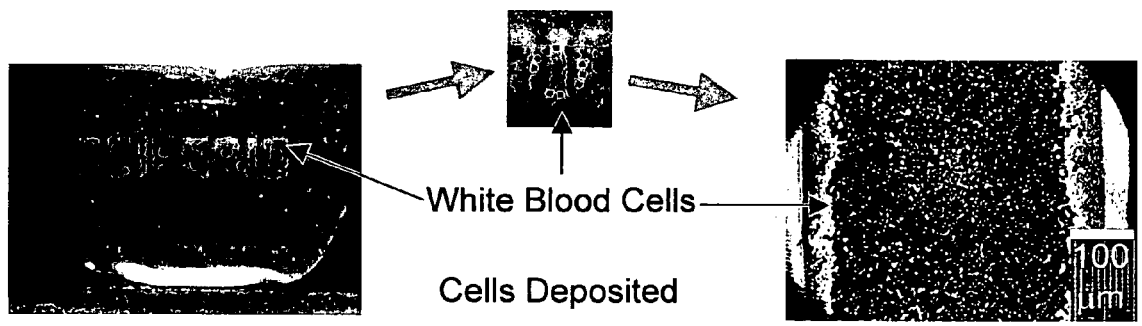
FIG. 24 illustrates views of white blood cells deposited on a substrate using an embodiment of the invention.

It has been found that a PPF-co-PEG hydrogel surface is useful as a DWDT/HAT substrate due to its high hydrophilicity and water-absorption capability for a cell deposition surface without a gelatinized layer. In one specific example, a cellular suspension is deposited onto a dry hydrogel-coated slide. After mild drying, water in the suspension is absorbed by the hydrogel. Cells become attached to the hydrogel surface by van der Waals forces. The hydrogel acts as a fast water absorber, and a water reservoir as well, preventing the total drying of the adsorbed cells. The hydrogel swells, deforms, and sometimes peels away upon absorbing water. Therefore, to preserve the geometric and optical properties of the slide, the shape and the placement of the top hydrogel layer should be fixed via photo-crosslinking to an underlying plastic layer of higher strength and significantly lower water-absorbing capacity. Alternatively, a surface layering process may be used to overcome swelling or peeling of the hydrophilic surfaces from glass surfaces to allow monodisperse cell deposition. Experimentally tested hydrogel slides contained up to four different layers, e.g., from bottom to top: glass substrate, polyurethane, PPF, and PPF-co-PEG hydrogel. FIG. 24 shows optical micrographs depicting a monodisperse layer of cells deposited onto such a layered surface using the vibrosensoric capillary dispensing system.

Other surfaces can be used as well to enable monodisperse cellular-deposition via DWDT/HAT, individually or in combinations. Examples include nitrocellulose membranes and slides, metals, micromachined-patterned surfaces, and anion- and cation-exchanging surfaces.

Mixing Nozzles

In various embodiments, the DWDT/HAT may incorporate several dispensing nozzle variants within the material dispenser 100 to change fluid/material constituents in a rapid and facile fashion, and to ensure proper "mixing" of said material constituents. In one embodiment, a line-vision feedback system or integrated sensing function may be provided to monitor, calibrate, and control the change of material constituents "on the fly." If no mixing of discrete constituent materials is necessary, individual dispensers without mixing nozzles may be used for layer-by-layer and side-by-side deposition of as many different materials as dispensers are incorporated into the tool. In another embodiment, discrete material dispensers may be "snapped" on or off the tool to change and combine materials "on the fly," under manual change mode, or as a computer-controlled cartridge-clip system. In yet another embodiment, fiber-optical illumination of the target area after material deposition will provide photonic crosslinking of various materials or laser sintering, which in many cases can be milder than chemical solidification.

Development of various electronic, chemical, material, or engineered-tissue constructs will require the deposition of multiple materials. These materials may be deposited all at once or in an ordered sequence. The ability for in-line mixing also realizes a miniaturized chemistry plant. However, regardless of the order of deposition, it may be necessary in some embodiments to perform mixing of the constituent components as close to the tip orifice as physically realizable to reduce dead or void volume. Therefore, the invention includes, in some embodiments, an in-line mixer capable of mixing a variety of materials of various densities and viscosities.

In some embodiments, the mixer is capable of handling fluid densities of at least $700 \leq \rho \leq 1,400$ kg/m$^3$ and viscosities of at least $10^{-3} \leq \mu \leq 10^3$ Pa s. Fluid flow rates will be in the range of at least $10^{-12} \leq U \leq 10^{-6}$ L/s. In various embodiments, the mixers minimize the shear stresses ($\tau_s$) induced on the materials (especially the biological fluids) and are capable of mixing the resulting slurry to any level of mixing, from completely separate materials to a homogeneous solution.

Each of the material dispensers of the current invention may also include any of a wide variety of stirring or mixing devices for mixing the constituent materials passed through the dispenser. Such stirring or mixing devices may be particularly desirable within the tip chamber 102 of dispensers designed to dispense a plurality of discrete constituent materials, such as a single dispensers that dispense scaffolding material, growth factors, therapeutics and other materials. Such mixers may be disposed between the outlets 124 of the respective feed channels 120 and the tip orifice 110.

Mixing Through Vibratory Transducers

In one embodiment, stirring or mixing may be accomplished using one or more vibratory transducers to facilitate the flow of the constituent material from the dispenser. For example, the tip chamber may also be vibrated at high-A low-f (f~100 Hz) to overcome issues regarding agglomeration and/or sticking of the constituent material. In another embodiment, the mixer includes at least one vibration imparting device for imparting vibration to the dispenser at the tip chamber, at least partially between the output ends of the respective feed channels and the tip orifice. The vibration imparting device may be a vibratory transducer, such as the transducer described above for use in force feedback tool positional control.

In yet another embodiment, the transducer generates oscillations at amplitudes greater than about 10 nm and at frequencies less than about 100 kHz; and in still another embodiment, the transducer generates vibratory oscillations at amplitudes of about 10 nm and at a frequency of about 100 kHz. Other amplitudes and frequencies may be suitable for use in alternate embodiments.

The Lagrangian dynamics of passive fluid flow can produce chaotic behavior even under a laminar flow regime at low Reynolds numbers (Re). Because this so-called chaotic advection phenomenon does not depend on high local rates-of-strain, it is particularly attractive for mixing biomolecular materials prone to shear-induced strain. In designing a mixing cavity that relies on chaotic advection, some general rules of thumb are: nonmixing regions have causes—more energy does not imply more mixing; symmetry impedes mixing; and steady flows are poor mixers. See H. Chate, et al., *Mixing: Chaos and Turbulence* (New York: Kluwer Academic/Plenum Publishers, 1999), which is expressly incorporated herein in its entirety by this reference.

Mixing can be achieved by stirring and by the wide range of mixing devices in use in the chemical, pharmaceutical, petroleum, and food industries, for example. At small dimensions (centimeter and below), mixing by stirring becomes ineffective and difficult to achieve because the Reynolds number is so low (Re<1). The low Re indicates that the flow is laminar; thus, turbulent mixing is prohibited. Therefore, mixing via diffusion with a static mixer may be effective for mixing on centimeter and smaller size scales. Static mixing does not incorporate any moving parts; mixing is not obtained by external agitation, but rather by the motion of the material as it flows through the geometrically designed mixing elements. With static mixers, the requirement for internal or external motors is eliminated, resulting in a relatively low-cost device. Furthermore, sealing problems may be eliminated and product loss and undesirable ingress of air may be avoided in a static mixer. Static mixers are fabricated from most metals and plastics to fit pipes and vessels of virtually any size and shape. Static mixers in the macroscopic scale are used for mixing high-$\mu$ liquids and liquids with extremely diverse viscosities. Static mixers may be configured to prevent excessive mixing and to minimize shear forces, which is significant for biological constituent materials that can be damaged by the larger shear forces created in certain actively stirred configurations.

Mixing Via Auger and Helix Configurations

Several specific embodiments of active and static mixers suitable for use according to the invention are now described in detail. In one embodiment, a screw augur 162 (FIG. 25) may be provided to mix constituent materials exiting from a dispenser. FIG. 25 illustrates such an embodiment as applied to a plurality of feed channels 120 within a single dispenser having either a concentric-tube configuration or a honeycomb-packed-array configuration. The screw configuration on the periphery of the interior of the nozzle enhances mixing. A screw-augur mixing nozzle may also be incorporated with other dispenser designs described herein. Additionally, the screw augur nozzle may be provided in an active, i.e., rotationally driven, or static configuration. Embodiments are contemplated in which the augur screw comprises a pitch at least in the range of from about 30° to about 90°.

Figure 26:
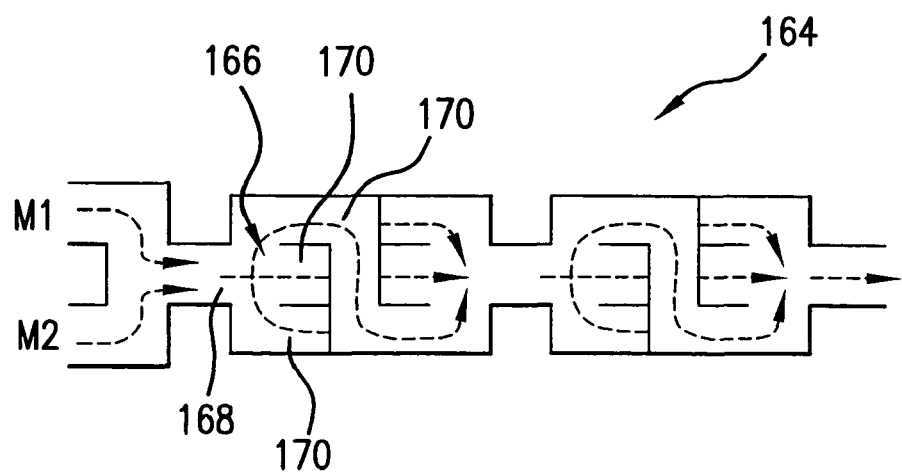
FIG. 26 schematically illustrates an embodiment of a branch-and-recombine mixer for use in the embodiments of the material dispenser of the invention.

Another static mixing embodiment is the branch-and-recombine configuration as shown in FIG. 26. In such an embodiment, discrete materials M1, M2 entering the mixer encounter at least one branch point, the at least one branch point comprising a primary channel that branches into at least two secondary channels therefrom. Those channels may, in one embodiment, be formed as a series of rigid elements that form intersection channels to split, rearrange, and/or combine the various component streams. In other embodiments, the branch-and-recombine mixer comprises a plurality of such branch points.

For mixing, it may be desirable to allow a sufficient length of flow to assure good mixing, which in turn may lead to a slight "lag" in reaction time for the system. This lag may require a compensating subchamber.

Figure 27A:
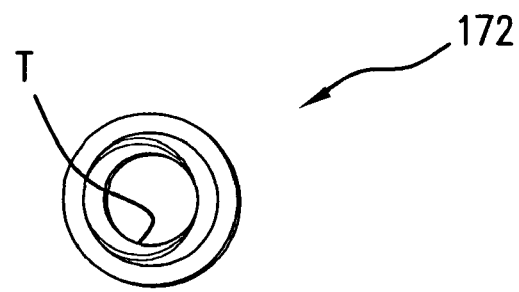
FIG. 27A is a top plan view of a helix channel mixer for use with the embodiments of the material dispenser of the invention.
Figure 27B:
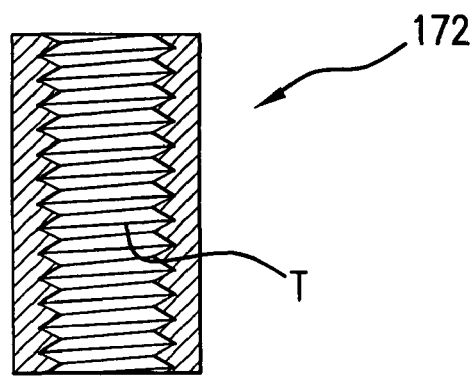
FIG. 27B is a cross-sectional elevation view of the helix channel mixer of FIG. 27A.

In another embodiment, a combination of intersecting channels and helix elements may also be utilized. A mixing nozzle as illustrated in FIGS. 27A and 27B may be made of any suitable material, including stainless steel and navy brass material (which provides high corrosion resistance), and manufactured to a small diameter. Left-hand and right-hand embodiments are contemplated. Additionally, as shown in the illustrated embodiment or FIG. 27B, one end of the nozzle is threaded with a right-hand thread and the other side is threaded with a left-hand thread. The outer diameter, length, and pitch dimensions may be adjusted as needed to provide more or less mixing effect. The left- and right-hand threads intersect about the diameter, creating a mixing regime. In one embodiment, the helix channel comprises a pitch in the range between about 30 and about 60 degrees.

In other embodiments, fractal- or random-based geometries may be utilized to promote mixing. Fractal-based geometries to enhance mixing have been studied as superior replacements of turbulence for mixing. See H. Chate, et al., *Mixing: Chaos and Turbulence* (New York: Kluwer Academic/Plenum Publishers, 1999), which is expressly incorporated herein in its entirety by this reference. Companies such as Amalgamated Research Inc. have already developed fractal-based static mixers. See Amalgamated Research Inc. (Twin Falls, Id.), http//www.arifractal.com/, 2001 (accessed Mar. 5, 2002), which is expressly incorporated herein in its entirety by this reference. A fractal shape exhibits "self-similarity," i.e., it is symmetrical regardless of scale. Thus, even after magnifying the fractal geometry an infinite number of times, the shape still appears the same. Random geometries have also produced acceptable results in mixing nozzles. Mixing flow geometries may be further optimized for various material constituents using evolutionary computation-based codes such as genetic algorithms.

Miring Via Enhanced Diffusion and Pulsing

The diffusion process can be accelerated via lamination. See J. Branebjerg, P. Gravesen, J. P. Krog, and C. R. Nielsen, "Fast Mixing by Lamination," in *Proceedings of the IEEE Ninth Annual International Workshop on Microelectromechanical Systems* (Piscataway, N.J.: IEEE, 1996), 441, which is expressly incorporated herein in its entirety by this reference. The approach will be to have the fluids enter the mixing chamber side by side through thin slits. The increased diffusion surface area contact and thinness of the fluid layers will greatly accelerate the diffusion process and aid in "premixing" into the mixing chamber.

Figure 28A:
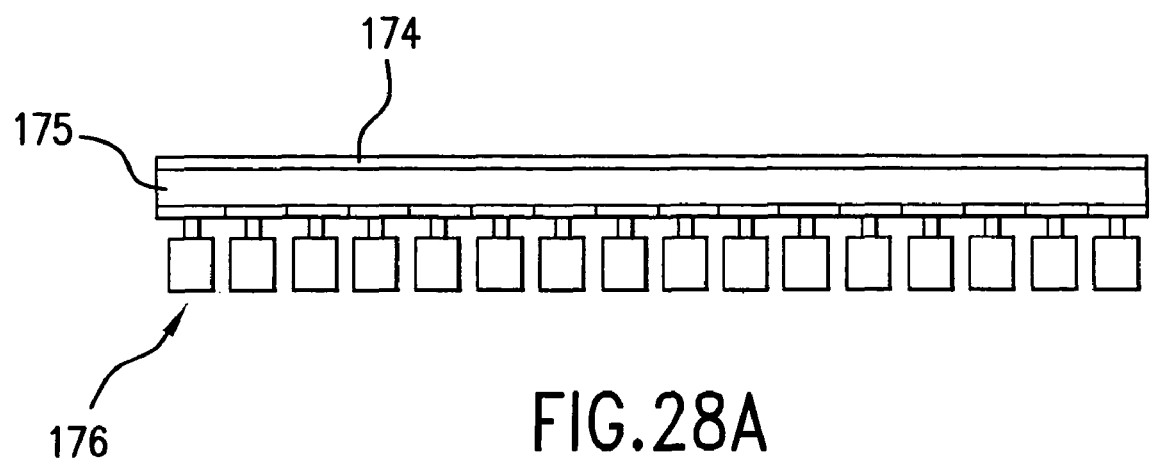
FIGS. 28A and 28B are views of an embodiment of a mixing chamber for use in an embodiment of the material dispenser of the invention.
Figure 28B:
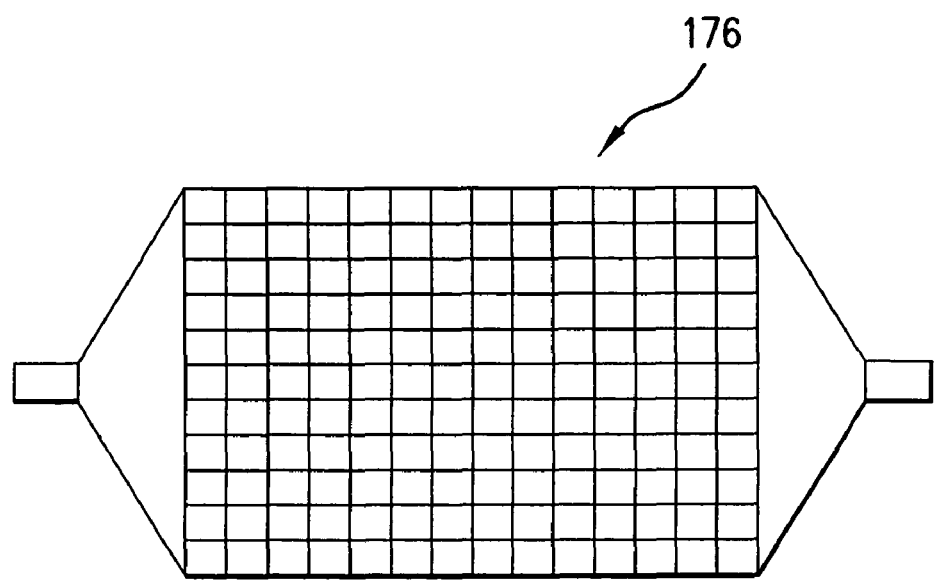

While turbulence cannot be generated at such low Re, chaotic advection can be generated. See J. Branebjerg, P. Gravesen, J. P. Krog, and C. R. Nielsen, "Fast Mixing by Lamination," in *Proceedings of the IEEE Ninth Annual International Workshop on Microelectromechanical Systems* (Piscataway, N.J.: IEEE, 1996), 441, which is expressly incorporated herein in its entirety by this reference. Neglecting diffusion, the streamlines of a laminar flow never cross. Therefore, running the flow "in reverse" (reversing the sign of the boundary conditions) will bring particles (of negligible mass) back to their original positions. In a chaotically advective process, "bifurcations" occur and the flow becomes irreversible in that the particles end up in entirely different positions. This process can be generated by input flow pulsing and dynamic mixing geometries. In addition, the problems associated with mixing a wide range of fluid properties can be overcome using real-time optical feedback to observe and control the mixing process. A mixing chamber suitable for implementing this approach is illustrated in FIGS. 28A and 28B. FIG. 28, which is a side view, illustrates a top support plate 174 that may be transparent to facilitate optical inspection. A pliable membrane 175 is positioned below the top support plate, and above an array 176 of mechanical actuators for generating dynamic geometries. FIG. 28B is top plan view of such a mixing chamber.

This approach will allow for dynamic mixing geometries with minimal shear stress induced on the fluids. Pulsed input to the mixer along with the localized movement of the bottom wall provides multiple degrees of freedom for mixer configurations. However, it is very unlikely that a single sequence of mechanical actuator activation will be suitable for all combinations of fluids that will be mixed. Therefore, the use of an optical feedback-control input to optimize the actuator activation sequence over a wide range of fluid properties is contemplated, as discussed in greater detail below.

As mentioned, in one embodiment, mixing may be enhanced through enhanced diffusion. One method of enhancing diffusion is by increasing the surface area (contact area) of the materials to be mixed. Multiple inlets with high surface-to-volume ratios are utilized in one embodiment. Multiple inlets in an integrated nozzle are utilized in another embodiment.

Figure 29A:
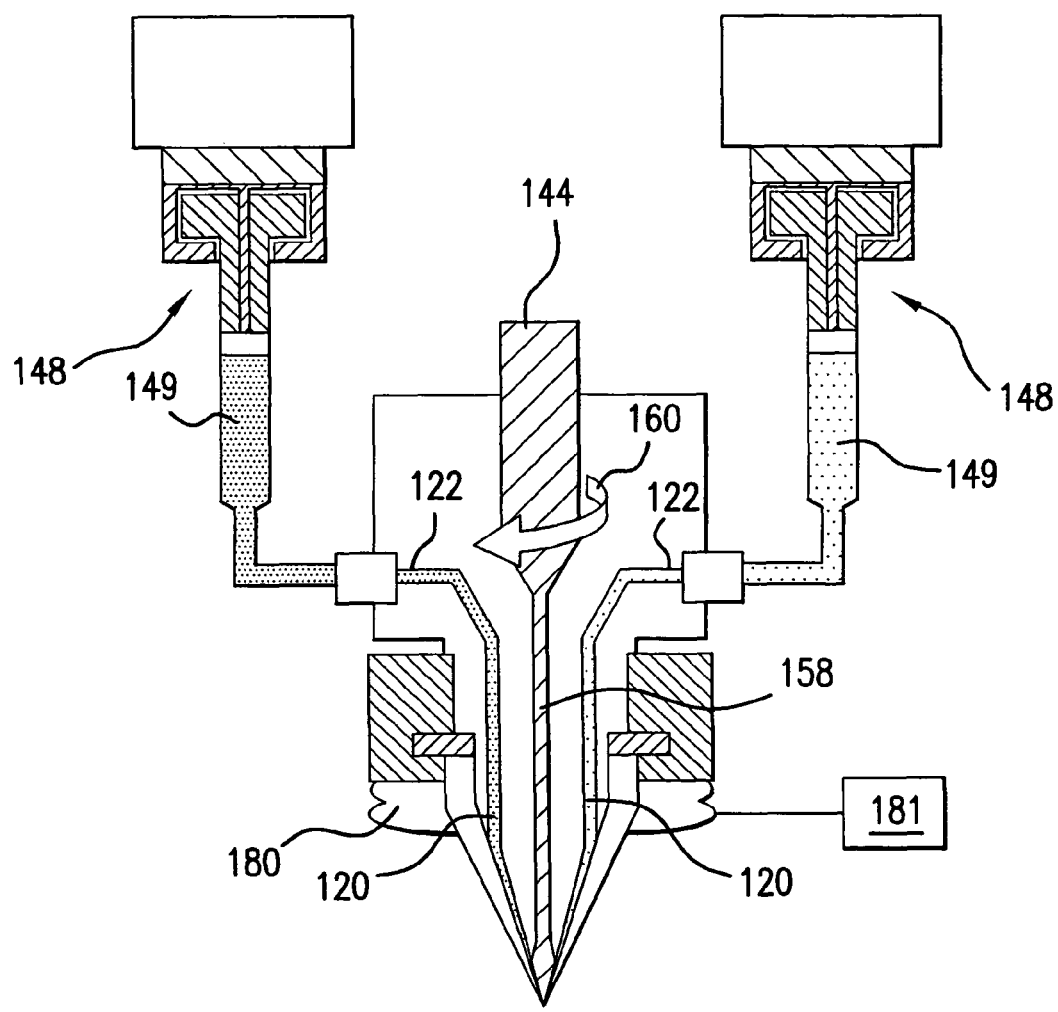
FIGS. 29A-29C are separate views of a rotating needle valve embodiment of the material dispenser of the invention.
Figure 29B:
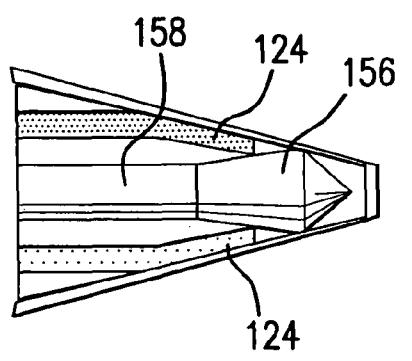
Figure 29C:
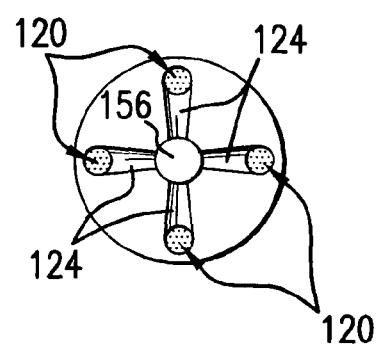

FIGS. 29A-29C illustrate a needle-valve configuration with four fluid inlets integrated into the tip chamber 102; however, the integrated multiple-channel tip chamber configuration could be used in any of the material dispensing configurations discussed herein. The needle valve is controlled via a motion-controlled linearly actuated piston, as discussed above. The four material inlets are also independently controlled with stepper- or servomotors, or pneumatic and/or hydraulic pumps. FIG. 29C shows a top view of the mixing nozzle in which the four materials are to be mixed within the tip chamber.

The multiple outlets 124 of the feed channels 120 are configured to increase contact area between the materials to be mixed. In the illustrated embodiment, the outlets 124 of the respective feed channels are disposed in a staggered configuration within the tip chamber, each outlet being spaced from each adjacent one of the outlets by a substantially equal distance. The illustrated embodiment also features high surface areas of the inner surface 112 for providing an increased contact area between the materials and thus increased mixing thereof. The illustrated embodiment also features a tapered tip chamber for low shear forces as discussed in greater detail above. Also featured are integrated displacement pumps for deposition of controlled volumes. An example of such a pump is illustrated in FIG. 29A, in which each material or fluid constituent is independently controlled. Each pump may be pulsed to further increase-mixing, either in-phase with other pumps, or out-of-phase, or combinations thereof. Additionally, the length of the pulses may be varied to further promote mixing. The integrated multiple-material valve may be optimized with respect to maximized surface-to-volume ratios and minimized pressure drops. Such pumps in the illustrated embodiment also provide the ability to modulate the pressure of the constituent materials.

Figure 30:
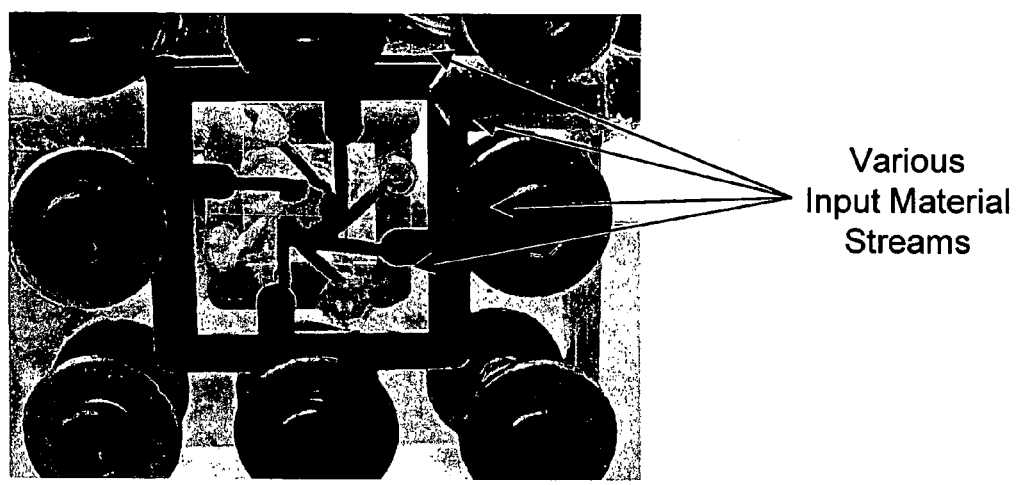
FIG. 30 illustrates a four-stream mixer for use in an embodiment of the material dispenser of the invention.

As one example of pulsing for the four-stream mixer configuration of FIG. 30, materials M1 and M2 may be pulse-dispensed into a main channel with a diameter substantially equal to that of the injector needles. Each fluid stream is split into four separate streams to increase the fluid surface-to-volume ratios and thereby increase the contact area between the fluids to enhance mixing. In this embodiment, the injection pulses are 180° out of phase, the frequency ratio determines the concentration of the mixture, and the mixture flow rate is the sum of the two average flow rates. Most if not all of the structural material may be transparent to enable both visual inspection of the mixing process as well as the ability to use an optical sensor 180 for feedback control.

Figure 31A:
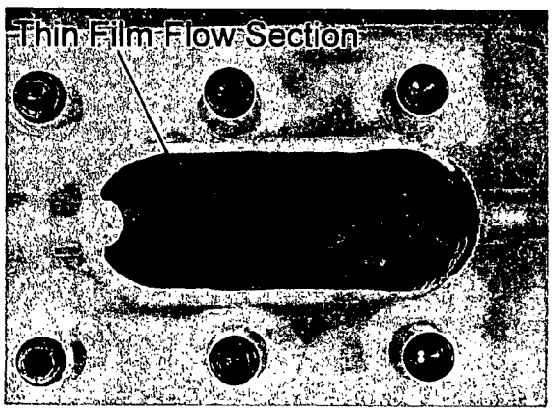
FIGS. 31A and 31B illustrate the mixing effects of a pulsed flow in the embodiments of the material dispenser of the invention.
Figure 31B:
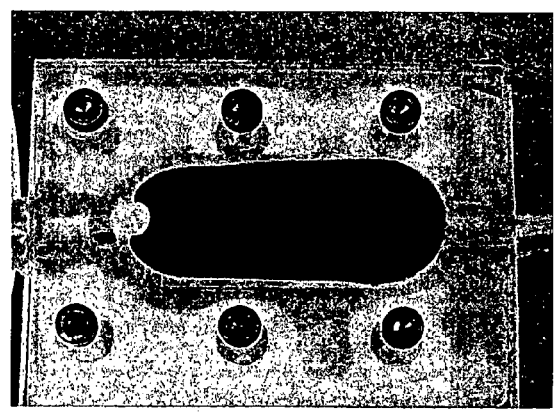

FIG. 30 and FIGS. 31A and 31B illustrate the effect of pulsing-enhanced mixing. FIG. 30 shows an example of a mixer configuration that increases the contact area of two fluids to be mixed. The mixer splits each fluid into four input streams to increase their relative surface area/contact area. FIGS. 31A and 31B illustrate the mixing effects of pulsed fluid flow for the configurations for the mixer shown in FIG. 30; image (a) is constant flow and image (b) is pulsed flow, with the OM's viewing the thin-film flow section following the mixer.

Integrated Mixing Nozzle

Figure 32A:
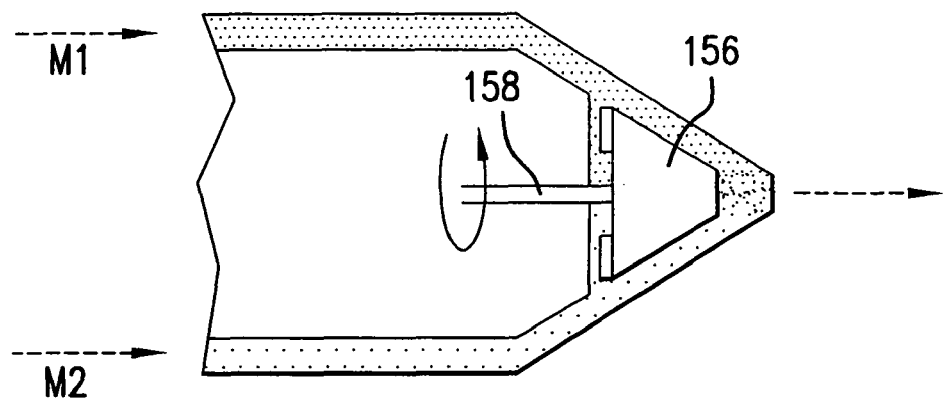
FIGS. 32A and 32B are schematic views of a rotating needle valve embodiment of the material dispenser according to the invention.
Figure 32B:
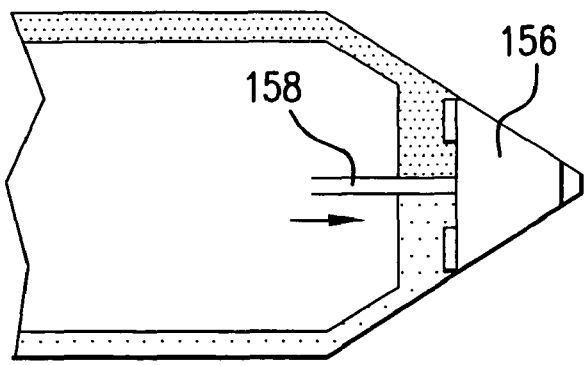

FIGS. 32A and 32B schematically illustrate an embodiment in which enhanced mixing may occur via dynamic mixing methods. The illustrated embodiment includes a rotating needle valve assembly, including a needle valve 156, a needle valve piston 158, and a rotating drive operatively coupled to the needle valve piston. The rotating drive rotates the needle valve while substantially maintaining the position of the needle valve at least partially between the output ends of the feed channels and the tip orifice.

The user may selectively control the degree of mixing achieved by the needle valve assembly. In one embodiment, the materials are mixed to substantially a homogeneous condition after passing through the mixer and then through the tip orifice. In other embodiments, less complete mixing may be achieved if desired by adjusting the angular velocity of the rotating drive. In some embodiments, the rotating needle valve assembly also includes a controller for maintaining the rotating drive at a substantially constant angular velocity, for ensuring consistent mixing.

The needle valve and the needle valve piston may be formed from any selected material, as known. In various embodiments, the needle valve may comprise rubber, stainless steel, titanium alloy or other suitable materials. Similarly, the needle valve head piston in various embodiments may be constructed of any suitable material, including a stainless steel or a titanium alloy.

The dynamic rotation of the needle valve enhances mixing. In one embodiment, the needle valve may have various defined geometries and structures to enhance mixing and decrease flow resistance. Specifically, the substantially conical illustrated embodiment of the needle valve may be utilized. Additionally, other shapes may be utilized, including spherical needle valves with small baffles (of periodic, random, or fractal geometries) on the surface. Such a shape provides a gentle curve around the needle valve to minimize shear forces yet provide a means of stirring the flow around the needle valve axis.

FIGS. 29A-29C illustrate an integrated mixing nozzle embodiment. The needle valve position in the z direction is controlled via a motion-controlled needle valve piston. The needle valve can also be rotated for enhanced mixing near the tip orifice. In embodiments wherein a single dispenser carries multiple distinct constituent materials, such as a packed array, separate valves may be provided to control independently the flow of each constituent into the mixer, as discussed in detail above.

In some embodiments, an active sensor 180 (FIG. 29A) may be integrated via a controller 181, such as piezoelectric sensors or optical means for feedback to the actuators to synchrone the pump speed and the needle valve position to allow for controlled-volume deposition. The controller in some embodiments may also comprise a feedback system for maintaining the rotating drive at a substantially constant angular velocity.

Optical Feedback to Mixing

In some embodiments, optical feedback to mixing may be provided using a commercially available charge-coupled device (CCD) camera and a PC with a frame-grabber card constitutes a platform capable of providing the necessary feedback for the actuator control system. Traditional digital particle image velocimetry (DPIV) techniques have been used for years to analyze fluid flow. This technique relies on the analysis of successive images of the flow. The digital images are decomposed into small search windows. These search windows are then cross-correlated with the next image to determine the average spatial shift of the representative flow particles. See G. M. Quenot, J. Pakleza, and T. A. Kowalewski, "Particle Image Velocimetry with Optical Flow," *Experimental Fluids* 1998, 25, 177, which is expressly incorporated herein in its entirety by this reference. This technique is not optimal due to its computational expense (it requires three 2D fast Fourier transforms for each window) and its loss of accuracy when large velocity gradients ($\Delta u$) occur within the window itself. Reducing the window size to improve spatial resolution results increases computational expense. An improvement on traditional DPIV has been suggested that utilizes an optical flow method to overcome the problems associated with DPIV. However, the authors state that it takes about ten minutes to process a pair of images with this "improvement," hardly suitable for real-time implementation in a closed-loop feedback system.

For real-time implementation, the optical feedback sensor uses a priori knowledge gained through simulations, prototype evaluation, and materials characteristics to concentrate processing efforts on key areas of the mixing process, thereby reducing computational expense. Results of modeling are used to select intelligently regions of interest for determining quality of mixing. Quality of mixing results is compared to the predicted results from modeling and used to control the mechanical mixing actuators and determine content of resultant fluid(s). Additionally, a scale-space approach is used to perform fine-detail processing only in the areas where it is required. Characterization of fluid dynamics near the tip orifice will be done at a much larger scale than near the point at which the fluids become a homogeneous mixture. Scaling will be done using the concept of local monotonicity. Locally monotonic ("lomo") images are defined as root signals of a morphological lomo filter. The morphological approach allows a multidimensional generalization of local monotonicity. Repeated application of the lomo filter produces a lomo root signal of a specified scale. By filtering at multiple scales, a lomo scale-space can be created and used in such multiscale image applications as the mixer, where fine detail is not required in certain areas. In contrast to existing linear and nonlinear scale-generating filters, the lomo filter has no spatial or gray-level bias and preserves edge localization through scale-space. See J. Bosworth and S. T. Acton, "The Morphological Lomo Filter for Multiscale Image Processing," in *Fourth International Conference on Image Processing* (1999), 157, which is expressly incorporated herein in its entirety by this reference.

Implementation of optical feedback may be expanded to a multispectral approach, which is advantageous in the DWDT/HAT system because some of the constituent mixing materials will also have thermal requirements, in particular the biological cells. Information contained in the IR region of the spectrum can then be used both for mixing control and for verification of thermal compatibility. Furthermore, it may also be necessary to extrude highly viscous polymeric materials through a heated nozzle to draw out intricate scaffold patterns.

Figure 33:
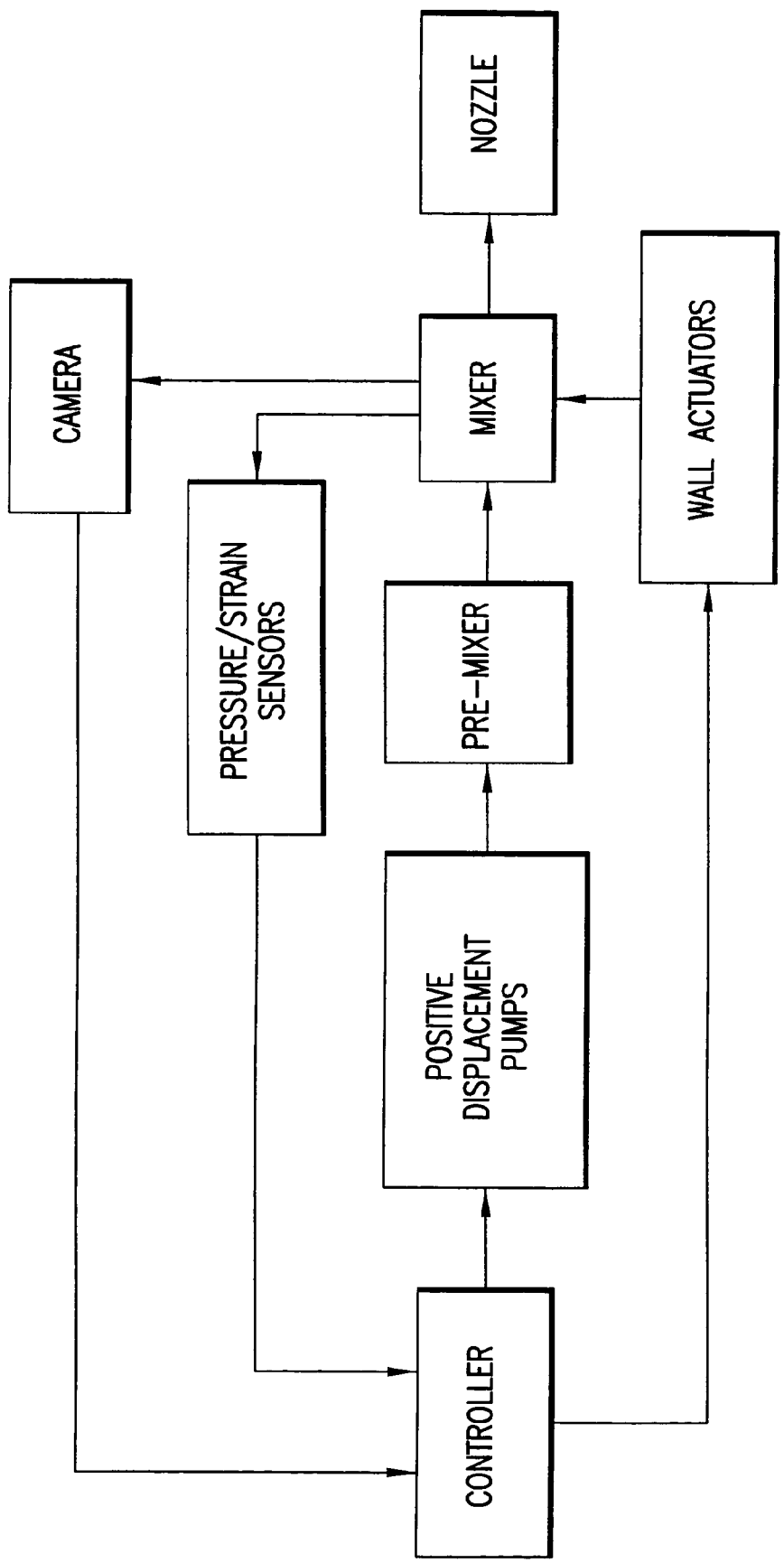
FIG. 33 is a flow chart of an exemplary method of providing feedback to a mixing system for use with the embodiments of the material dispenser of the invention.

Using a reduced, multispectral data set will allow for faster processing, efficient feature identification, quantitative quality analysis of the mixing process, and hence real-time implementation in a robust closed-loop feedback mixing system compatible with a wide range of fluid and cell characteristics. This will enable use of the HAT concept for a combinatorial tissue-engineering testbed to optimize the geospatial and temporal relationships between the cells, scaffolding materials, ECM's, nutrients, cytokines, and growth factors for the construction of the engineered tissue construct. A block diagram illustrating the complete system is illustrated in FIG. 33.

Extended and Retracted Elements

In some embodiments, the tool design may include discrete components that can be extended, retracted, lubricated, rinsed, and flushed to ensure that the functions of the integrated tool do not interfere with each other (i.e., the polymers dispensed do not obscure or coat lenses or fibers). This concept permits the tool's miniaturized material dispenser to be extended to deposit materials and then retracted to reduce contamination in the endoscopic-type device. Similarly, the imaging elements of the tool may have a constant film of saline washing over the surface, continuously cleaning the surface for the imaging and diagnostic capabilities. It may be configured in concentric cylinders. In such an embodiment, any selected component may be enclosed within a hollow cylinder (like a catheter). As the component extends and retracts through the outer cylindrical surface, the slight overpressure of saline coupled with the capillary forces can rinse off any residual material. In total, this enables the tool to be lubricated, rinsed, and then flushed. The extra saline can be removed via the material remover of the integrated tool as shown in FIGS. 4-7.

Motion and Control

Currently, MIS tools are based on a design in which the patient and surgical media are held stationary and the surgical arms are moved at a selected speed. A computer-controlled manipulator, a manual device akin to a mouse, or freehand control can achieve movement. One implementation for the motion control system is the method exemplified by computer motion for robotically controlled endoscopes and grippers used in surgical procedures, e.g., HERMES or ZEUS platforms. See M. J. McDermott, *Ambassador Magazine* 2000, (Nov.), 32; G. S. Guthart, J. K. Salisbury, in *Proceedings of the IEEE International Conference on Robotics and Actuation* (2000), 618; and Yulun Wang, Kenneth Grace, Darrin R. Uecker, and Sudipto Sur, "Motion Minimization and Compensation System for Use in Surgical Procedures," U.S. Pat. No. 5,971,976, 26 Oct. 1999, which are expressly incorporated herein in their entirety by this reference. CT, OCT, MRI, or laser prescanning data could be used to generate a computer-aided design (CAD) model of the desired tissue or bone construct. The CAD file enables the dispenser to follow the conformal surface precisely without direct surface contact. This precise control allows tight cross-section control as well as the ability to follow and write on rough, uneven surfaces, and up and over features without damaging or distorting them.

The motion of "snake" robots has been studied extensively. See S. Hirose, *Biologically Inspired Robots: Snake-Like Locomotors and Manipulators* (Oxford: Oxford Science Publications, 1993), which is expressly incorporated herein in its entirety by this reference. While several modes of movement can be performed by snakes, the motion of interest to the invention is the so-called "serpentine=motion." This movement is a gliding mode whose defining characteristic is that each part of the body makes similar tracks. The motion objective for endoscopic embodiments of the invention would be to take on this mode of movement to guarantee that every link subsequent from the head would pass through the same area as the head. Choset and Henning have termed this motion type "follow-the-leader" (FTL). See H. Choset and W. Henning, "A Follow-the-Leader Approach to Serpentine Robot Motion Planning," http://citeseer.nj.nec.com/cache/papers/cs/3705/ http:zSzzSzvoronoi.sbp.ri.cmu.eduzSz~chosetzSzpapersz Szasce99_snake.pdf/a-follow-the-leader.pdf, 2001, accessed Jun. 12, 2002, which is expressly incorporated herein in its entirety by this reference. It is attractive for endoscopic applications because the path can be negotiated by the operator by guiding the head in a predetermined pattern. The allowable passageway for the rest of the body is then defined as the path taken by the head of the endoscope. The motion-planning algorithm then directs the rest of the endoscope body through the "hoops." To augment the localization system, pressure-contact sensing can be used to sense contact with an organ and to direct the snake body away in a fashion similar to that of the Olympus Optical Company microcatheter. See Olympus Optical Co. Ltd., http://www.olympus.co.jp/indexE.html, 2002, accessed Jun. 12, 2002, which is expressly incorporated herein in its entirety by this reference.

The winding locomotion of a snakelike robot may be expressed as a wave equation. See F. Matsuno and S. Hara, "Bottom-Up and Top-Down Approaches to Dynamics of Hyper-Redundant Mechanical Systems," in *Proceedings of the 1999 IEEE International Conference on Systems, Man, and Cybernetics*, Volume 3 (IEEE, 1999), which is expressly incorporated herein in its entirety by this reference. This type of model is known as a distributed parameter model (DPM). DPM's are governed by partial differential equations and may be regarded mathematically as "infinite-dimensional (ID) systems." Guaranteed closed-loop stability of DPM's often yields ID controllers, which are impossible to implement in real systems. See F. Matsuno and S. Hara, "Bottom-Up and Top-Down Approaches to Dynamics of Hyper-Redundant Mechanical Systems," in *Proceedings of the 1999 IEEE International Conference on Systems, Man, and Cybernetics*, Volume 3 (IEEE, 1999) and Xunjing Li and Jiongmin Yong, *Optimal Control Theory for Infinite Dimensional Systems* (Birkhauser, 1995), which are expressly incorporated herein in their entirety by this reference. Approximation schemes for the ID controllers have been proposed that may serve as simplified finite-dimensional (FD) robust controllers. In some embodiments of the invention, closed-loop stability is provided by posing the optimal control problem as an optimization of a performance criterion (i.e., to minimize time, error, energy, etc.), then solve an infinite Riccati equation. See Xunjing Li and Jiongmin Yong, *Optimal Control Theory for Infinite Dimensional Systems* (Birkhauser, 1995), which is expressly incorporated herein in its entirety by this reference. This process yields an ID controller, which may then be reduced to a FD controller. In other embodiments, the DPS may to be reduced to a FD model that allows the design of a typical robust control scheme (H-infinity, sliding-mode, adaptive, etc.).

Probe Tip Movement and Platform

Figure 34A:
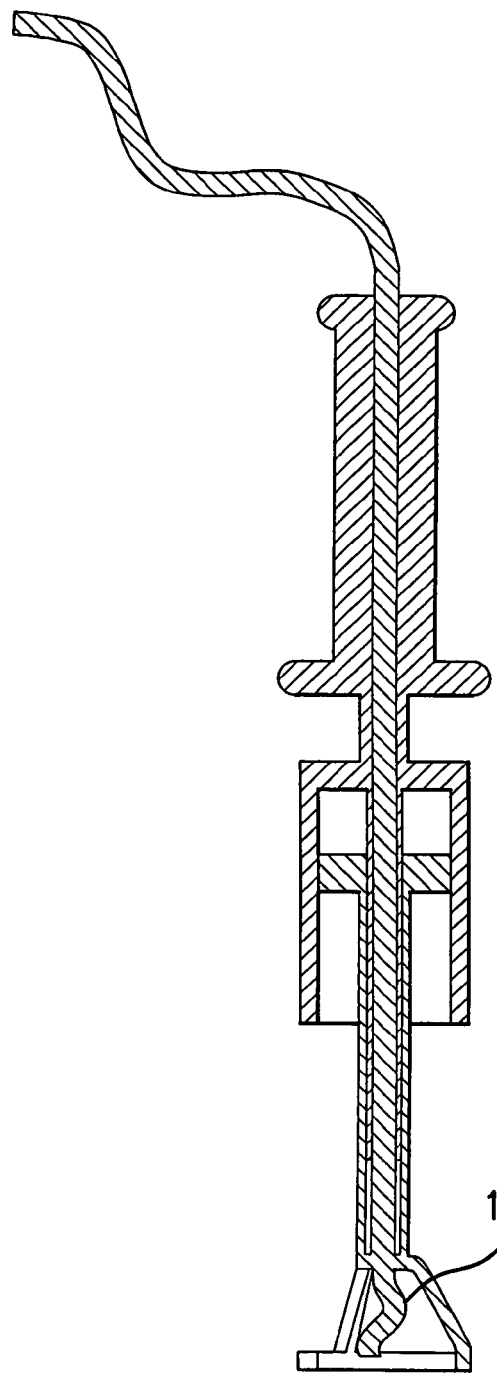
FIGS. 34A and 34B are views of an embodiment of the apparatus stabilizer according to the invention.
Figure 34B:
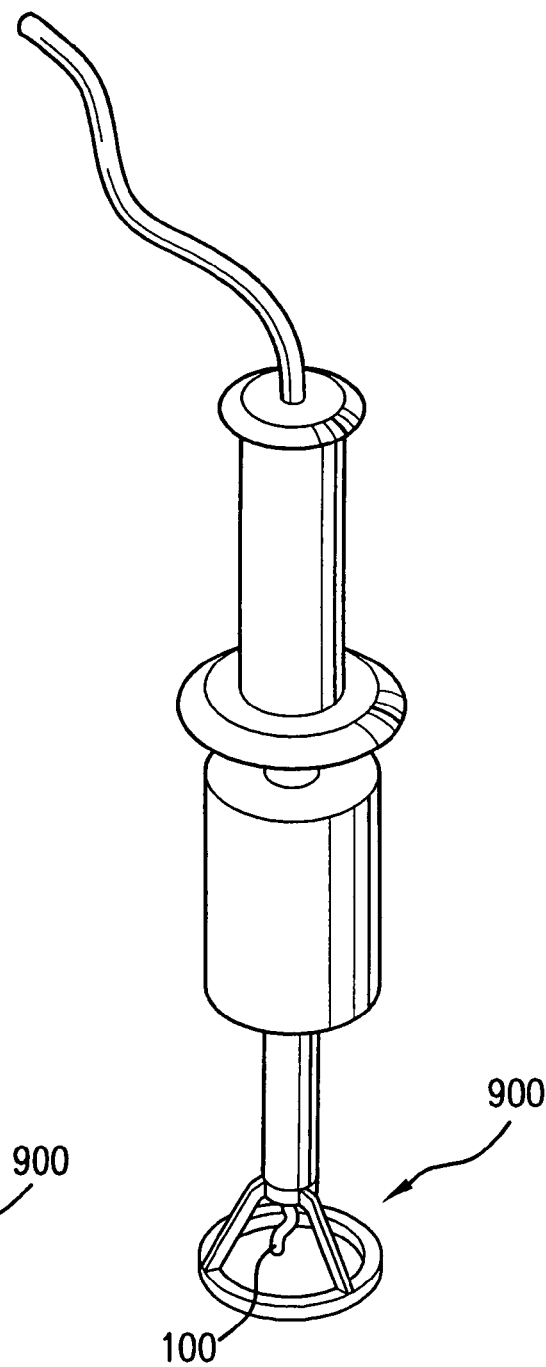

Some embodiments of the invention include devices and methods for providing accurate positioning of the tip end of the tool with respect to the substrate, even a moving substrate, during the deposition process or other processes. In one embodiment, the position of the substrate may be registered in real time by allowing a portion of the tool to make contact with the substrate and to maintain that contact. The relative displacement between the tip orifice and the substrate surface will then be fixed as long as contact with the substrate is maintained at all times. The tip end of the tool can then be positioned with respect to the stable platform. Thus, small movements of the patient can be easily accommodated. Tool placement is accomplished with micromechanical actuators or inflatable bladders. One embodiment of such a platform arrangement is illustrated in FIGS. 34A and 34B.

Sheath Variation

In another embodiment, an outer sheath with a TV camera may be inserted first, and preferably anchored, e.g., the above inflatable bladder and/or platform, and then operating components may be inserted into the sheath. The operating components may have a larger head and a smaller supply and/or positioning tube (e.g., somewhat snake-shaped), and be stored in a staggered fashion in the sheath (or completely withdrawn) and moved up to the tip as needed. This approach may minimize the size of the needed incision and the tool cross-section.

Synergies of an Integrated Tool

The HAT has the ability to add desirable and/or subtract unwanted tissues in a seamless and facile fashion without having to be repositioned. As it is virtually impossible to withdraw one tool and then reinsert it or another tool in the same position, by having all functions in the same tool, for example, any incorrectly positioned depositions can be accurately removed and then redeposited in the correct position, all without loss of registration of the tool. Similarly, combining fabrication and assembly of biocompatible scaffolds, cells, nutrients, growth factors, and other components as desired to form 3D ETC's all in one tool allows accurate positioning. Again, it all can be done without losing registration of the tool. Thus, an integrated tool not only accomplishes its tasks faster, but also much more accurately.

Detection, imaging, laser delivery, suction tubes, miniaturized dispensing and/or mixing nozzles, and cooling channels may be disposed in one bundle as shown in FIGS. 4-7 (8-12). This complete system can allow for all of the capabilities of the tool to fit within one small package, integrated and synchronized for easy operation. The HAT device and methods make revolutionary surgery possible through a ≈10-mm incision. It is also possible that several of the features could be implemented in several endoscopic-like bundles as well. As one example, one endoscopic device could be used for dispensing materials, while another could be used for imaging, detection, and laser delivery.

In Vitro HAT Methods

HAT can be used to deposit any tissue engineering material at a selected position on a substrate in vitro. Such deposition methods can be used, e.g., to develop and/or construct engineered tissue constructs and to test combinations of cells, biological molecules, and/or scaffolding materials for use in tissue engineering constructs. In vitro deposition methods can be performed using a tool having at least one material dispenser, at least one location control device, and a means for selectively synchronizing the location control device with an actuator that regulates the material dispensing function, as described hereinabove. The tissue engineering material is placed in the material dispenser of the apparatus, after which the tip orifice of the dispenser is positioned at a selected position relative to the substrate. The material dispenser is then activated, thereby depositing the tissue engineering material at the selected position on the substrate.

Tissue engineering materials can include, e.g., any cell, biocompatible scaffolding material, hydrogel, or biological molecule that affects cell growth, survival, differentiation, or other metabolic processes. Examples of such biological molecules include, but are not limited to, growth factors, adhesion factors, cytokines, hormones, signaling molecules, and cell nutrients. Additional examples of biological molecules are provided in a list hereinbelow, which is not intended to be limiting.

A material dispenser for use in the methods of the invention can include a sensoric dispensing nozzle, which can be used to deposit a dense monolayer of cells on the substrate. As used herein, a "dense monolayer of cells" is a single layer of cells deposited on a selected area of a substrate is at a density of at least 50% of the theoretical packing density (100% theoretical packing density is the maximum number of cells that can be deposited per unit area (e.g., $cm^2$)). One of ordinary skill in the art will readily understand that theoretical packing density for any given cell type depends upon the cell size (see, e.g., R. A. Flinn and P. K. Trojan, *Engineering Materials and Their Applications*, Houghton Mifflin Co., Boston, Mass., 1981, pp. 338-341). The dense monolayer of cells can be deposited on any suitable substrate, e.g., a substrate that includes a hydrogel (e.g., polypropylene fumarate-co-polyethylene glycol).

It will be apparent to one of ordinary skill in the art that the methods of the invention can be used to deposit a single tissue engineering material on a substrate, or more than one tissue engineering material on a substrate. For example, two or more tissue engineering materials can be simultaneously deposited as a layer on the substrate using the methods and tools of the invention. The tissue engineering materials can be mixed to a substantially homogeneous mixture before depositing on the substrate. The tissue engineering materials can be pre-mixed, or, alternatively, the apparatus for depositing the materials can have a separate feed channel for each tissue engineering material to be deposited. The tissue engineering materials to be deposited can then flow through a common mixing nozzle prior to being simultaneously deposited as a layer on the substrate. For example, using this approach, a gradient can be formed within the layer of deposited tissue engineering materials by controlling the amount of flow through each respective feed channel. As one of skill in the art will recognize, the methods and tools of the invention can be used to deposit a plurality (i.e., two or more) of identical or non-identical layers.

In Vivo HAT Methods

HAT can be used to deposit any tissue engineering material at a target area within a subject's body. Such in vivo deposition methods can be used, e.g., to repair, construct, or re-construct a tissue or organ within the subject's body. In vivo deposition methods can be performed using a tool having at least one material dispenser and at least one imaging device. The tool can be inserted into the subject's body through a surgical incision and positioned such that the tissue engineering material can be deposited at the target area within the subject's body, after which the material dispenser is activated such that the tissue engineering material is deposited at the target area.

Both human and non-human subjects can be treated using the tools and methods of the invention. For example, non-human subjects that can be treated using these tools and methods include mammals, e.g., but not limited to, dogs, cats, pigs, goats, sheep, horses, or cows, although birds, reptiles, and other non-mammalian animals can be treated as appropriate.

Tissue engineering materials can include, e.g., any cell, biocompatible scaffolding material, hydrogel, or biological molecule that affects cell growth, survival, differentiation, or other metabolic processes.

As discussed above with regard to in vitro methods for deposition of tissue engineering materials, it will be apparent to one of ordinary skill in the art that the in vivo deposition methods of the invention can be used to deposit a single tissue engineering material at a target area in a subject's body, or more than one tissue engineering material at a target area in a subject's body. For example, two or more tissue engineering materials can be simultaneously deposited as a layer at the target area within the subject's body using the methods and tools of the invention. The tissue engineering materials can be mixed to a substantially homogeneous mixture before depositing at the target area within the subject's body. The tissue engineering materials can be pre-mixed, or, alternatively, the apparatus for depositing the materials can have a separate feed channel for each tissue engineering material to be deposited. The tissue engineering materials to be deposited can then flow through a common mixing nozzle prior to being simultaneously deposited as a layer. A material dispenser for use in the methods of the invention can include a sensoric dispensing nozzle to deposit a dense monolayer of cells at the target area within the subject's body. For example, using this approach, a gradient can be formed within the layer of deposited tissue engineering materials by controlling the amount of flow through each respective feed channel. As one of skill in the art will recognize, the methods and tools of the invention can be used to deposit a plurality (i.e., two or more) of identical or non-identical layers.

Also as discussed above with regard to in vitro methods, a material dispenser for use in the methods of the invention can include a sensoric dispensing nozzle to deposit a dense monolayer of cells at a target area within the subject's body. For example, the dense monolayer of cells can be deposited onto a hydrogel layer at the target area within the subject's body.

Tools for use in the methods of the invention can include various other features, for example, a location control device for positioning the tool within the subject's body with respect to the target area.

Another feature that can optionally be included in tools for use in the methods of the invention is a laser. After the deposition of biocompatible scaffolding material at the target area, the laser can be activated to selectively ablate portions of the scaffolding material deposited to create channels therein, e.g., to promote vascularization of the engineered tissue construct.

HAT can also be used to destroy (i.e., ablate or excise) unwanted cells or body tissue at a target area within a subject's body, using a tool that includes at least one material dispenser, at least one imaging device, and at least one material destroyer. The tool is inserted into the subject's body and positioned such that the cells or body tissue at the target area can be destroyed by the material destroyer, after which the material destroyer is activated, thereby destroying the cells or body tissue at the target area in the subject's body. The destroyed cells or tissue can be removed by a material remover that is optionally included in the tool.

Using the methods and tools of the invention, unwanted cells at the target area can be destroyed (ablated or excised), for example, cancer cells, cartilage cells, bone cells, connective tissue cells, fat cells, or nerve cells. Likewise, unwanted or undesirable body tissue (for example, excess tissue, damaged tissue, inflamed tissue, or scar tissue, such as cartilage, bone, tendon, ligament, fat, connective tissue, or nerve tissue) can be ablated or excised.

Tools for use in destroying cells or tissues can optionally include a location control device for positioning the tool within the subject's body with respect to the target area.

Furthermore, such tools can optionally include a material dispenser. After ablating or excising unwanted cells or tissue in the target area within the subject's body, a tissue engineering material can be deposited at the target area.

The tools can also optionally include a laser. After the deposition of biocompatible scaffolding material at the target area, the laser can be activated to selectively ablate portions of the scaffolding material deposited to create channels therein, e.g., to promote vascularization of the engineered tissue construct.

In addition, the tools can optionally include means for collecting diagnostic information, and can be used to collect diagnostic information from a tissue at the target area within the subject's body. For example, diagnostic information can be collected by optical coherence tomography, infrared spectroscopy, or laser-induced fluorescence.

The present invention also provides methods for treating a target area within a subject's body, e.g., using a tool that includes at least one material destroyer, at least one imaging device, and at least one therapeutic emitter. The tool is inserted into the subject's body and positioned such that the cells or body tissue at the target area can be destroyed by the material destroyer, after which the material destroyer is selectively activated. The tool is also positioned (either simultaneously or in a subsequent step) such that the target area can be accessed by the therapeutic emitter, after which the therapeutic emitter is selectively activated, thereby treating the target area within the subject's body.

In one specific example, a set of steps for carrying out the methods of the invention to prepare engineered tissue constructs can include:

a) acquiring an image scan of a selected tissue;
b) transforming information obtained from the image scan into computer-aided design and manufacturing (CAD/CAM) data;
c) selecting materials to be dispensed and deposited;
d) selecting material dispensing and deposition parameters;
e) selecting tool operation parameters; and
f) executing the tool operation parameters and the material dispensing and deposition parameters, thereby preparing the engineered tissue construct.

The above-exemplified method can be used to prepare engineered tissue constructs in vitro or in vivo (e.g., within the body of a subject).

HAT Biological Integration Procedural Steps

An example of procedural steps involved in implementing the HAT concept is discussed below. The example is not intended to preclude necessary variations.

Computational/Software Preparatory Tasks of HAT

Acquire Image Scans

In general, operators will begin a HAT procedure by acquiring various kinds of detailed information about the tissue to be regenerated and/or constructed. The information sources can include MRI, computerized tomography (CT), and histological thin sections. (As discussed above, the HAT can also be used as an in situ CT probe.) Operators can then compile the data obtained from the various sources to create virtual images of the tissue to be removed and/or the engineered tissue construct (ETC) to be installed.

Transform Images into CAD/CAM Program

In general, operators will then transform the image information obtained in the previous step into computer-aided design and manufacturing (CAD/CAM) program data. This transformation of images into machine language allows the images to be constructed by the HAT computer automation.

Set the Operating Parameters for the HAT and Execute

This final computer-operation step necessarily follows a number of biological and tool-operational tasks described below.

Biological Preparatory Procedures

Select Materials To Be Deposited/Dispensed

Operators will select component materials from the basis of the general type of ETC required, with examples including artificial epithelial tissue, lymph-node tissue, and cartilage. The preliminary setting is extremely important because it determines the coordinate frames. Component materials can range from scaffold and extracellular matrix (ECM) materials, to cell types, to various cytokines, to various pharmaceuticals.

Scaffold and Extracellular Matrix Materials

The scaffolding, including the ECM, will generally determine many physical parameters of the ETC, including its general shape and dimensions, and will in turn be determined by requirements of the type of tissues in the ETC. Operators will specify these physical attributes and compositions based on their overall design.

Stratification

Next, operators will specify the stratification of the ETC. In this context, stratification means the determination of the numbers and types of artificial layers that will be embedded within the ETC. It primarily refers back to the type of tissue. For example, one layer above the scaffold might contain dendritic cells; the next, a pattern seeded with cells and various artificial materials for vascularization; the next, epithelial cells; the next, endothelial cells. The deposition of the strata will continue until all of the preprogrammed patterns are complete. Since the operators have determined the total size of the ETC, the dimensions of each layer will be determined automatically.

Patterns

Next, the operator will determine the various patterns, if any, to be included within each layer of the ETC strata. Kinds of patterns might include uniform designs, simple raster designs optimized to tool efficiency, fractal designs, recurrent designs, etc.

Cells

Next, the operator will specify the kinds of cells, if any, to be imbedded in each pattern of each layer of the ETC strata. Examples include dendritic cells, epithelial cells, and endothelial cells. The operator will also specify the concentration of the cells (since volume is already specified, cell count will be) and the carrier media (e.g., normal saline). These specifications will be supported from the information stored in a special database of compatibility for different media for specific kinds of cells.

Pharmaceuticals

Finally, the operator will specify the kinds of pharmaceutical additives, if any, to be imbedded in each pattern of each layer of the ETC strata. Examples include the various cytokines and growth factors, and the active fragments thereof. Some cells should be attached to the ETC, while others should be able to migrate with a certain level of motility or after a certain period; these parameters can be controlled using balances of cadhetin and integrin cytokines.

Select Deposition Parameters

Operators will then select a number of parameters specific to the act of deposition. These include the volumes of materials to be dispensed, flow rates through the nozzles, temperatures, fluids to be stored, etc. Not every such parameter must be set for every deposition.

Flow Rates, Nozzle Types, and Pump Settings

Once operators have selected the dimensions (i.e., volumes) of the materials to be deposited, then they can determine the proper flow rates, types of nozzles, and associated pump settings. Several of these parameters are expected to interact in ways that can only be determined by experimentation for a particular deposition. Nozzle types available for use with the HAT include capillaries, needle valves, through nozzles, and positive-displacement nozzles for various material constituents.

Temperatures

Next, operators will select the temperature settings for the particular deposition, depending on the requirements of the material in question. Some materials may require refrigeration to near 0° C., while others may require heating to near 37° C.

Tool Movement Path

Finally, operators will select the parameters governing the movement path of the tool, including movement rates (velocities) and patterns or rastering motions used to deposit the ETC. Some embodiments and applications require the alternation of the rastering patterns. For example, such alternating patterns help to preserve "negative angles" or "overhangs."

Tool-Operational Aspects

These actions must be performed before beginning to build the ETC. The tasks include sterilizing the components, loading the various materials into the pump and/or cartridges, etc. Some of these operations will require enclosure within a protected environment, for example, a glove box. A special workstation could be attached to or placed in proximity to the HAT proper to provide for such.

Sterilize Tool Components

Operators will sterilize the tool components as necessary. Potential sterilization methods include UV irradiation and exposure to chlorine dioxide ($ClO_2$). Although those methods cannot be combined in one stage because UV exposure of $ClO_2$ can generate toxic and reactive oxychlorine ($Cl_xO_y$) species, they can be used in sequential stages. UV irradiation for sterilization normally consists of wavelengths in the 240-280-nm regime, which can destroy unprotected DNA and RNA.

Load Materials and Containers

Operators will then load the preselected materials into the cartridges and/or pumps of the HAT as necessary. These operations can be performed in an isolated environment as necessary. Subsequently, they will load the materials containers into the HAT proper.

Complete HAT Assembly

Operators will then perform any other actions necessary to complete assembly of the HAT and to prepare for the test run.

Perform Test Run

Finally, operators will perform a test run of the deposition to make sure everything is working properly and/or to gather experimental data.

Minimally Invasive Surgery Procedures

Open Incision and Insert Endoscope Probe

When the HAT is fully prepared, surgeons will open the small incision typical of MIS procedures and will insert the endoscope probe into the patient's body.

Locate Area of Operation

Surgeons will then locate the area of the operation by numerous means, whether internal to the HAT or external. Methods of location include triangulation, vision-system input, imaging, etc.

ETC Construction Procedures
Tool Operation
Surgeons and/or HAT operators will then perform the operations necessary to construct the ETC. Such steps can include:
  Initiating CAD/CAM layer-by-layer depositions;
  Initiating laser micromachining operations (if necessary), which can include conducting a laser pre-scan, programming the laser pathway, and selecting the laser operation parameters (such as pulse duration, fluence, irradiance, and repetition rate);
  Monitoring progress of the operation using diagnostic procedures as described below;
  Intervening as necessary (for example, one possible intervention could consist of a manual override in reaction to a medical surprise, such as a cardiac event); Initiating photocuring of the scaffolding layers (if necessary);
  Flushing with saline (if necessary);
  Opening suction ports (if necessary);
  Cycling to the next layer and repeating the sequence of any or none of the above steps; and
  Terminating operations upon completion.
Diagnostic Processes
During the operation, surgeons and/or HAT operators can continually observe the procedures and perform diagnostics to ensure optimal construction of the ETC. They can then use that information to perform necessary adjustments to the operating parameters. Information signals can include:
  LIF (steady-state and/or time-resolved);
  CT;
  Infrared and/or Raman spectroscopy; and
  Laser scanning and/or range-finding signals for dynamic substrates.
Minimally Invasive Surgery Procedures
When the HAT operation has been completed, surgeons will inspect the area of the operation, then withdraw the endoscope probe and close the incision according to standard procedures.
Invasive Surgery Procedures
The HAT can also be used to conduct surgical procedures other than those considered minimally invasive. Surgeons would open and close incisions according to standard procedures. During the operation, the HAT operators and/or surgeons would perform the actions necessary to implant an ETC deposited ex vivo or to write directly an ETC in vivo in a manner akin to that of the MIS procedures though probably conducted on a larger scale.
In Vitro and In Vivo Experimental Approaches Using HAT Tools and Methods
The disclosed apparatuses, tools, and methods allow for the in vitro or in vivo delivery of multiple combinations of factors in a reproducible, observable 3D array and are therefore useful in testing the biological effects of cells and molecules combined in a threee-dimensional manner.
For example, 100 different combinations of angiogenic factors could be placed in a reproducible 3D array on a substrate in vitro, or within a living subject in vivo, and the combination that was most beneficial at promoting angiogenesis could be determined.
The disclosed apparatuses, tools, and methods can also be used, for example, to deliver multiple combinations of therapeutics directly into a solid tumor (or the remainder thereof, after surgical excision, ablation, chemo- or radiotherapy, or some other form of treatment) to determine, in a single event, which combination of therapeutics for the given tumor would be the best to treat (e.g., destroy) the tumor or the remainder thereof.

The disclosed apparatuses, tools and methods can also be used to create specific 3D scaffolding out of biologically compatible material. For example, grids of material can be composed wherein each node of the grid has a particular member of a set of reagents (e.g., cells and biological molecules, such as growth factors) deposed on it. In a single experiment, the best combination of cell and growth factor types to produce viable cells on top of the grid could be determined. Thus, use of the HAT can facilitate significant discovery of biological processes and the advancement of tissue engineering techniques. For instance, the HAT can be used by tissue engineers to uncover the appropriate microenvironment for optimized growth kinetics by exploring the interrelationships between, e.g., vascularization, surface area, pore size, cell, and growth factor placement within the scaffold.

In the examples used herein, techniques have generally been described as being in vivo as that is generally the more complex usage. However, many of the techniques herein are also useful and novel in vitro techniques. Thus, the described examples are not to be viewed as limited to in vivo usage, but are to be viewed as enabling for in vitro uses as well.

Accordingly, also disclosed are methods and reagents, as well as machines and tools, which allow for the determination of the components that make up the in vivo cellular environment. It is well understood that cells, in vivo, interact in a complex array of cell-to-cell contacts and cell-to-ECM contacts as well as molecular interactions that occur within the ECM between noncellular molecules. In addition, it is understood that cells display many molecules, including protein and nonprotein molecules, on their cell surfaces, which provide a means for interacting with the extracellular environment as well as transmitting and relaying information from the extracellular environment to the intracellular environment. This transfer of information, both extracellular and intracellular, is known generally as signal transduction. The signal transduction pathways can ultimately lead to nuclear activity, such as mRNA transcription, which can ultimately affect the cell through, for example, altering the particular cell's proliferation state. This transcription can also ultimately affect other cells through the release or transmission of information out of the cell that is received by other cells, and affects them through both intracellular and extracellular signal transduction. While it is understood that all of these activities are occurring, it is not understood precisely how they occur or how they are controlled, such that precise biological mimicry by in vivo manipulation of these pathways can occur. Other examples include understanding the differentiation pathways of stem cells as well as intracellular communication in classical immunology (e.g., native T-cell and dendritic-cell interactions). The disclosed methods, reagents, machines, and tools provide a means to determine and define these activities and pathways, and thus manipulate these activities' pathways in vitro and/or in vivo.

For example, it is understood that cells release growth factors into their extracellular environment. These growth factors can control not only the growth of the cell that released them, but they can control the growth of other cells. The amounts of growth factors that are released vary over both time and space because aberrant release causes aberrant cellular behavior. While it is understood that aberrant levels cause problems, those of skill in the art cannot predict the "normal" in vivo levels of the growth factors that are needed or desired in vivo so that the cells can be manipulated in a way that reproduces the appropriate in vivo state. By "normal" is meant the state that, for example, produces cellular homeostasis in the native in vivo environment.

The present methods, reagents, machines, and tools provide a means to address this type of problem. The issue discussed with respect to growth factors is only exemplary. The issues presented by growth factors are equally applicable to other small signaling molecules, as well to the expression and placement of ECM proteins and scaffolding molecules, surface receptors, cells, and so forth. One of the characteristics of these issues that makes determination of the in vivo-like conditions for these and other factors (meaning conditions that approximate those found in the native state, i.e., those found in vivo) difficult is that all of these factors, and more, interact in the in vivo setting. The manipulation of one can affect the performance, expression, or effect of others, which in turn can affect the performance, expression, or effect of still others. This downstream effect often cannot be predicted; it can lead to unintended results.

Thus, systems, either in vivo or in vitro, which attempt to screen for the precise in vivo amounts by looking only at the effect of the target compound are not taking into account how other molecules in the in vivo environment are being affected, and how this collateral effect can ultimately affect the in vivo situation. One reason for this is the inability to precisely and accurately deliver to a microenvironment, both in vitro and in vivo, one reagent to be tested, much less multiple reagents that could potentially also be relevant to the in vivo phenotype and effect. The disclosed methods, reagents, machines, and tools provide a means to deliver to a microenvironment, both in vivo and in vitro, not only precise and minute quantities of any single target molecule. As one example, the physical parameters that can define the microenvironment can be one cell deposited at a time if so desired. The HAT in principle can control the microenvironment library ranging from subpicomolar to millimolar concentrations of a given reagent given the size of the material deposit and its beginning molarity.

In principle, the limits of the number of different reagents that can be delivered at any given time are related to the endoscope size for in vivo applications and can be significantly large for the tabletop version of the in vitro system, i.e., the user can select multiple dispensing technologies. For example, one factor can be the number of depositions that the user is willing to make in the microenvironment. Another factor can be the number of dispensing nozzles used in the experiment. As one example for the in vivo HAT, the number of reagents can be five per endoscope. Alternatively, each tube could contain, for example, three reagents within the endoscope. If, for example, five material constituents (reagents) are present, a large set of permutations can be explored both spatially and temporally. Spatial control can be achieved by controlling valving and/or pump speed. Temporal control can be obtained by either exploiting the known degradation rate of the biocompatible scaffold or by encapsulating the reagents in time-release microcapsules. Thus, it is possible to mix the five reagents in any way possible.

The methods of the invention can be used to implement combinatorial chemistry approaches to screen for biologically active compounds to gain a better understanding of cell and tissue biology, and/or for use in the methods of the invention.

Combinatorial chemistry at one level depends on defined relationships between the molecules that allow for batch screening rather than serial screening. For example, a traditional screening procedure may identify ten different molecules that have the desired activity. In a noncombinatorial approach, each molecule can be tested for activity. At the end of testing all ten molecules, a determination can be made as to which molecule has the most desirable activity. It is clear that in this traditional scenario, the more compounds to be tested, the more time-consuming the full analysis becomes, because all compounds must be tested to determine which is best. Thus, for 10,000 potential compounds, as many tests would be required. In a typical combinatorial approach to the same problem, the molecules would be related in a way that would allow them all to be tested in a single analysis, at the end of which the molecule that worked the best could be isolated, separated, or determined relative to the molecules that work less well or not at all. This process is often termed the selection step.

Often, combinatorial approaches can be performed iteratively, meaning that more than one selection step can occur with progressively enriched populations of molecules. The number of selection steps performed is based on a number of parameters understood by those of skill in the art. These include, but are not limited to, detection abilities, the number of molecules to be tested, the background levels of the activity to be enriched, the overall range of activities contained within the library of molecules, the stringency of the selective assay, competitive influences existing between the molecules within the library, and the type of activity being targeted (i.e., enzymatic, binding, conformational change, or complexation). For example, a library of 10,000 molecules, given the conditions and parameters of the selection step, can be enriched for the desired activity tenfold. To arrive at the best molecule for the desired activity in the library, three rounds of selection can be performed. (The first round reduces the library to 1,000 different molecules; the second, to 100; the third, to ten; and the fourth, to the best single molecule.)

Biological macromolecular combinatorial chemistry can include, for example, but is not limited to, all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics." See Szostak, *TIBS* 1992, 19, 89, which is expressly incorporated herein in its entirety by this reference.

Combinatorial chemistry techniques for screening small organic molecules, proteins, antibodies and other macromolecules for desired activities are well known to those of skill in the art. Screening sets of molecules for a desired activity, whether based on small organic libraries, oligonucleotides, or antibodies, is broadly referred to as combinatorial chemistry.

As used herein, combinatorial methods and libraries include traditional screening methods and libraries as well as methods and libraries used in iterative processes as long as they involve the disclosed machines and tools.

Combinatorial chemistry ideas also apply to small-molecule libraries. Since typically small molecules themselves cannot be amplified without some knowledge of what they are, when small-molecule libraries are utilized in combinatorial approaches the libraries are typically tagged in a way that allows for identification of the subset of molecules within the enriched population. This occurs in numerous ways, but typically, the common theme is a type of encoding of the molecule such that decoding can occur, identifying those molecules that should be reproduced for use in the next selection step. Examples of a variety of small-molecule libraries and systems that can be used for combinatorial approaches are as follows. For example, techniques for making combinatorial libraries and screening combinatorial libraries to isolate molecules that bind a desired target are well known to those of skill in the art. Representative techniques and methods can be found in, but are not limited to, U.S. Pat. Nos.

5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636, respectively.

Combinatorial libraries can be made from a wide array of molecules using a number of different synthetic techniques. For example, libraries containing fused 2,4-pyrimidinediones (U.S. Pat. No. 6,025,371), dihydrobenzopyrans (U.S. Pat. Nos. 6,017,768 and 5,821,130), amide alcohols (U.S. Pat. No. 5,976,894), hydroxyamino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107), substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514), all of which are incorporated herein by these references.

The disclosed methods, compositions, machines, and tools allow the general combinatorial concept to be applied in the context of tissue engineering and in vivo screening and identification of tissue viability parameters. Tissue engineering means the generation of tissues that either replicate in vivo tissues or produce tissues that replicate in vivo tissues with precise alterations present. The disclosed methods, compositions, machines, and tools, can also be practiced in vitro, for example in cell culture. The disclosed machines and tools allow for the ablation and deposition of multiple reagents that may be involved in the connected pathways discussed for the cellular environment in a single analysis.

For example, if the issue to be addressed is which combination of factors have the greatest angiogenic effect in vivo, the present machines and tools allow for the testing of multiple, i.e., combinatorial, combinations in a single in vivo environment. One such angiogenesis example includes varying the spatial and temporal properties of microvessel endothelial cells, extracellular matrix, hydrogel scaffolds, the delivery of VEGF-165 and PDGF-BB.

Thus, rather than testing each potential combination successively to find the best, the present machines and tools allow them to be tested simultaneously. The present machines and tools can achieve this, as discussed herein, in part because of the ability to precisely and reproducibly ablate and depose not just one, but multiple reagents in multiple different combinations in a controlled 3D space.

Disclosed herein, therefore, are methods comprising delivering in vitro or in vivo multiple reagents and/or multiple combinations of reagents to be tested for activity and determining which reagents have a desired activity. Also disclosed are methods, wherein delivering the reagents further comprises use of a means capable of cellular material precision, monolayer cell deposition, precision xyz translation stages and actuation capabilities, reproducible and repeatable deposition conditions (start/stop sequences, return paths via triangulation, and speeds that can go as fast as hundreds of millimeters per second depending on the procedure).

Disclosed herein, therefore, are methods comprising delivering in vitro or in vivo multiple reagents and/or multiple combinations of reagents to be tested for activity and determining which reagents have a desired activity. Also disclosed are methods wherein delivering the reagents further comprises use of a means capable of delivery in vivo and in vitro wherein the means can be any of the means disclosed herein.

Also disclosed are methods wherein delivering the reagents further comprises use of a means capable of delivery in vivo and in vitro wherein the means comprises, one or more dispensers or orifices and one or more pumps or other material delivery means for transporting material to the dispensers.

Also disclosed are methods wherein the reagents delivered are selected from the group consisting of growth factors, cells, biological molecules, biological macromolecules, and biologically active molecules.

As any type of growth factor can be delivered with the disclosed machines and tools, a representative nonlimiting list of growth factors that can be delivered is:

Colony stimulating factor (CSF), any;
Connective tissue growth factor (CTGF);
Endothelial cell growth factor-1, platelet-derived (ECGF-1);
Endothelial growth factor (EGF), any;
Erythropoietin (Epo);
Fibroblast growth factor (FGF), any, including but not limited to FGF-1 (aFGF), FGF-2 (bFGF), FGF-3, FGF-4, FGF-5, FGF-6, FGF-7, FGF-8, FGF-9, FGF-10, FGF-11, FIG-12, FGF-13, FGF-14, FGF-15, FGF-16, FGF-17, FGF-18, FGF-19, FGF-20, FGF-21, FGF-22, and FGF-23;
Heparin binding epidermal growth factor (HBEGF);
Hepatocyte growth factor (HGF);
Hepatoma-derived growth factor (high-mobility group protein 1 like 2)(HMG-1L2);
Human B-cell growth factor (BCGF-1);
Insulin-like growth factor (IGF), any, including but not limited to IGF-I (somatomedin C) and IGF-II;
Insulin-like growth factor binding protein (IGFBP), any, including but not limited to IGFBP-1, IGFBP-2, IGFBP-3, IGFBP-4, IGFBP-5, and IGFBP-6;
Interferon (IFN), any, including but not limited to IFN-α, IFN-β, and IFN-γ;
Interleukin (IL), any, including but not limited to IL-9;
Keratinocyte growth factor (KGF), any, including but not limited to placental growth factor and VEGF-related protein;
Latent transforming growth factor beta binding protein (LTBP), any, including but not limited to LTBP-1 and LTBP-4;
Macrophage-stimulating-1 (MST1) or hepatocyte growth factor-like (HGFL);
Nerve growth factor (NGF), any, including but not limited to NGF-β and NGF-γ;
Neurite (NEGF-1);
Pancreatic beta cell growth factor (INGAP);
Placental growth factor-like (PGFL);

Platelet-derived growth factor (PDGF), any, including but not limited to PDGF-A and PDGF-C;
Pleiotrophin (heparin binding growth factor 8);
Spinal cord-derived growth factor-B (SCDGF-B);
Stem cell growth factor (SCGF);
Teratocarcinoma-derived growth factor (TDGF), any, including but not limited to TDGF-1, TDGF-2, TDGF-3, TDGF-4, TDGF-5, TDGF-6, and TDGF-7;
Transforming growth factor (TGF), any, including but not limited to TGF-α, TGF-β, TGF-β3, and TGF-β4;
Tumor necrosis factor (TNF), any;
Vascular endothelial growth factor (VEGF), any, including but not limited to VEGF-C, VEGF-D (c-fos induced growth factor), etc.; and
Vegetal related growth factor (TGFB-related)(VGR).

As any type of cell can be delivered with the disclosed machines and tools including any eukaryotic and prokaryotic cell, including any animal, plant, fungi, or bacterial cell, a representative nonlimiting list of cells that can be delivered is:
Any tissue cell, including:
bone cells,
bone marrow cells,
brain cells,
embryonic germ cells,
embryonic stem cells,
endothelial cells,
gastrointestinal cells (including intestinal cells, esophageal cells, and stomach cells),
germ cells,
heart cells,
hematopoietic cells,
kidney cells,
liver cells,
lung cells,
lymphatic cells,
muscle cells,
nerve cells,
pancreatic cells,
prostate cells,
pulmonary cells,
skin cells,
totipotent cells, and
vascular cells;
Any lineage-specific stem cell, for example including:
breast cells,
eye cells,
hematopoietic stem cells,
muscle-specific stem cells,
neural-specific stem cells,
ovary cells,
spleen cells,
thymus cells,
thyroid cells, and
uterus cells;
Any tumor cell lines, including:
adenocarcinomas,
carcinomas,
lymphomas,
melanomas,
myelomas,
neuroblastomas,
transitional cells, and
undifferentiated cells; and
Any hybridoma cell.

As any type of biological molecule can be delivered with the disclosed machines and tools, a representative nonlimiting list of biological molecules that can be delivered is:
Adhesion factors;
Amino acids;
Apoptotic factors;
Cell cycle factors;
Cell matrix factors;
Cell membrane factors;
Coenzymes;
Cytosolic factors;
Hormones;
Minerals;
Neurotransmitters;
Nucleotides;
Prostaglandins;
Retenoic acid and retenoic acid derivatives;
Transcriptional regulation factors; and
Translation regulation factors.

As any type of biological macromolecule can be delivered with the disclosed machines and tools, a representative nonlimiting list of biological macromolecules factors that can be delivered is:
Amino acids;
Carbohydrates;
Lipids;
Nucleic acids; and
Proteins.

As any type of inorganic material can be delivered with the disclosed machines and tools, a representative nonlimiting list of inorganic compounds that can be delivered is:
Metal inks or pastes (including but not limited to aluminum, copper, gold, palladium, platinum, and silver);
Semiconductor inks or pastes (including but not limited to gallium(III) arsenide, gallium(III) nitride, germanium, graphite, indium(III) phosphide, and silicon);
Dielectric inks or pastes (including but not limited to alumina, barium titanate, silica, silicon nitride, strontium titanate, and titania); and
Conducting and insulating polymers.

Although several embodiments of the invention have been disclosed in the foregoing specification, it is understood by those skilled in the art that many modifications and other embodiments in the invention can come to mind to which the invention pertains, having the benefit of the teaching presented in the foregoing description and the associated drawings. It is thus understood that the invention is not limited to the specific embodiments disclosed hereinabove, and that many modifications and other embodiments are intended to be included within the scope of the invention. Moreover, although specific terms are employed herein, they are used only in a generic and descriptive sense, and not for the purposes of limiting the described invention, and the words "a," "and," or "the" as they appear hereinabove may mean one or more, depending upon the context in which the words are used.

We claim:

1. A tool for performing biological, tissue engineering and/or medical procedures involving at least the placement of at least one constituent material at a target area within a body from a supply of the constituent material, comprising:
   a. at least one material dispenser, which dispenses constituent materials forming biocompatible scaffold material, said material dispenser being configured to include an opening, and being controlled by a computer-controlled location control device, such that said constituent material is deposited in a three-dimensional pattern or shape which three-dimensional pattern or shape defines a cell growth template within said body, and b. at least one imaging device, wherein the tool is sized and shaped to at least partially enter the body through an opening therein; and wherein each of the at least one material dispenser, comprises:
  i. a tip orifice defining an opening through which the material exits the dispenser,
  ii. at least one elongate feed channel having an inlet and a spaced outlet adjacent the tip orifice, the at least one feed channel having the constituent material therein and being sized and shaped so that the constituent material therein may flow through the at least one channel from the inlet to the outlet, and
  iii. a valve for controlling the flow of the constituent material through the outlet of the at least one feed channel, the valve being moveable between an open position, in which the constituent material is permitted to flow through the outlet, and a closed position, in which the constituent material is not permitted to flow through the outlet, and
  iv. an actuator operatively coupled to the valve for selectively moving the valve between the open position and the closed position.

2. The tool of claim 1, wherein the body is a human body.

3. The tool of claim 1, wherein the at least one imaging device comprises an in vivo endoscopic camera.

4. The tool of claim 1, further comprising at least one material remover.

5. The tool of claim 4, wherein the tool comprises a tip end and a spaced back end, and wherein the at least one material remover comprises: a. at least one vacuum generator, and b. at least one elongate vacuum channel having a first end adjacent said tip end of the tool, and a spaced second end operatively coupled to the vacuum generator, said vacuum channel being at least partially disposed within the tool.

6. The tool of claim 4, wherein the tool comprises a tip end and a spaced back end, and wherein the at least one material remover comprises:
  a. a reservoir of a flushing fluid,
  b. at least one elongate fluid channel having a first end adjacent said tip end of the tool, and a spaced second end operatively coupled to the reservoir, said fluid channel being at least partially disposed within the tool, and
  c. a pump operatively connected to the reservoir, for selectively pumping the flushing fluid from the reservoir through the at least one fluid channel.

7. The tool of claim 6, wherein the flushing fluid is selected from the group of fluids consisting of water and saline solutions.

8. The tool of claim 1, further comprising at least one temperature control device for controlling temperature characteristics of the at least one constituent material.

9. The tool of claim 1, further comprising at least one detector for evaluating tissue within the body.

10. The tool of claim 1, wherein the tool comprises a tip end and a spaced back end, and wherein the at least one material dispenser comprises a distal end adjacent the tip end of the tool, the tool further comprising means for extending the distal end of the at least one material dispenser relative to the tip end of the tool.

11. The tool of claim 1, further comprising at least one tool stabilizer for stabilizing the tool with respect to the target area.

12. The tool of claim 1, wherein said material dispenser is adapted to dispense, together with said biocompatible scaffold material, at least one of cells, nutrients, growth factors, ECM proteins, therapeutics and mixtures thereof to further define said cell growth template.

13. The method of claim 1, wherein at least two constituent materials are simultaneously deposited as a layer on the substrate, wherein each constituent material flows through a separate feed channel therefore, and wherein the at least two constituent materials simultaneously flow through a common mixing nozzle prior to being simultaneously deposited as a layer on the substrate.

14. The method of claim 1, wherein at least two constituent materials are simultaneously deposited as a layer on the substrate, wherein each constituent material to be deposited flows through a separate material dispenser.

15. A tool for performing biological, tissue engineering and/or medical procedures involving placement of at least one constituent material at a target area within a body, the tool comprising:
  a material dispenser configured to dispense a fluid comprising at least one constituent material for forming a biocompatible scaffold, the material dispenser comprising:
    i. a tip orifice defining an opening through which the constituent material exits the dispenser,
    ii. at least one elongate feed channel having an inlet and a spaced outlet adjacent the tip orifice, the at least one feed channel having the constituent material therein and being sized and shaped so that the constituent material therein may flow through the at least one channel from the inlet to the outlet, and
    iii. a valve for controlling the flow of the constituent material through the outlet of the at least one feed channel, the valve being moveable between an open position, in which the constituent material is permitted to flow through the outlet, and a closed position, in which the constituent material is not permitted to flow through the outlet, and
    iv. an actuator operatively coupled to the valve for selectively moving the valve between the open position and the closed position;
  at least one imaging device configured to acquire imaging of the body;
  wherein the tool is sized and shaped to at least partially enter the body through an opening therein.

* * * * *